(12) United States Patent
Akiyoshi et al.

(10) Patent No.: US 8,759,322 B2
(45) Date of Patent: Jun. 24, 2014

(54) HYALURONIC ACID DERIVATIVE AND PHARMACEUTICAL COMPOSITION THEREOF

(75) Inventors: Kazunari Akiyoshi, Bunkyo (JP); Takashi Nakai, Gotenba (JP); Tai Hirakura, Gotenba (JP); Tsuyoshi Shimoboji, Gotenba (JP)

(73) Assignees: National University Corporation Tokyo Medical and Dental University, Tokyo (JP); Chugau Seiyaku Kabushiki Kaisha, Tokyo (JP)

( * ) Notice: Subject to any disclaimer, the term of this patent is extended or adjusted under 35 U.S.C. 154(b) by 346 days.

(21) Appl. No.: 13/127,582

(22) PCT Filed: Nov. 5, 2009

(86) PCT No.: PCT/JP2009/068933
§ 371 (c)(1),
(2), (4) Date: May 4, 2011

(87) PCT Pub. No.: WO2010/053140
PCT Pub. Date: May 14, 2010

(65) Prior Publication Data
US 2011/0212901 A1 Sep. 1, 2011

(30) Foreign Application Priority Data

Nov. 5, 2008 (JP) ................. 2008-284103

(51) Int. Cl.
*A61K 31/728* (2006.01)
*A61K 31/715* (2006.01)
*C07H 5/04* (2006.01)
*C07H 5/06* (2006.01)

(52) U.S. Cl.
USPC ............... 514/54; 514/20.9; 536/55.1

(58) Field of Classification Search
USPC ................... 514/54, 20.9; 536/55.1
See application file for complete search history.

(56) References Cited

U.S. PATENT DOCUMENTS

| 4,851,521 | A | 7/1989 | della Valle et al. |
| 6,245,753 | B1 | 6/2001 | Byun et al. |
| 2007/0196497 | A1 | 8/2007 | Pouliquen et al. |
| 2008/0069884 | A1 | 3/2008 | Schiavinato et al. |
| 2008/0306022 | A1 | 12/2008 | Miyamoto et al. |
| 2009/0148534 | A1 | 6/2009 | Yasugi et al. |
| 2010/0204102 | A1 | 8/2010 | Akiyoshi et al. |

FOREIGN PATENT DOCUMENTS

| JP | 3292301 A | 12/1991 |
| JP | 6264802 A | 9/1994 |
| JP | 7206903 A | 8/1995 |
| JP | 2002516355 A | 6/2002 |
| JP | 2006291097 A | 10/2006 |
| JP | 2008531148 T | 8/2008 |
| WO | 96/35721 A1 | 11/1996 |
| WO | WO 9961481 A1 | 12/1999 |
| WO | 0222154 A2 | 3/2002 |
| WO | WO 2002022154 A2 | 3/2002 |
| WO | 03099992 A2 | 12/2003 |
| WO | WO 2003099992 A2 | 12/2003 |
| WO | 2004035629 A2 | 4/2004 |
| WO | WO 2004035629 A2 | 4/2004 |
| WO | 2004050712 A2 | 6/2004 |
| WO | WO 2004050712 A1 | 6/2004 |
| WO | 2005051416 A1 | 6/2005 |
| WO | WO 2005051416 A1 | 6/2005 |
| WO | 2006028110 A1 | 3/2006 |
| WO | WO 2006028110 A1 | 3/2006 |
| WO | WO 2006092233 A1 | 9/2006 |
| WO | 2007043702 A1 | 4/2007 |
| WO | WO 2007043702 A1 | 4/2007 |
| WO | 2008136536 A1 | 11/2008 |
| WO | WO 2008136536 A1 | 11/2008 |
| WO | 2009074678 A2 | 6/2009 |
| WO | WO 2009074678 A2 | 6/2009 |

OTHER PUBLICATIONS

Choi et al. (J. Mater. Chem., 2009, 19, 4102-4107).*
Akiyama E. et al., "Self-assembled Nanogels of Cholesteryl-modified Polysaccharides: Effect of the Polysaccharide Structure on Their Association Characteristics in the Dilute and Semi-dilute Regimes", Biomacromolecules, 2007, vol. 8, No. 8, pp. 2366-2373.
Akiyoshi K. et al., "Microscopic Structure and Thermoresponsiveness of a Hydrogel Nanoparticle by Self-Assembly of a Hydrophobized Polysaccharide", Macromolecules, vol. 30, 1997, pp. 857-861.
Akiyoshi K. et al., "Molecular Chaperone-Like Activity of Hydrogel Nanoparticles of Hydrophobized Pullulan: Thermal Stabilization with Refolding of Carbonic Anhydrase B", Bioconjugate Chemistry, 1999, vol. 10, No. 3, pp. 321-324.

(Continued)

*Primary Examiner* — Shaojia Anna Jiang
*Assistant Examiner* — Michael C Henry
(74) *Attorney, Agent, or Firm* — Browdy and Neimark, PLLC

(57) ABSTRACT

The present invention provides a hydrophobic group-introduced hyaluronic acid derivative comprising at least one repeating unit represented by the formula (I):

[Formula 1]

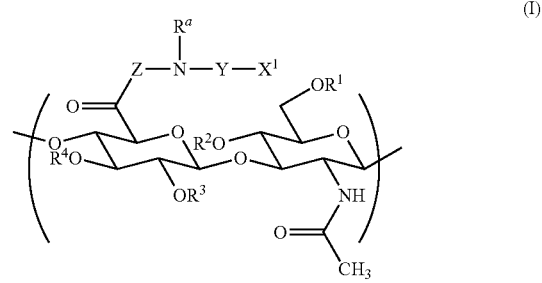

wherein $R^1$, $R^2$, $R^3$, $R^4$, Z, n, Ra, Y, and $X^1$ are as defined in the specification.

30 Claims, 63 Drawing Sheets

(56) References Cited

OTHER PUBLICATIONS

Akiyoshi K. et al., "Self-Aggregates of Hydrophobized Polysaccharides in Water Formation and Characteristics of Nanoparticles", Macromolecules, vol. 26, No. 12, 1993, pp. 3062-3068.

Akiyoshi K. et al., "Self-assembled hydrogel nanoparticle of cholesterol-bearing pullulan as a carrier of protein drugs: Complexation and stabilization of insulin", Journal of Controlled Release, vol. 54, No. 3, 1998, pp. 313-320.

Akiyoshi K. et al., "Self-assembly of polymer amphiphiles: thermodynamics of complexation between bovine serum albumin and self-aggregate of cholesterol-bearing pullulan", Colloids and Surfaces A: Physicochemical and Engineering Aspects, vol. 112, No. 2-3, 1996, pp. 91-95.

Banzato A. et al., "A Paclitaxel-Hyaluronan Bioconjugate Targeting Ovarian Cancer Affords a Potent In vivo Therapeutic Activity", Clinical Cancer Research, 2008, vol. 14, No. 11, pp. 3598-3606.

Carrasquillo K. et al., "On the Structural Preservation of Recombinant Human Growth Hormone in a Dried Film of a Synthetic Biodegradable Polymer", Journal of Pharmaceutical Sciences, 1999, vol. 88, No. 2, pp. 166-173.

Choi K.Y. et al., "Hydrogel Nanoparticles Based on Hyaluronic Acid," 34th Annual Meeting & Exposition of the Controlled Release Society, Jul. 7-11, 2007, Long Beach, California USA, Poster Session I, No. 244.

Choi K.Y. et al., "Self-assembled hyaluronic acid nanoparticles as a potential drug carrier for cancer therapy: synthesis, characterization, and in vivo biodistribution", Journal of Materials Chemistry, vol. 19, pp. 4102-4107, 2009.

Coradini D. et al., "Inhibition of Hepatocellular Carcinomas in vitro and Hepatic Metastases in vivo in Mice by the Histone Deacetylase Inhibitor HA-But", Clinical Cancer Research, 2004, vol. 10, pp. 4822-4830.

Creuzet C. et al., "New associative systems based on alkylated hyaluronic acid. Synthesis and aqueous solution properties", Polymer, vol. 47, No. 8, 2006, pp. 2706-2713.

Crotts G. et al., "Protein delivery from poly(lactic-co-glycolic acid) biodegradable microspheres: release kinetics and stability issues", Journal of Microencapsulation, 1998, vol. 15, No. 6, pp. 699-713.

Fraser J.R.E. et al., "Plasma clearance, tissue distribution and metabolism of hyaluronic acid injected intravenously in the rabbit", Biochemical Journal, 1981, vol. 200, No. 2, pp. 415-424.

Fraser J. R. E. et al., "Uptake of circulating hyaluronic acid by the rat liver Cellular localization in situ", Cell and Tissue Research, 1985, vol. 242, No. 3, pp. 505-510.

Lee H. et al., "Hyaluronic Acid-Paclitaxel Conjugate Micelles: Synthesis, Characterization, and Antitumor Activity", Bioconjugate Chemistry, 2008, vol. 19, No. 6, pp. 1319-1325.

Lee H. et al., "Target-specific intracellular delivery of siRNA using degradable hyaluronic acid nanogels", Journal of Controlled Release, vol. 119, No. 2, 2007, pp. 245-252.

Liu C.G. et al., "Self-assembled nanoparticles based on linoleic-acid modified chitosan: Stability and adsorption of trypsin", Carbohydrate Polymers, vol. 62, No. 3, 2005, pp. 293-298.

Luo Y. et al., "Synthesis and Selective Cytotoxicity of a Hyaluronic Acid-Antitumor Bioconjugate", Bioconjugate Chemistry, 1999, vol. 10, No. 5, pp. 755-763.

Luo Y. et al., "Targeted Delivery of Doxorubicin by HPMA Copolymer-Hyaluronan Bioconjugates", Pharmaceutical Research, 2002, vol. 19, No. 4, pp. 396-402.

Morimoto N. et al., "Design of Hybrid Hydrogels with Self-Assembled Nanogels as Cross-Linkers: Interaction with Proteins and Chaperone-Like Activity", Biomacromolecules, vol. 6, No. 4, 2005, pp. 1829-1834.

Mráček, A. et al., "The diffusion process of sodium hyaluronate (Na-HA) and Na-HA-n-alkyl derivatives films swelling", Journal of Biomedical Materials Research Part A, 2007, vol. 83A, No. 1, pp. 184-190.

Nishikawa T. et al., "Macromolecular Complexation between Bovine Serum Albumin and the Self-Assembled Hydrogel Nanoparticle of Hydrophobized Polysaccharides", Journal of the American Chemical Society, 1996, vol. 118, pp. 6110-6115.

Nishikawa T. et al., "Supramolecular Assembly Between Nanoparticles of Hydrophobized Polysaccharide and Soluble Protein Complexation between the Self-Aggregate of Cholesterol-Bearing Pullulan and alpha-Chymotrypsin", Macromolecules, vol. 27, No. 26, 1994, pp. 7654-7659.

Nomura Y. et al., "Protein refolding assisted by self-assembled nanogels as novel artificial molecular chaperone", FEBS Letters, 2003, vol. 553, No. 3, pp. 271-276.

Peer D. et al., "Tumor-Targeted Hyaluronan Nanoliposomes Increase the Antitumor Activity of Liposomal Doxorubicin in Syngeneic and Human Xenograft Mouse Tumor Models", Neoplasia, 2004, vol. 6, No. 4, pp. 343-353.

Platt V.M. et al., "Anticancer Therapeutics: Targeting Macromolecules and Nanocarriers to Hyaluronan or CD44, a Hyaluronan Receptor", Molecular Pharmaceutics, 2008, vol. 5, No. 4, pp. 474-486.

Yadav A.K. et al., "An insight on hyaluronic acid in drug targeting and drug delivery", Journal of Drug Targeting, 2008, vol. 16, No. 2, pp. 91-107.

Yadav A.K. et al., "Development and characterization of hyaluronic acid-anchored PLGA nanoparticulate carriers of doxorubicin", Nanomedicine: Nanotechnology, Biology and Medicine, 2007, vol. 3, No. 4, pp. 246-257.

Zhou, Bin et al., "Identification of the Hyaluronan Receptor for Endocytosis (HARE)", The Journal of Biological Chemistry, 2000, vol. 275, No. 48, pp. 37733-37741.

Extended European Search Report issued by the European Patent Office on Apr. 4, 2013, in corresponding Application No. 09824839.6 (5 pages).

* cited by examiner

Figure 12
Free EPO in the presence of HA-Chol
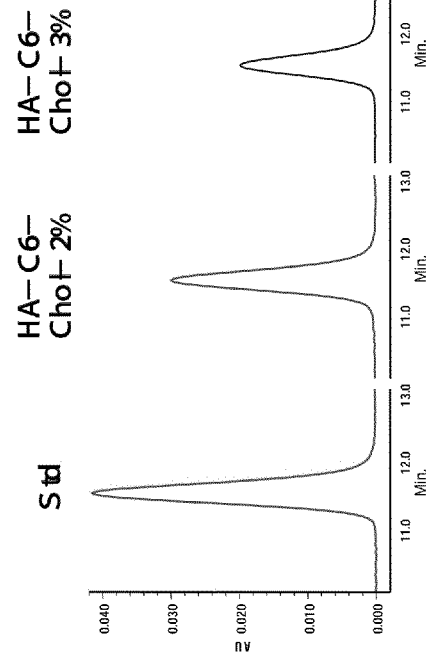
Free EPO after addition of HP-β-CD
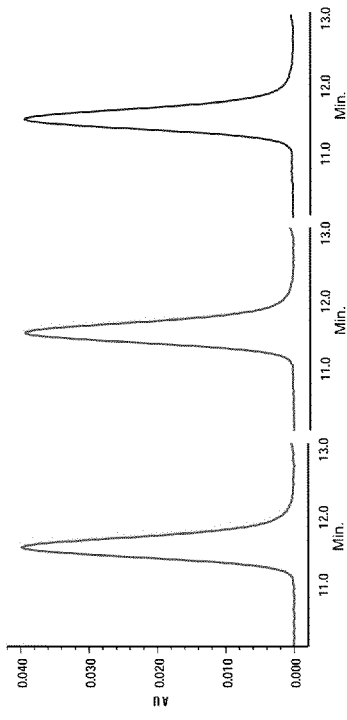

Comparative Sample 2-2

Sample 21-2

Sample 21-5

Sample 21-6

Sample 21-7

HYALURONIC ACID DERIVATIVE AND PHARMACEUTICAL COMPOSITION THEREOF

TECHNICAL FIELD

The present invention relates to a novel hydrophobic group-introduced hyaluronic acid derivative and a pharmaceutical composition comprising such a hyaluronic acid derivative, particularly a pharmaceutical composition comprising a pharmacologically active protein and/or peptide.

BACKGROUND ART

In recent years, formulations containing proteins and peptides as active ingredients have been developed as a result of advancement of genetic recombination and chemical synthesis technologies, and the number of such formulations is increasing every year. However, proteins and peptides are not easily absorbed from the gastrointestinal tract, mucous membrane, etc. Furthermore, proteins and peptides are unstable in the body, and have a short half-life in blood. Hence, protein formulations and peptide formulations must be administered by injection repeatedly at frequent intervals, thus imposing excessive burdens on patients as well as medical staff. There is therefore a demand for a sustained-release DDS matrix for encapsulating a protein or peptide without impairing pharmacological activity. Further, in terms of administration efficiency, it is desirable to encapsulate as much protein and/or peptide as possible into a matrix.

It is known that the pharmacological activity of proteins and peptides largely depends on their higher-order structures, and is impaired by denaturation and aggregation arising from external environments such as contact with an organic solvent or air interface, pressure, temperature, and pH. It is also known that administration of a denatured or aggregated protein into the body increases risks of antigenicity and the like. As to a sustained-release formulation having a protein or peptide as an active ingredient, it is required to ensure stability of the protein or peptide during a step of producing the formulation, storage of the formulation, and until the release of the active ingredient in the body after administration.

Attempts have been made to prepare practical sustained-release formulations based on a biodegradable polymer matrix such as a polylactic acid-polyglycolic acid copolymer (PLGA), but such formulations are reported to cause protein denaturation or aggregation due to matrix hydrophobicity and as a result of manipulations required for formulation (e.g., emulsification, drying, acidification) (Non-patent Documents 1 and 2).

On the other hand, there are also reports of sustained-release formulations based on a hydrophilic hydrogel matrix, but no such formulations are yet available for practical application due to problems of protein stability during a gelling step, etc.

In terms of safety, matrices used for formulations should have non-antigenicity, non-mutagenicity, non-toxicity, and biodegradability. There is not known any sustained-release formulation ready for practical use in all aspects, i.e., encapsulation amount and recovery ratio of proteins or peptides, as well as safety.

Some recent reports have proposed the use of polysaccharides as matrixes for drug carriers. Among them, hyaluronic acid (HA), a biomaterial (polysaccharide) isolated from the vitreous body of bovine eyes in 1934 by K. Meyer, has been known as a major component of extracellular matrix for a long time. HA is a kind of glycosaminoglycan composed of disaccharide unit(s) in which D-glucuronic acid and N-acetylglucosamine are linked to one another via $\beta(1\rightarrow 3)$ glycosidic linkages. There is no difference among species in the chemical and physical structure of HA and humans also have a metabolic system for HA. HA is therefore one of the safest medical biomaterials in terms of immunity and toxicity. Recent years have enabled microbial mass production of high-molecular-weight HA and also have allowed practical use of HA in the fields of therapeutic agents for degenerated cartilage, cosmetics, etc.

Having non-antigenicity, non-mutagenicity, non-toxicity, and biodegradability, HA appears to be preferred as a matrix of a sustained-release formulation in terms of safety. To date, there have been many reports of formulations using HA as a matrix; use of modified HA for the purpose to prolong residence time in blood (Patent Document 1), use of an alkyl chain-introduced HA derivative for the purpose to prolong residence time in the knee joint (Patent Document 2), use of in situ crosslinked HA gel for sustained release of a protein (Patent Document 3), and use of a hyaluronic acid ester solid for sustained release of a bone morphogenetic protein (BMP) (Patent Document 4) have been reported.

On the other hand, there are several reports of matrices that are spontaneously complexed with a protein or peptide in an aqueous solution in the absence of an organic solvent, and such matrices are produced using, mainly, polysaccharide or polyamino acid as a raw material.

As an exemplary case of a pharmaceutical formulation using a polyamino acid derivative as a matrix, the use of a tocopherol-introduced polyglutamic acid matrix is reported (Patent Document 5).

With regard to a polysaccharide derivative matrix, it is reported that a pullulan derivative in which a cholesteryl group or the like is introduced forms a nano-size particle in an aqueous solution, and serves as a host molecule which is complexed with a hydrophobic low-molecular-weight substance, a peptide, a protein or the like (Non-patent Documents 3 to 10). A thermodynamic evaluation of the pullulan derivative after protein incorporation shows that the incorporated protein forms a hydrogen bond with a hydroxy group of pullulan and is thereby stabilized (Non-patent Document 11).

There is also a report of the use of carboxymethyl cellulose (CMC) (Patent Document 6) and linoleic acid-introduced chitosan (Non-patent Document 12) as raw materials for forming a complex with a protein. Furthermore, Patent Document 8, which was published after the priority date of the subject application, reports a composition comprising a hyaluronic acid derivative having a crosslinkable group and a hydrophilic polysaccharide derivative having a hydrophobic group, wherein the hyaluronic acid derivative having a crosslinkable group is prepared by the bridge-formation reaction of hyaluronic acid or a derivative thereof having a crosslinkable group in the presence of the hydrophilic polysaccharide derivative.

It is reported that HA receptors such as CD44, RHAMM (receptor for hyaluronic acid-mediated motility), LYVE-1 (lymphe vessel endothelial HA receptor-1), and HARE (hyaluronic acid receptor for endocytosis) are present in the body (Non-patent Documents 18 and 19). Especially CD44 and RHAMM are overexpressed in many cancer cells. Thus, attempts have been made to use HA as a cancer targeting carrier matrix. Examples thereof include paclitaxel-HA conjugates (Non-patent Documents 20 to 22 and Patent Document 9), camptothecin-HA conjugates (Patent Document 10), doxorubicin-HPMA[N-(2-hydroxypropyl)methacrylamide]-HA conjugates (Non-patent Document 23), butyric acid-HA conjugates (Non-patent Document 24), doxorubicin-encapsulating HA-PEG-PLGA nanoparticles (Non-patent Document 25), siRNA-encapsulating HA gels (Non-patent Document 26), doxorubicin-encapsulating HA-coated liposomes (Non-patent Document 27), etc. Non-patent Document 28, which was published after the priority date of the subject application, reports HA derivatives conjugated to cholic acid via an ethylenediamine linker introduced via an amide bond. It is reported that carriers having the above HA matrices are efficiently incorporated into CD44-hyperexpressed cells in vitro (e.g., Non-patent Document 20). However, it is known that when systemically administered, HA is instantaneously incorporated into HARE receptors present in sinusoidal endothelium such as liver and then metabolized, and it is eliminated rapidly from blood (Non-patent Documents 29 to 31). Thus, to achieve efficient cancer targeting using HA matrices, a carrier with reduced uptake by liver and prolonged residence time in blood is needed.

CITATION LIST

Patent Documents

Patent Document 1: International Publication No. WO2006/028110
Patent Document 2: International Publication No. WO2006/092233
Patent Document 3: International Publication No. WO2004/050712
Patent Document 4: International Publication No. WO2003/099992
Patent Document 5: International Publication No. WO2005/051416
Patent Document 6: International Publication No. WO2002/022154
Patent Document 7: JP 62-64802 A
Patent Document 8: International Publication No. WO2008/136536
Patent Document 9: International Publication No. WO2004/035629
Patent Document 10: International Publication No. WO2009/074678

Non-Patent Documents

Non-patent Document 1: J. Pharm. Sci., Vol. 88, pp. 166-173, 1999
Non-patent Document 2: J. Microencapsulation, Vol. 15, pp. 699-713, 1998
Non-patent Document 3: Macromolecules, Vol. 26, pp. 3062-3068, 1993
Non-patent Document 4: Macromolecules, Vol. 30, pp. 857-861, 1997
Non-patent Document 5: Macromolecules, Vol. 27, pp. 7654-7659, 1994
Non-patent Document 6: J. Am. Chem. Soc. Vol. 118, pp. 6110-6115, 1996
Non-patent Document 7: Bioconjugate Chem., Vol. 10, pp. 321-324, 1999
Non-patent Document 8: FEBS Letters, Vol. 533, pp. 271-276, 2003
Non-patent Document 9: Biomacromolecules, Vol. 6, pp. 1829-1834, 2005
Non-patent Document 10: J. Controlled Release, Vol. 54, pp. 313-230, 1998
Non-patent Document 11: Colloids and Surfaces, Vol. 112, pp. 91-95, 1996
Non-patent Document 12: Carbohydrate Polymers, Vol. 62, pp. 293-298, 2005
Non-patent Document 13: Ki Young Chol et al., "Hydrogel Nanoparticles Based on Hyaluronic Acid", 34$^{th}$ Annual Meeting & Exposition of the Controlled Release Society, Jul. 7-11, 2007, Long Beach, Calif. USA, Poster Session I, No. 244 (CD of conference presentation proceedings)
Non-patent Document 14: Polymer, Vol. 47, 2706-2713, 2006
Non-patent Document 15: Journal of Biomedical Materials Research Part A, Vol. 83A, No. 1, pp. 184-190, 2007
Non-patent Document 16: Biomacromolecules, Vol. 8, pp. 2366-2373, 2007
Non-patent Document 17: Carbohydrate Polymers, Vol. 62, pp. 293-298, 2005
Non-patent Document 18: MOLECULAR PHARMACEUTICS, Vol. 5, pp. 474-486, 2008
Non-patent Document 19: Journal of Drug Targeting, Vol. 16, pp. 91-107, 2008
Non-patent Document 20: Bioconjugate Chem., Vol. 10, pp. 755-763, 1999
Non-patent Document 21: Clinical Cancer Research, Vol. 14, pp. 3598-3606, 2008
Non-patent Document 22: Bioconjugate Chem., Vol. 19, pp. 1319-1325, 2008
Non-patent Document 23: Pharmaceutical Research, Vol. 19, pp. 396-402, 2002
Non-patent Document 24: Clinical Cancer Research, Vol. 10, pp. 4822-4830, 2004
Non-patent Document 25: Nanomedicine: Nanotechnology, Biology, and Medicine, Vol. 3, pp. 246-257, 2007)
Non-patent Document 26: Journal of Controlled Release, Vol. 119, pp. 245-252, 2007)
Non-patent Document 27: Neoplasia, Vol. 6, pp. 343-353, 2004
Non-patent Document 28: Journal of Materials Chemistry, Vol. 19, pp. 4102-4107, 2009
Non-patent Document 29: Cell and Tissue Research, Vol. 243, pp. 505-510, 1985
Non-patent Document 30: THE JOURNAL OF BIOLOGICAL CHEMISTRY, Vol. 275, pp. 37733-37741, 2000
Non-patent Document 31: The Biochemical journal, Vol. 200, pp. 415-424, 1981

SUMMARY OF INVENTION

Technical Problem

Not all the raw materials previously reported as matrices for sustained-release formulations of proteins and peptides possess adequate properties. For example, there is uncertainty about biocompatibility and biodegradability in a case of using a matrix produced using as raw materials polyglutamic acid, chitosan, pullulan, and/or CMC that are not present in human body. Especially in cases in which repeated administration or high-dose administration is required, there is concern about an effect of such matrices on the living body. Further, the water solubility of cholesterol-bearing pullulan decreases with an increasing amount of introduction of a hydrophobic group(s) such as cholesterol. Thus, there is a demand for a carrier which enables encapsulation of a greater amount of a protein.

There is also a demand for a carrier which enables encapsulation of a protein, peptide, low-molecular-weight substance, and/or nucleic acid as a drug and can be used as a carrier for sustained release in blood or a targeting carrier, especially a carrier with excellent residence time in blood.

An object of the present invention is to provide a pharmaceutical formulation matrix excellent in safety, in particular, a matrix for a carrier which enables efficient encapsulation of a large amount of a pharmacologically active protein or peptide used as a drug while retaining the pharmacological activity, and a matrix which can be used as a carrier for sustained release in blood and a targeting carrier excellent in residence time in blood and is capable of serving as a local (e.g., in the subcutis) sustained-release carrier which enables sustained release of a drug.

Solution to Problem

As a result of intensive efforts made to overcome the problems stated above, the inventors have found that a hyaluronic acid derivative in which a particular hydrophobic group is introduced associates spontaneously in an aqueous solution while encapsulating a large amount of a drug, especially a pharmacological active protein or peptide. They also have found that there is a range of an introduction ratio of hydrophobic groups in which the hyaluronic acid derivative aggregates significantly under the physiological concentration of salts to form a precipitate, and there is also a range in which the hyaluronic acid derivative forms stable particles even under the physiological concentration of salts and disperses stably in water. They also have found that the residence time in blood of a hyaluronic acid derivative produced using HA of a particular molecular weight as a raw material is prolonged significantly. These findings led to the completion of the present invention.

Specifically, the present invention relates to a hydrophobic group-introduced hyaluronic acid derivative which associates spontaneously in an aqueous solution, enables efficient encapsulation of drugs, particularly pharmacologically active proteins or peptides, while retaining their biological activity, aggregates significantly at the physiological salt concentration (or disperses even at the physiological salt concentration), and is excellent in residence time in blood, a method for producing the same, a pharmaceutical composition comprising a drug and the hyaluronic acid derivative, and a method for producing the same.

In one aspect, the present invention provides a hydrophobic group-introduced hyaluronic acid derivative comprising at least one repeating unit represented by the formula (I):

[Formula 1]

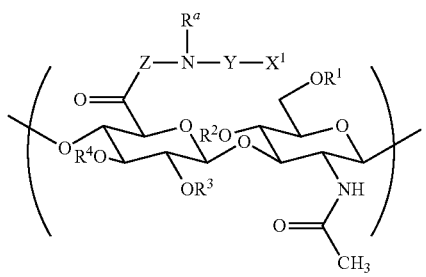

(I)

wherein $R^1$, $R^2$, $R^3$, and $R^4$ are each independently selected from a hydrogen atom, $C_{1-6}$ alkyl, formyl, and $C_{1-6}$ alkylcarbonyl;

Z represents a direct bond or a peptide linker comprising 2 to 30 arbitrary amino acid residues;

$X^1$ is a hydrophobic group selected from the groups represented by the following formulas:
—$NR^b$—R,
—$NR^b$—COO—R,
—$NR^b$—CO—R,
—$NR^b$—CO—$NR^c$—R,
—COO—R,
—O—COO—R,
—S—R,
—CO—$Y^a$—S—R,
—O—CO—$Y^b$—S—R,
—$NR^b$—CO—$Y^b$—S—R, and
—S—S—R;

$R^a$, $R^b$, and $R^c$ are each independently selected from a hydrogen atom, $C_{1-20}$ alkyl, amino $C_{2-20}$ alkyl, and hydroxy $C_{2-20}$ alkyl, wherein 1 to 3 groups selected from —O— and —$NR^f$— may be inserted into an alkyl moiety of these groups;

$R^f$ is selected from a hydrogen atom, $C_{1-12}$ alkyl, amino $C_{2-12}$ alkyl, and hydroxy $C_{2-12}$ alkyl, wherein 1 or 2 groups selected from —O— and —NH— may be inserted into an alkyl moiety of these groups;

R is a steryl group;

Y is $C_{2-30}$ alkylene or —$(CH_2CH_2O)_m$—$CH_2CH_2$—, wherein 1 to 5 groups selected from —O—, —$NR^g$— and —S—S— may be inserted in the alkylene;

$R^g$ is selected from a hydrogen atom, $C_{1-20}$ alkyl, amino $C_{2-20}$ alkyl, or hydroxy $C_{2-20}$ alkyl, wherein 1 to 3 groups selected from —O— and —NH— may be inserted in an alkyl moiety of these groups;

$Y^a$ is $C_{1-5}$ alkylene;

$Y^b$ is $C_{2-8}$ alkylene or $C_{2-8}$ alkenylene; and m is an integer selected from 1 to 100.

In one aspect, the present invention provides a hydrophobic group-introduced hyaluronic acid derivative, comprising at least one repeating unit represented by the formula (Ia):

[Formula 2]

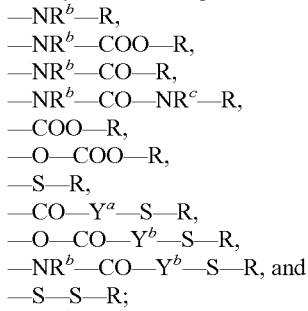

(Ia)

wherein $R^1$, $R^2$, $R^3$, and $R^4$ are each independently selected from a hydrogen atom, $C_{1-6}$ alkyl, formyl, and $C_{1-6}$ alkylcarbonyl;

X is a hydrophobic group represented by —$NR^a$—Y—$NR^b$—COO—R;

$R^a$ and $R^b$ are each independently selected from a hydrogen atom and $C_{1-6}$ alkyl;

R is a steryl group;

Y is $C_{2-30}$ alkylene or —$(CH_2CH_2O)_m$—$CH_2CH_2$—; and m is an integer selected from 1 to 100.

In a case where the hyaluronic acid derivative of the present invention comprises two or more repeating units each represented by the formula (I), the repeating units may be the same or different. The hyaluronic acid derivative may be modified at a position other than the repeating unit(s) of the formula (I); for example, the hydroxy group may be converted into —O($C_{1-6}$ alkyl), —O(formyl), —O($C_{1-6}$ alkylcarbonyl) and the like, and the carboxy group may be converted into an amide or ester or may form a salt.

In another aspect of the present invention, the group —Z—N($R^a$)Y—$X^1$ of the above formula (I) is selected from the groups represented by the following formulas:

—NH—$(CH_2)_{mz}$—NH—R;
—NH—$(CH_2)_{mz}$—NH—COO—R;
—NH—$(CH_2CH_2O)_m$—$CH_2CH_2$—NH—COO—R;
—NH—$(CH_2)_{mz}$—COO—R;
—NH—$(CH_2CH_2O)_m$—$CH_2CH_2$—COO—R,
—NH—$(CH_2)_{mz}$—O—COO—R;
—NH—$(CH_2CH_2O)_m$—$CH_2CH_2$—O—COO—R,
—NH—$(CH_2)_{mz}$—S—R;
—NH—$(CH_2CH_2O)_m$—$CH_2CH_2$—S—R;
—NH—$(CH_2)_{mz}$—O—CO—CH($R^8$)—$CH_2$—S—R;
—NH—$(CH_2)_{mz}$—NHCO—CH($R^8$)—$CH_2$—S—R;
—NH—$(CH_2CH_2O)_m$—$CH_2CH_2$—NHCO—CH($R^8$)—$CH_2$—S—R;
—NH—$(CH_2CH_2O)_m$—$CH_2CH_2$—O—CO—CH($R^8$)—$CH_2$—S—R; and
—NH—$(CH_2)_{mz}$—S—S—R;
—Z—$NR^a$—Y—$NR^b$—COO—R, wherein mz is an integer of 2 to 30, $R^8$ is a hydrogen atom or a methyl group, and R and m are as already defined herein. The group is preferably a group selected from:

—NH—$(CH_2)_{mz}$—NH—COO—R;
—NH—$(CH_2CH_2O)_m$—$CH_2CH_2$—NH—COO—R; and
—NH—$(CH_2)_{mz}$—S—S—R, wherein mz, R, and m are as already defined herein.

In a preferred embodiment of the present invention, Z is a direct bond. Further, in one embodiment of the present invention, when Z is a peptide linker, $X^1$ is —$NR^b$—COO—R.

Specific examples of Y include —$CH_2CH_2$O—$CH_2CH_2$—S—S—$CH_2CH_2$O—$CH_2CH_2$—, —$(CH_2CH_2O)_2$—$CH_2CH_2$—S—S—$CH_2CH_2$O—$CH_2CH_2$—, —$CH_2CH_2$O—$CH_2CH_2$—S—S—$(CH_2CH_2O)_2$—$CH_2CH_2$—, and —$(CH_2CH_2O)_2$—$CH_2CH_2$—S—S—$(CH_2CH_2O)_2$—$CH_2CH_2$—.

$Y^a$ is preferably —$CH_2$— or —$CH_2$—$CH_2$—.

$Y^b$ is preferably —$CH_2$—$CH_2$—, —CH($CH_3$)$CH_2$—, 2-butene-1,4-diyl, hepta-2,4-diene-1,6-diyl, or octa-2,4,6-triene-1,8-diyl, more preferably —$CH_2$—$CH_2$— or —CH($CH_3$)$CH_2$—.

In one embodiment of the present invention, Z is a peptide linker represented by —NH—[CH(—$Z^a$)—$CONH]_{n-1}$—CH(—$Z^a$)—CO— wherein n is an integer of 2 to 30 and each $Z^a$ independently represents a substituent in an α-amino acid represented by $H_2N$—CH(—$Z^a$)—COOH. The peptide linker binds to a carboxy group of a glucuronic acid moiety at the N terminal, and binds to the group —N(—$R^a$)—Y—$X^1$ at the C terminal. Examples of an amino acid that can be used as an amino acid residue of the peptide linker include natural amino acids (L-amino acids), such as alanine, arginine, asparagine (Asn), aspartic acid, cysteine, glutamine, glutamic acid, glycin (Gly), histidine, isoleucine, leucine (Leu), lysine, methionine, phenylalanine (Phe), proline, serine, threonine, tryptophan, tyrosine, and valine, and D-forms thereof, etc. Any α-amino acid, including synthesized amino acids, can be used. Specifically, examples of $Z^a$ include —$CH_3$, $H_2NC(NH)NH(CH_2)_3$—, $H_2NCOCH_2$—, etc. Further, n-Z may be the same or different. Although n is an integer of 2 to 30, n is preferably 2 to 10, more preferably 2 to 4. Examples of a preferred peptide linker include -Gly-Phe-Leu-Gly-, -Asn-Phe-Phe-, -Phe-Phe-, Phe-Gly-, etc.

Specific examples of the group —Z—N($R^a$)Y—$X^1$ include —NH—$(CH_2)_2$—NH—CO-cholesteryl, —NH—$(CH_2)_4$—NH—$(CH_2)_3$—NH—$(CH_2)_3$—NH—COO-cholesteryl, —NH—$(CH_2)_3$—NH—$(CH_2)_4$—NH—$(CH_2)_3$—NH—COO-cholesteryl, —NH—$(CH_2)_4$—NH—$(CH_2)_3$—NH—COO-cholesteryl, —NH—$(CH_2)_4$—N(—$(CH_2)_3$—$NH_2$)—COO-cholesteryl, —NH—$(CH_2)_3$—NH—$(CH_2)_4$—N(—$(CH_2)_3$—$NH_2$)—COO-cholesteryl, —NH—$(CH_2)_3$—NH—$(CH_2)_4$—N(—$(CH_2)_3$—NH—$(CH_2)_3$—$NH_2$)—COO-cholesteryl, —NH—$(CH_2)_3$—NH—$(CH_2)_4$—N(—$(CH_2)_3$—$NH_2$)—CO—NH-cholesteryl, —NH—$(CH_2)_3$—NH—$(CH_2)_4$—N(—$(CH_2)_3$—$NH_2$)—CO-cholesteryl, —NH—$(CH_2)_3$—NH—$(CH_2)_4$—N(—$(CH_2)_3$—$NH_2$)-cholesteryl, etc. In a preferred embodiment of the group —Z—N($R^a$)Y—$X^1$, each of $R^a$, $R^b$, and $R^c$ is a hydrogen atom, Y is linear $C_{2-30}$ alkylene or —$(CH_2CH_2O)_m$—$CH_2CH_2$—, $Y^a$ is linear $C_{1-5}$ alkylene, or $Y^b$ is linear $C_{2-8}$ alkylene or linear $C_{2-8}$ alkenylene.

In another aspect, the present invention provides a hyaluronic acid derivative comprising a repeating unit represented by the formula (I) and a repeating unit represented by the formula (II):

[Formula 3]

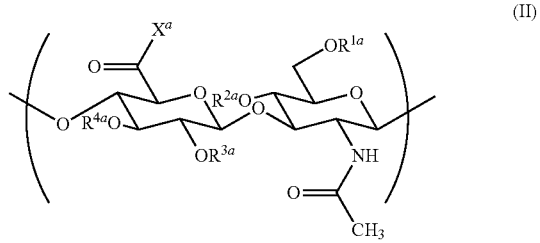

(II)

wherein $R^{1a}$, $R^{2a}$, $R^{3a}$, and $R^{4a}$ are each independently selected from a hydrogen atom, $C_{1-6}$ alkyl, formyl, and $C_{1-6}$ alkylcarbonyl; and $X^a$ is selected from hydroxy and —$O^-Q^+$, wherein $Q^+$ is a counter cation. In a case where the hyaluronic acid derivative of the present invention comprises two or more repeating units each represented by the formula (II), the repeating units may be the same or different. In one embodiment, the present invention provides a hyaluronic acid derivative substantially comprising a repeating unit(s) represented by the formula (I) and a repeating unit(s) represented by the formula (II).

$Q^+$ is not limited in any way as long as it is a counter action which forms a salt in water with a carboxy group. In a case of a valency of two or greater, $Q^+$ forms salts with a plurality of carboxy groups according to the valency. Examples of a counter cation include metal ions such as lithium ion, sodium ion, rubidium ion, cesium ion, magnesium ion, calcium ion, etc.; ammonium ion represented by the formula: $N^+R^jR^kR^lR^m$ (in the formula, $R^j$, $R^k$, $R^l$, and $R^m$ are each independently selected from a hydrogen atom and $C_{1-6}$ alkyl), etc.; sodium ion, potassium ion, and tetraalkylammonium ion (e.g., tetra(n-butyl)ammonium ion, etc.) are preferred. $R^j$, $R^k$, $R^l$, and $R^m$ are preferably the same group selected from $C_{1-6}$ alkyl, preferably n-butyl group.

Preferably, each of $R^1$, $R^2$, $R^3$, $R^4$, $R^{1a}$, $R^{2a}$, $R^{3a}$, and $R^{4a}$ is a hydrogen atom. Further, each of $R^a$ and $R^b$ is preferably a hydrogen atom.

In one embodiment of the present invention, the hyaluronic acid derivative substantially comprises a repeating unit(s) of the formula (I) and a repeating unit(s) of the formula (II). In the hyaluronic acid derivative, for example, 80% or more, preferably 90% or more, more preferably 95% or more, of disaccharide repeating units composed of D-glucuronic acid and N-acetylglucosamine are repeating units of the formula (I) or (II). In one embodiment of the present invention, the hyaluronic acid derivative consists of repeating units represented by the above formulas (I) and (II).

Y defined in the formula (I) may be, for example, $-(CH_2)_{na}-$ (wherein na is selected from 2 to 20, preferably 2 to 15, more preferably 2 to 12), preferably $-(CH_2)_2-$, $-(CH_2)_6-$, $-(CH_2)_8-$, or $-(CH_2)_{12}-$, more preferably $-(CH_2)_6-$. These Ys are preferred in terms of precipitate formation and stable dispersion described below.

In yet another aspect, the present invention provides the hyaluronic acid derivative defined herein which forms a particle upon association in water. Without being limited thereto, it is considered that spontaneous association occurs in water due to hydrophobic interaction of introduced hydrophobic groups to form a particle. Without being limited thereto, the particle size of the particle is, for example, 1 µm or smaller, preferably 500 nm or smaller, more preferably 200 nm or smaller, even more preferably 100 nm or smaller, further preferably 50 nm or smaller.

In yet another aspect, the present invention provides the hydrophobic group-introduced hyaluronic acid derivative defined herein wherein an introduction ratio of hydrophobic groups relative to disaccharide repeating units present in the derivative is 7 to 42%.

The introduction ratio of hydrophobic groups is calculated according to the following formula:

[Formula 4]

$$(\text{Introduction ratio of hydrophobic group(s)}) = \frac{(\text{Number of repeating units of hydrophobic group-introduced disaccharide})}{(\text{Number of disaccharide repeating units present})} \times 100$$

The "disaccharide repeating units present in the derivative" include a repeating unit of the formula (I) in which a carboxy group(s) is converted into an amide group(s) to introduce a hydrophobic group(s), and repeating units of the formulas (II), (III) and (IV) in which no hydrophobic group is introduced. The introduction ratio can be controlled by controlling reaction conditions, e.g., ratio of a reagent, and can be determined by, for example, NMR measurement or the like.

In one embodiment of the above aspect, the present invention provides the hydrophobic group-introduced hyaluronic acid derivative defined herein, wherein the introduction ratio of hydrophobic groups relative to disaccharide repeating units present in the derivative is 7 to 15%. In a case where the introduction ratio is in the above range, the hyaluronic acid derivative has a property that it aggregates significantly in a solution having a salt concentration of a predetermined level or more (e.g., at the physiological salt concentration) to form a precipitate. The hyaluronic acid derivative of the above group introduction ratio is complexed with a drug and then administered to the body (e.g. in the subcutis), whereby it may be used as a precipitation-type sustained-release formulation which makes use of its characteristic that it aggregates after being administered.

In another embodiment of the above aspect, the present invention provides the hydrophobic group-introduced hyaluronic acid derivative defined herein wherein the introduction ratio of hydrophobic groups relative to disaccharide repeating units present in the derivative is 18 to 42%. The hyaluronic acid derivative having an introduction ratio in the above range has a property that it forms a stable particle even in a solution having a salt concentration of a predetermined level or more (e.g., at the physiological salt concentration) and disperses stably in water. The hyaluronic acid derivative having the above introduction ratio is complexed with a drug and then administered to the body (e.g., into the vein), whereby it may be used as a formulation for sustained release in blood or a formulation for targeting a target tissue or cell.

In yet another embodiment of the above aspect, the present invention provides the hydrophobic group-introduced hyaluronic acid derivative defined herein wherein the introduction ratio of hydrophobic groups relative to disaccharide repeating units present in the derivative is 2 to 50%. The introduction ratio in the above range is preferable in terms of prolongation of residence time in blood, and is more preferably 8 to 35%, even more preferably 15 to 22%.

The hyaluronic acid derivative of the present invention comprising at least one repeating unit represented by the formula (I) is synthesized using as a raw material, preferably, hyaluronic acid or a derivative thereof substantially comprising a repeating unit(s) represented by the formula (II), more preferably, hyaluronic acid or a derivative thereof consisting of a repeating unit(s) represented by the formula (II). In terms of prolongation of residence time in blood, the weight-average molecular weight of the raw material is preferably 27 kilodaltons (kDa) or less, more preferably 18 kDa or less. The lower limit of the molecular weight may be 5 kDa or more. A preferred range of the molecular weight is 5 to 27 kDa, more preferably 5 to 18 kDa. In another aspect of the present invention, the hyaluronic acid derivative of the present invention can be produced using as a raw material hyaluronic acid or a derivative thereof having a weight-average molecular weight of 27 kDa or less and substantially comprising a repeating unit(s) represented by the formula (II). In one embodiment of the above aspect, the hyaluronic acid derivative of the present invention substantially comprises repeating units of the formulas (I) and (II).

The hyaluronic acid derivative of the present invention in which a hydrophobic group(s) is introduced at the above introduction ratio using hyaluronic acid or a derivative thereof having the above molecular weight has a property that the residence time in blood is prolonged significantly, compared with a case of using hyaluronic acid or a salt thereof having a weight-average molecular weight of greater than 27 kDa or a case of modifying with a group other than the above hydrophobic group. By use of the hyaluronic acid derivative produced using hyaluronic acid of the above molecular weight as a raw material, a systemic-administration type formulation, especially an intravenous-administration type formulation, for sustained release in blood which is excellent in residence time in blood and a formulation for targeting a target tissue or cell can be provided.

Y in the above formula (I) is preferably $-(CH_2)_{n1}-$ and $-(CH_2CH_2O)_{m1}-CH_2CH_2-$ (wherein n1 is an integer of 2 to 15, preferably 2 to 12, more preferably 2 to 6, and m1 is an integer of 1 to 4). Specifically, $-(CH_2)_2-$, $-(CH_2)_6-$, $-(CH_2)_{12}-$, and $-(CH_2CH_2O)_2-CH_2CH_2-$ are preferred, and $-(CH_2)_2-$, $-(CH_2)_6-$, and $-(CH_2CH_2O)_2-CH_2CH_2-$ are more preferred.

The hydrophobic group represented by X in the formula (I) is preferably $-NH-(CH_2)_2-NH-COO$-cholesteryl, $-NH-(CH_2)_6-NH-COO$-cholesteryl, $-NH-(CH_2)_{12}-NH-COO$-cholesteryl, and $-NH-(CH_2CH_2O)_2-CH_2CH_2-NH-COO$-cholesteryl, more preferably $-NH-(CH_2)_2-NH-COO$-cholesteryl, $-NH-(CH_2)_6-NH-COO$-cholesteryl, and $-NH-(CH_2CH_2O)_2-CH_2CH_2-NH-COO$-cholesteryl.

In another aspect, the present invention provides a hyaluronic acid derivative further comprising a repeating unit represented by the formula (III):

[Formula 5]

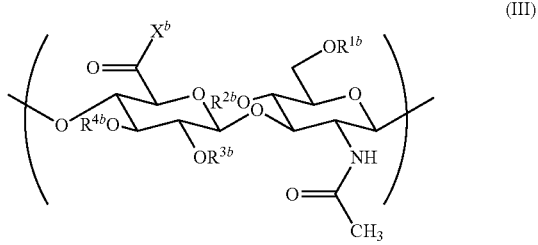

wherein
$R^{1b}$, $R^{2b}$, $R^{3b}$, and $R^{4b}$ are each independently selected from a hydrogen atom, $C_{1-6}$ alkyl, formyl, and $C_{1-6}$ alkylcarbonyl;
$X^b$ represents $-NR^e-Y^b-R^d$;
$R^e$ is a hydrogen atom or $C_{1-6}$ alkyl group;
$R^d$ is a hydrogen atom, $C_{1-6}$ alkyl group, or group $-CO-C(R^7)=CH_2$; and
$Y^b$ is $-CH_2-(CHR^5)_{l-2}-CH_2-NH-$, $-CH_2-(CHR^6)_{p-2}-CH_2-O-$, $-(CH_2)_j-S-$, $-CH_2-CH_2-(Y^3-CH_2-CH_2)_z-S-$, $-CH_2-CH_2-(Y^4-CH_2-CH_2)_t-NH-$, or $-CH_2-CH_2-(Y^5-CH_2-CH_2)_y-O-$, wherein l, p, and j are each independently an integer selected from 2 to 10, z, t, and y are each independently an integer selected from 1 to 200, $R^5$ and $R^6$ are each independently a hydrogen atom or hydroxy, $R^7$ is a hydrogen atom or methyl group, and $Y^3$, $Y^4$, and $Y^5$ are each independently an oxygen atom or $-NH-$. In one embodiment, the present invention provides a hyaluronic acid derivative substantially comprising repeating units represented by the above formulas (I), (II), and (III). In another embodiment, the present invention provides a hyaluronic acid derivative consisting of repeating units represented by the above formulas (I), (II), and (III). In terms of prolongation of residence time in blood, the hyaluronic acid derivative may be produced using as a raw material hyaluronic acid or a derivative thereof having a weight-average molecular weight of preferably 27 kDa or less, more preferably 18 kDa or less, and consisting of a repeating unit(s) represented by the formula (II). The lower limit of the weight-average molecular weight of the raw material may be 5 kDa or more. A preferred range of the molecular weight is 5 to 27 kDa, more preferably 5 to 18 kDa.

The percentage of repeating unit(s) represented by the formula (II) relative to repeating unit(s) of disaccharide present is preferably 50% or less, more preferably 30% or less, even more preferably 20% or less. The lower limit of the percentage may be 0% or more. Here, 50% or more of carboxy groups of the hyaluronic acid derivative are modified with $-Z-N(R^a)-Y-X^1$, $X^b$ and the like, but in a case where hyaluronic acid or a derivative thereof of the above weight-average molecular weight is used as a raw material and the percentage of repeating unit(s) represented by the formula (II) is set to a percentage specified above, the carboxy groups partially or mostly modified with the hydrophobic groups, whereby the hyaluronic acid derivative has a property that the residence time in blood is prolonged significantly compared with a case where the carboxy groups are modified only with groups other than the above hydrophobic groups. The introduction ratio of hydrophobic groups relative to repeating unit(s) of disaccharide present is preferably 2 to 70%, more preferably 5 to 35%, even more preferably 15 to 22%.

$X^b$s may be the same or different. For example, two amines, $H_2N-CH_2-CH_2-O-CO-C(CH_3)=CH_2$ (primary amine) and $H_2N-CH_2-CH_2-(O-CH_2-CH_2)_2-NH_2$ (secondary amine), may be condensed with a carboxy group(s) of a glucuronic acid moiety either simultaneously or successively. The hyaluronic acid derivative in which a double bond is introduced via the primary amine may be subjected to crosslinking reaction with a crosslinking agent (e.g., dithiothreitol: DTT) having mercapto groups at the both ends of an alkylene group. By performing crosslinking reaction, the hyaluronic acid derivative of the present invention can be formed into a gel. Further, the secondary amine, which is diamine, may be condensed with the carboxy group of the glucuronic acid moiety to thereby use the other one of the terminal amino groups to bind a drug. At this time, an amino group(s) remained without being used may be treated with, for example, dicarboxylic anhydride, such as succinic anhydride, maleic anhydride, glutaric anhydride, and adipic anhydride, or may be reacted with dicarboxylic acid, such as maleic acid, glutaric acid, and adipic acid, in the presence of a condensing agent to thereby convert the functional group at the terminal back to the carboxy group to thereby make the total charge anionic.

Alternatively, two amines, $H_2N-CH_2-CH_2-O-CO-C(CH_3)=CH_2$ (primary amine) and $H_2N-CH_2-CH_2-OH$ (secondary amine), may be condensed with a carboxy group of a glucuronic acid moiety either simultaneously or successively. The double bond introduced via the primary amine may also be subjected to crosslinking reaction as described above. Further, the hyaluronic acid derivative modified with the secondary amine is expected to have prolonged residence time in blood. Other exemplary crosslinking reactions include: crosslinking of a hyaluronic acid derivative modified to have amino groups (HA-AM) by condensation reaction with a crosslinking agent having succinimidyl esters or other imidoesters at the both ends of $C_{2-20}$ alkylene (e.g., bis[sulfosuccinimidyl]suberate ($BS_3$), ethylene glycol-bis[sulfosuccinimidyl]succinate (Sulfo-EGS), dimethyl adipimidate hydrochloride (DMA)); crosslinking of HA-AM with a crosslinking agent having formyl groups at the both ends of $C_{2-20}$ alkylene (e.g., glutaraldehyde); crosslinking of a hyaluronic acid derivative modified to have formyl groups (HA-ALD) with a crosslinking agent having amino groups at the both ends of $C_{2-20}$ alkylene (e.g., ethylenediamine (EDA)); crosslinking of a hyaluronic acid derivative modified to have mercapto groups (HA-SH) by oxidation reaction under oxidation conditions (e.g., in the presence of sodium tetrathionate (STT)); crosslinking of HA-SH by Michael addition reaction with a crosslinking agent having unsaturated bonds (e.g., maleimido (MAL) groups or methacryloyl groups) at the both ends of $C_{2-20}$ alkylene (e.g., 1,4-bis-maleimidobutane (BMB), ethylene dimethacrylate (EDMA)); crosslinking of a hyaluronic acid derivative modified to have an unsaturated bond such as an acryloyl group and a methacryloyl group by radical polymerization with various polymerization initiators (e.g., potassium peroxodisulfate (KPS)/N,N,N',N'-tetramethylethylenediamine (TEMED), Irgacure2959); and crosslinking in the presence of a diamine compound (e.g., EDA, 2,2'-(ethylenedioxy)bis(ethylenediamine)) by the action of a condensing agent (e.g., N,N'-carbonyldiimidazole (CDI), N,N'-dicyclohexylcarbodiimide (DCC), N-ethoxycarbonyl-2-ethoxy-1,2-dihydroquinoline (EEDQ), 4-(4,6-dimethoxy-1,3,5-triazine)-4-methylmorpholium chloride (DMT-MM), 2-benzotriazole-1,1,3,3-tetramethyluroniumtetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazole-1-yl-oxy-tris(dimethylamino) phosphonium hexafluorophosphate (BOP), 1-ethyl-3-(3-dimethylaminopropyl) carbodiimide (EDC), or N-hydroxysuccinimide (NHS)). The above crosslinkage formation may occur in the same molecule of the hyaluronic acid derivative or may occur between different molecules of the hyaluronic acid derivative.

In the chemically crosslinked structure of the gel of the hyaluronic acid derivative of the present invention, biodegradable elements may be used for crosslinking agents, crosslinkable groups introduced into polymers, binding mode, and so on. Without being limited thereto, for example, a group having an ester bond and a methacryloyl group may be used as a group subjected to crosslinking reaction. Further, a compound having an ester bond, such as Sulfo-EGS and EDMA, or a compound having a peptide spacer which is degraded by an enzyme in the body may be used as a crosslinking agent. Moreover, a gel crosslinked via disulfide bonds formed by oxidation of mercapto groups will be degraded in the body by disulfide exchange reaction or reduction reaction. Having a degradable chemically crosslinked structure enables control of the biodegradation rate of a gel, which in turn also enables control of the drug release rate.

An example of preferred $X^b$ is —$NR^i$—$(CH_2)_{n2}$—OH (in the formula, $R^i$ is a hydrogen atom, and n2 is an integer selected from 2 to 10); more preferably, —NH—$(CH_2)_2$—OH and —NH—$(CH_2)_3$—OH.

A hyaluronic acid derivative comprising a repeating unit(s) represented by the formula (III) is disclosed in WO2006/028110. A method of converting a carboxy group (—COOH) of hyaluronic acid into —$COX^a$ is described in the publication. The carboxy group may also be converted using a well-known condensation reaction.

In another aspect, the present invention provides the hyaluronic acid derivative defined herein, further comprising a repeating unit represented by the formula (IV):

[Formula 6]

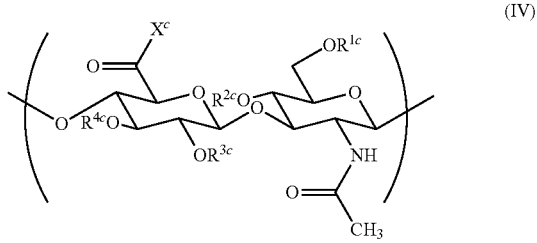

(IV)

wherein $R^{2c}$, $R^{3c}$, and $R^{4c}$ are each independently selected from a hydrogen atom, $C_{1-6}$ alkyl, formyl, and $C_{1-6}$ alkylcarbonyl;

$X^c$ is selected from hydroxy and —$O^-Q^+$, wherein $Q^+$ is a counter cation;

$R^{1c}$ is selected from
—CO—C($R^{21}$)=$CH_2$,
$CH_2CH(OH)$—$R^{22}$—$Y^1$,
—$CH(CH_2OH)$—$R^{22}$—$Y^1$,
—CONH—$R^{23}$—$Y^1$,
—CO—$R^{23}$—$Y^1$,
—CONH—$CH_2CH_2$—$(X^{21}$—$CH_2CH_2)_{n3}$—$Y^1$, and
—CO—$CH_2CH_2$—$(X^{21}$—$CH_2CH_2)_{n4}$—$Y^1$, $X^{21}$ is selected from O and S;
n3 and n4 each represent an integer of 1 to 50;
$Y^1$ is selected from amino, mercapto, formyl, and —$X^{14}$—CO—C($R^{18}$)=$CH_2$;
$R^{21}$ is selected from a hydrogen atom or $C_{1-6}$ alkyl;
$R^{22}$ and $R^{23}$ are each a divalent $C_{2-50}$ hydrocarbon group or divalent $C_{2-50}$ polyalkyleneoxy group, wherein the divalent $C_{2-50}$ hydrocarbon group may partially contain a polyalkyleneoxy moiety formed by insertion of 1 to 10 —O— atoms;
$X^{14}$ is selected from O and N($R^{19}$);
$R^{18}$ is a hydrogen atom or $C_{1-6}$ alkyl; and
$R^{19}$ is a hydrogen atom or $C_{1-6}$ alkyl.

In one embodiment of the above aspect, the hyaluronic acid derivative consists only of repeating units represented by the formulas (I), (II), and (IV), or consists only of repeating units represented by the formulas (I), (II), (III), and (IV).

In yet another aspect of the present invention, the hyaluronic acid derivative of the present invention is synthesized using as a raw material, preferably, hyaluronic acid or a derivative thereof having a weight-average molecular weight of 27 kDa or less and consisting of a repeating unit(s) represented by the formula (II). In one embodiment of the above aspect, the present invention provides a hyaluronic acid derivative substantially comprising repeating units represented by the formulas (I), (II), and (IV) or a hyaluronic acid derivative substantially comprising repeating units represented by the formulas (I), (II), (III), and (IV).

$R^{1c}$ is a substituent of hydroxy at position 6 of N-acetylglucosamine moiety, mainly a crosslinking group. Specific examples include —CO—C($CH_3$)=$CH_2$, —CO—CH=$CH_2$, —$CH_2CH(OH)$—$CH_2CH_2$—O—CO—C($CH_3$)=$CH_2$, —CONH—$CH_2CH_2$—O—CO—C($CH_3$)=$CH_2$, —CONH—$CH_2CH_2$—(O—$CH_2CH_2)_2$—O—CO—CH=$CH_2$, etc. The percentage of repeating units represented by the formula (IV) relative to disaccharide repeating units present is preferably 10 to 40%. A hyaluronic acid derivative comprising a repeating unit(s) represented by the formula (IV) is disclosed in WO2008/136536, and the conversion of hydroxy (—OH) in position 6 of N-acetylglucosamine moiety of hyaluronic acid into —$OR^{1c}$ can be carried out by reference to Examples 10 and 14 of WO2008/136536 (Patent Document 8) and JP 2005-298644 A and Biomacromolecules, Vol. 6, pp. 1829-1834, 2005 (Non-patent Document 9) cited in WO2008/136536. The conversion can also be carried out by well-known esterification and etherification reactions.

In yet another aspect, the present invention provides a pharmaceutical composition comprising as a carrier a hyaluronic acid derivative defined herein. An active ingredient contained in the pharmaceutical composition is not limited in any way, and examples include proteins and/or peptides, polysaccharides, nucleic acids, low-molecular-weight compounds, etc. In one embodiment of the above aspect, the present invention provides a pharmaceutical composition comprising a pharmacologically-active protein or peptide and, as a carrier, a hyaluronic acid derivative defined herein. The hyaluronic acid derivative of the present invention is characterized in that it forms a complex with a drug in water. The complex of the hyaluronic acid derivative and the drug thus formed may be either of a dispersible particle and a precipitate.

The dispersible particle can be used as a matrix for a systemic administration type formulation, especially an intravenous administration type formulation, for sustained release in blood, or for a formulation for targeting a target tissue or cell. The precipitate can be used as a matrix for a local administration type sustained-release formulation.

In another aspect, the present invention provides the hyaluronic acid derivative defined herein which spontaneously associates in an aqueous solution upon hydrophobic interaction of hydrophobic groups to form a complex with a drug present in the system. In one embodiment of the above aspect, the drug is a protein or peptide.

In another aspect, the present invention provides a hyaluronic acid derivative-drug conjugate in which at least one drug is conjugated to the hyaluronic acid derivative defined herein. In one embodiment of the above aspect, the drug(s) is a protein, peptide, nucleic acids, or low-molecular-weight compound.

In yet another aspect, the present invention provides a method for producing a pharmaceutical composition comprising the step of forming a complex of the hyaluronic acid derivative defined herein and a drug in water. In one embodiment of the above aspect, the present invention provides a method for producing a pharmaceutical composition, comprising:

(a) producing a hyaluronic acid derivative having a hydrophobic group defined herein;
(b) dissolving or dispersing the resulting hyaluronic acid derivative in an aqueous phase; and
(c) adding a drug to the resulting aqueous solution or dispersion of the hyaluronic acid derivative to form a drug-entrapped particle.

In a case where the pharmaceutical composition is a precipitate, the following step may be added:

(d) adding a salt substance to precipitate the drug-entrapped particle.

Each of the above steps may be carried out in a discontinuous phase such as a W/O emulsion and spray droplets. The particle formed in the aqueous phase in the step (c) or the precipitate obtained in the step (d) may be dried (by, for example, spray drying, lyophilization or the like) and solidified and, when necessary, grinding, drying, washing and the like may be carried out to obtain an intended pharmaceutical composition as a solid.

Advantageous Effect of Invention

The hyaluronic acid derivative of the present invention enables the provision of sustained-release formulations encapsulating a large amount of drugs, particularly pharmacologically active proteins or peptides, while retaining their biological activity. Further, the hyaluronic acid derivative is advantageous in terms of safety; the hyaluronic acid derivative is advantageous especially as a carrier for a pharmaceutical formulation. Furthermore, by conjugating a drug with the hyaluronic acid derivative of the present invention to form a conjugate, the residence time in blood of the drug can be prolonged.

BRIEF DESCRIPTION OF DRAWINGS

FIG. 10-1 is one example of a chart showing results of size exclusion chromatography of the HA derivative obtained in Example 2-3-1 to observe from changes in retention time formation of an association product of the HA derivative (Example 3).

FIG. 10-2 is one example of a chart showing results of size exclusion chromatography of the HA derivative obtained in Example 2-3-2 to observe from changes in retention time formation of an association product of the HA derivative (Example 3).

FIG. 10-3 is one example of a chart showing results of size exclusion chromatography of the HA derivative obtained in Example 2-3-4 to observe from changes in retention time formation of an association product of the HA derivative (Example 3).

FIG. 10-4 is one example of a chart showing results of size exclusion chromatography of the HA derivative obtained in Example 2-3-3 to observe from changes in retention time formation of association products of the HA derivative (Example 3).

FIG. 11-1 is one example of a chart showing results of hydroxypropyl-β-cyclodextrin (HP-β-CD)-added size exclusion chromatography of the sample obtained in Example 2-3-1 to observe from changes in retention time decay of an association product of the HA derivative (Example 4).

FIG. 11-2 is one example of a chart showing results of hydroxypropyl-β-cyclodextrin (HP-β-CD)-added size exclusion chromatography of the sample obtained in Example 2-3-2 to observe from changes in retention time decay of an association product of the HA derivative (Example 4).

FIG. 11-3 is one example of a chart showing results of hydroxypropyl-β-cyclodextrin (HP-β-CD)-added size exclusion chromatography of the sample obtained in Example 2-3-4 to observe from changes in retention time decay of an association product of the HA derivative (Example 4).

FIG. 11-4 is one example of a chart showing results of hydroxypropyl-β-cyclodextrin (HP-β-CD)-added size exclusion chromatography of the sample obtained in Example 2-3-3 to observe from changes in retention time decay of an association product of the HA derivative (Example 4).

FIG. 12 is one example of a chart showing the results of size exclusion chromatography carried out in Examples 5 and 6.

FIG. 22-1 is a graph showing the results of preparation of a complex of a cholesteryl group-introduced HA derivative and lysozyme in Example 18-1; the vertical axis represents a value of (weight of Lys in the complex/weight of HA derivative)×100 (complexation %), and the horizontal axis represents an introduction ratio (%) of a hydrophobic group(s) per unit.

FIG. 22-2 is a graph showing the results of preparation of a complex of a cholesteryl group-introduced HA derivative and exendin-4 in Example 18-2; the vertical axis represents a value of (weight of Ex-4 in the complex/weight of HA derivative)×100 (complexation %), and the horizontal axis represents an introduction ratio (%) of a hydrophobic group(s) per unit.

FIG. 22-3 is a graph showing the results of preparation of a complex of a cholesteryl group-introduced HA derivative and human growth hormone in Example 18-3; the vertical axis represents a value of (weight of hGH in the complex/weight of HA derivative)×100 (complexation %), and the horizontal axis represents an introduction ratio (%) of a hydrophobic group(s) per unit.

FIG. 22-4 is a graph showing the results of preparation of a complex of a cholesteryl group-introduced HA derivative and erythropoietin in Example 18-4; the vertical axis represents a value of (weight of EPO in the complex/weight of HA derivative)×100 (complexation %), and the horizontal axis represents an introduction ratio of hydrophobic groups per unit.

FIG. 23-1 is one example of a graph showing the release of erythropoietin from the cholesteryl group-introduced HA derivative in a bovine serum albumin (20 mg/mL) solution; the vertical axis represents an amount of erythropoietin released, and the horizontal axis represents an elapsed time.

FIG. 23-2 is one example of a graph showing the release of erythropoietin from the cholesteryl group-introduced HA derivative (HA-C$_{12}$-Chol-7%) in bovine serum albumin solutions of different concentrations; the vertical axis represents an amount of erythropoietin released, and the horizontal axis represents an elapsed time.

FIG. 26-1 is a graph showing both the time course of plasma concentration of hGH up to 96 hours from the time of administration of the hGH/HA derivative complexes of Samples 20-1 to 20-4 of Table 23-1 and the time course of plasma concentration of hGH solutions of Comparative Example 1.

FIG. 26-2 is a graph showing both the time course of plasma concentration of hGH up to 24 hours from the time of administration of hGH/HA derivative complexes of Samples 20-1 to 20-4 of Table 23-1 and the time course of plasma concentration of hGH solutions of Comparative Example 1.

FIG. 27-1 is a graph showing both the time course of plasma concentration of hGH up to 96 hours from the time of administration of the hGH/HA derivative complexes of Samples 20-4 to 20-6 of Table 23-1 and the time course of plasma concentration of hGH solutions of Comparative Example 1.

FIG. 27-2 is a graph showing the time course of plasma concentration up to 24 hours from the time of administration of hGH/HA derivative complexes of Samples 20-4 to 20-6 of Table 23-1 and the time course of plasma concentration of hGH solutions of Comparative Example 1.

FIG. 30-1 is a graph showing the time course of plasma concentration of fluorescence-labeled HA derivatives prepared in Examples 12 and 15 in rats administered with the fluorescence-labeled HA derivatives.

FIG. 30-2 is a graph showing a relation between the extrapolated area under the plasma concentration-time curve (AUC∞) of Table 28 and the molecular weight. The vertical axis represents AUC∞, and the horizontal axis represents a molecular weight of the raw material HA-Na.

FIG. 32-1 is a graph showing the time course of plasma concentration of fluorescence-labeled HA derivatives of Samples 21-2 and 21-10 of Table 31 in rats administered with the fluorescence-labeled HA derivatives.

FIG. 32-2 is a graph showing the time course of plasma concentration of fluorescence-labeled HA derivatives of Samples 21-5, 21-11, and 21-12 of Table 31 in rats administered with the fluorescence-labeled HA derivatives.

FIG. 34-1 is a graph showing the time course of plasma concentration of fluorescence-labeled HA derivatives (10 k HA-C$_6$-Chol-22%/FL) of Table 35 in rats subcutaneously and intravenously administered with the fluorescence-labeled HA derivatives.

FIG. 34-2 is a graph showing the time course of plasma concentration of fluorescence-labeled HA derivatives (10 k HA-C$_6$-Chol-19%/C$_2$—OH/FL-95%) of Table 35 in rats subcutaneously and intravenously administered with the fluorescence-labeled HA derivatives.

FIG. 35-1 is a graph showing the results of experiment demonstrating the effect of preadministration of sodium hyaluronate on the time course of plasma concentration of fluorescence-labeled HA derivatives (10 k HA-C$_6$-Chol- 22%/FL) of Table 37 in rats intravenously administered with the fluorescence-labeled HA derivatives.

FIG. 35-2 is a graph showing the results of experiment demonstrating the effect of preadministration of sodium hyaluronate on the time course of plasma concentration of fluorescence-labeled HA derivatives (50 k HA-C$_6$-Chol-27%/FL) of Table 34 in rats subcutaneously and intravenously administered with the fluorescence-labeled HA derivatives.

FIG. 36-1 is a chromatogram showing the results of SEC analysis of Sample 21-2 (sample from 5 minutes to 2 hours) after the measurement in Example 21-1.

FIG. 36-2 is a chromatogram showing the results of SEC analysis of Sample 21-2 (sample from Day 1 to Day 4) after the measurement in Example 21-1.

FIG. 37-1 is a chromatogram showing the results of SEC analysis of a urine sample obtained from the rat (Comparative Sample 2-2) used in the pharmacokinetic study of Comparative Example 2-4.

FIG. 37-2 is a chromatogram showing the results of SEC analysis of a urine sample obtained from the rat (Sample 21-2) used in the pharmacokinetic study of Example 21-1.

FIG. 37-3 is a chromatogram showing the results of SEC analysis of a urine sample obtained from the rat (Sample 21-5) used in the pharmacokinetic study of Example 21-1.

FIG. 37-4 is a chromatogram showing the results of SEC analysis of a urine sample obtained from the rat (Sample 21-6) used in the pharmacokinetic study of Example 21-1.

FIG. 37-5 is a chromatogram showing the results of SEC analysis of a urine sample obtained from the rat (Sample 21-7) used in the pharmacokinetic study of Example 21-1.

DESCRIPTION OF EMBODIMENT

Figure 1:
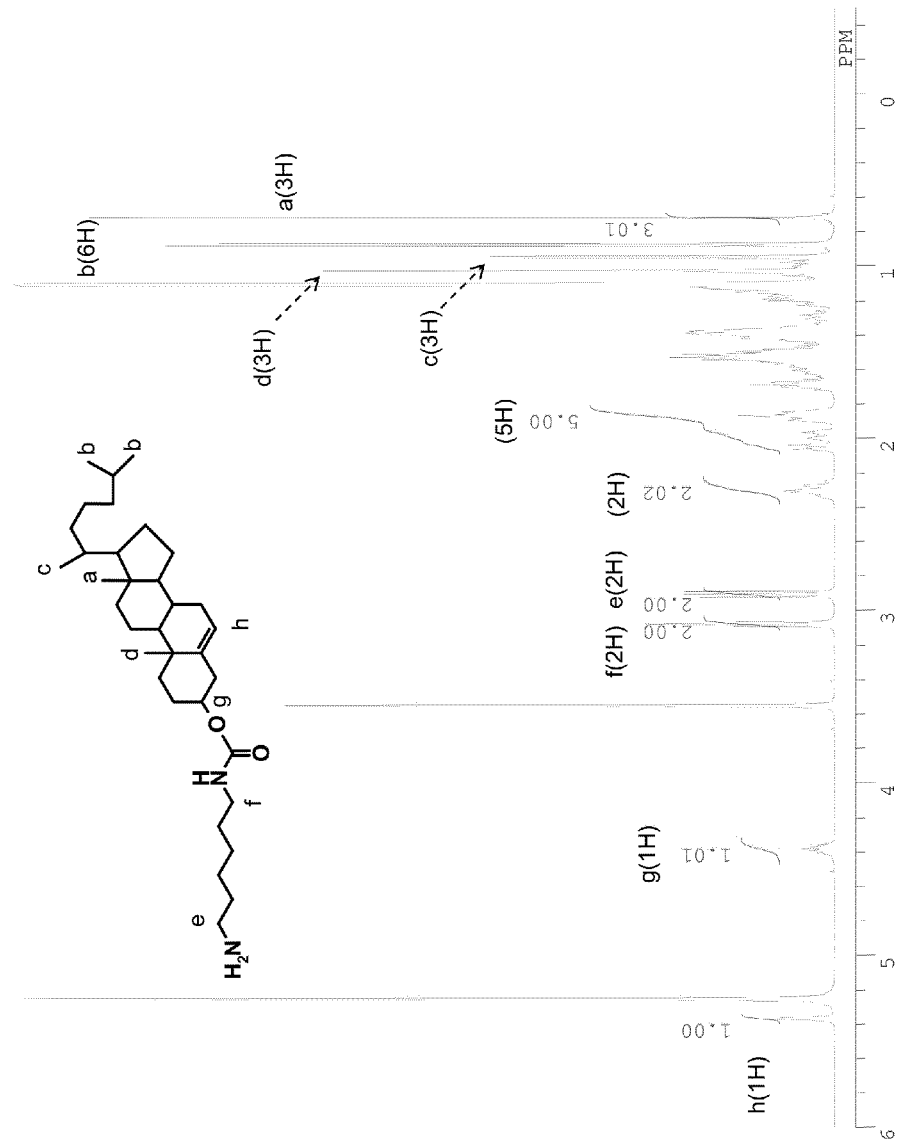
FIG. 1 is one example of the $^1$H-NMR spectrum of cholesteryl 6-aminohexylcarbamate hydrochloride prepared in Example 1-1.

The present invention will be further described in more detail below.

As used herein, the term "steryl group" is not limited in any way as long as it is a group having a steroid skeleton. Specific examples of steroid include cholesterol, cholestanol, campestanol, ergostanol, stigmastanol, coprostanol, stigmasterol, sitosterol, lanosterol, ergosterol, simiarenol, bile acid, testosterone, estradiol, progesterone, cortisol, cortisone, aldosterone, corticosterone, deoxycorticosterone, etc. Examples of a steryl group include a cholesteryl group, a stigmasteryl group, a lanosteryl group, an ergosteryl group, etc., preferably a cholesteryl group (especially, cholesta-5-ene-3β-yl group).

As used herein, the term "$C_{1-20}$ alkyl" is intended to mean a linear or branched alkyl group containing 1 to 20 carbon atoms. Examples include "$C_{1-4}$ alkyl" such as methyl, ethyl, n-propyl, i-propyl, n-butyl, s-butyl, i-butyl, and t-butyl, as well as n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 1-ethylbutyl, and 2-ethylbutyl. The $C_{1-20}$ alkyl includes $C_{1-12}$ alkyl containing 1 to 12 carbon atoms and a $C_{1-6}$ alkyl group containing 1 to 6 carbon atoms.

As used herein, the term "$C_{1-6}$ alkylcarbonyl" is intended to mean an alkylcarbonyl group in which an alkyl moiety is $C_{1-6}$ alkyl described above, and examples include "$C_{1-4}$ alkylcarbonyl" such as acetyl, propionyl, n-propylcarbonyl, i-propylcarbonyl, n-butylcarbonyl, s-butylcarbonyl, i-butylcarbonyl, t-butylcarbonyl, etc.

As used herein, the term "amino $C_{2-20}$ alkyl" is intended to mean a linear or branched alkyl having an amino group as a substituent and containing 2 to 20 carbon atoms. For example, the amino group may be positioned on a carbon atom at a terminal of the alkyl group.

As used herein, the term "hydroxy $C_{2-20}$ alkyl" is intended to mean a linear or branched alkyl group having a hydroxy group as a substituent and containing 2 to 20 carbon atoms. For example, the hydroxy group may be positioned on a carbon atom at a terminal of the alkyl group.

As used herein, the term "$C_{2-30}$ alkylene" is intended to mean a linear or branched divalent saturated hydrocarbon group having 2 to 30 carbon atoms. Examples include ethylene, propylene, and the like as well as $C_{2-20}$ alkylene, $C_{2-8}$ alkylene, the group —(CH$_2$)$_n$— (wherein n is 2 to 30, preferably 2 to 20, more preferably 2 to 15), etc.

As used herein, the term "$C_{1-30}$ alkylene" is intended to mean a linear or branched divalent saturated hydrocarbon group having 1 to 5 carbon atoms. Examples include methylene, ethylene, propylene, etc.

As used herein, the term "$C_{2-8}$ alkenylene" is intended to mean a linear or branched divalent saturated hydrocarbon group containing 2 to 8 carbon atoms and including one or more double bonds. Examples include —CH=CH—, —C(CH$_3$)=CH—, 2-butene-1,4-diyl, hepta-2,4-diene-1,6-diyl, octa-2,4,6-triene-1,8-diyl, etc. In a case where geometrical isomerism exists, their isomers and mixtures thereof are also included.

As used herein, the term "divalent $C_{2-50}$ hydrocarbon group" is not limited in any way, and examples include linear, branched, cyclic and partially cyclic alkylene, alkenylene and alkynylene groups containing 2 to 50 carbon atoms. This group may be a divalent aromatic ring or may contain an aromatic ring in a part of its structure.

As used herein, the term "divalent $C_{2-50}$ polyalkyleneoxy" is not limited in any way, and the alkylene group as a repeating unit may be either linear or branched. Examples of such a "divalent $C_{2-50}$ polyalkyleneoxy" include a divalent $C_{2-50}$ polyethyleneoxy group, a $C_{3-48}$ polypropyleneoxy group, a $C_{3-48}$ polybutyleneoxy group, etc. This group may be linked via an oxygen atom or a carbon atom to another group. By way of example, the $C_{2-50}$ polyethyleneoxy group includes —O(CH$_2$CH$_2$O)$_{l\text{-}25}$—, —(CH$_2$CH$_2$O)$_{l\text{-}25}$—, —(OCH$_2$CH$_2$)$_{l\text{-}25}$—, —(CH$_2$CH$_2$O)$_{l\text{-}24}$—(CH$_2$CH$_2$)—, etc.

As used herein, the term "salt substance" is not limited in any way as long as it is a water-soluble inorganic substance. Examples include calcium salts such as calcium chloride and calcium phosphate, magnesium salts such as magnesium sulfate and magnesium chloride, aluminum salts such as aluminum sulfate and aluminum chloride, potassium salts such as potassium sulfate, potassium carbonate, potassium nitrate, potassium chloride, potassium bromide, and potassium iodide, sodium salts such as sodium acid carbonate, sodium carbonate, sodium sulfate, sodium nitrate, sodium chloride, sodium bromide, sodium iodide, sodium silicate, trisodium phosphate, disodium phosphate, sodium borate, sodium acetate, and sodium citrate, and lithium salts such as lithium chloride, lithium bromide, lithium iodide, and lithium carbonate; preferably, sodium chloride, trisodium phosphate, disodium phosphate, potassium chloride, calcium chloride, magnesium chloride, etc.

As raw materials for producing the hyaluronic acid derivative of the present invention, hyaluronic acid or a salt or derivative thereof can be used. Examples of a hyaluronic acid salt include alkali metal salts such as a sodium salt, a potassium salt and a lithium salt, and particularly preferred is a sodium salt which is widely used for pharmaceutical purposes. HA or a pharmaceutically acceptable salt thereof may be prepared in various known manners, for example, by extraction from a biological raw material such as cock's comb or swine hypodermis or by biological fermentation. Alternatively, a commercially available product may be purchased (e.g., from Denki Kagaku Kogyo Kabushiki Kaisha, Japan, Shiseido Co., Ltd., Japan, Seikagaku Corporation, Japan, R&D systems, Inc. or others) and obtained for this purpose.

Although there is no particular limitation on the molecular weight of the hyaluronic acid derivative of the present invention, hyaluronic acid having a high viscosity and a high molecular weight is preferred in a case of expecting the sustained-release function arising from diffusion retardation at locally administered site, while hyaluronic acid having a low viscosity and a low molecular weight is preferred in a case where the final dosage form is a solution formulation. For this reason, the molecular weight of the hyaluronic acid derivative is preferably 1 kDa to 1,000 kDa, and more preferably 10 kDa to 300 kDa. In general, the molecular weight of an intended product can be adjusted by using a raw material having a corresponding molecular weight. In terms of precipitate formation and stable dispersion described above, the molecular weight of the raw material of the hyaluronic acid derivative of the present invention is preferably 10 kDa to 500 kDa, more preferably 27 kDa to 230 kDa, even more preferably 50 kDa to 230 kDa, further preferably 50 kDa to 99 kDa. In terms of prolongation of residence time in blood, the molecular weight of the raw material of the hyaluronic acid derivative of the present invention is preferably 5 kDa to 27 kDa, more preferably 5 kDa to 18 kDa. In terms of gel formation, the molecular weight of the raw material of the hyaluronic acid derivative of the present invention is preferably 5 kDa to 300 kDa, more preferably 5 kDa to 50 kDa, even more preferably 5 kDa to 27 kDa.

In general, it is difficult to obtain hyaluronic acid or a derivative thereof as a single product and, thus, its molecular weight is calculated as a number-average molecular weight or as a weight-average molecular weight. In the present invention, the molecular weight is calculated as a weight-average molecular weight. It is to be noted that, as a method of measuring the weight-average molecular weight, various types of known methods such as the light scattering method, the osmotic pressure method, or the viscosity method, described in "Essential Kobunshi Kagaku (Essential Polymer Chemistry)" written by Seiichi Nakahama, (published by Kodansha Ltd., ISBN4-06-153310-X), can be applied. The viscosity-average molecular weight mentioned herein can also be measured by methods generally applied in the technical field to which the present invention pertains, such as the use of a Ubbelohde viscometer. In a case of using hyaluronic acid and a derivative thereof that are commercially available with their molecular weight being specified, the numerical value specified may be used as a molecular weight.

In the hyaluronic acid derivative of the present invention, a hydrophobic group(s) is introduced by conversion of a carboxy group(s) of glucuronic acid, which is one of the disaccharides constituting the repeating units, into amide. By adjusting the degree of modification of the hyaluronic acid derivative, pharmacokinetics in the body of a formulation produced using the derivative can be controlled.

In a case where the modification ratio of carboxy groups of the glucuronic acid moiety of the hyaluronic acid derivative is low, e.g., a case where 50% or less of carboxy groups present are modified, the effect of targeting a hyaluronic acid receptor including CD44 overexpressed in inflamed sites and tumor sites, liver, which is a major metabolic system of hyaluronic acid, and a lymphatic system can be expected. For example, targeting of inflamed synovial cells of patients with osteoarthritis or rheumatism, uptake into cells by receptor-mediated endocytosis, and release of a drug in cells to cure inflammation can be expected.

Further, in a case where the modification ratio of carboxy groups of the glucuronic acid moiety of the hyaluronic acid derivative is high, binding to the hyaluronic acid receptors is inhibited, and the hyaluronic acid derivative becomes a drug carrier having stealth effect in the body and long retention time. In this case, the effect of targeting tumor cells using the EPR effect (Enhanced Permeation and Retention effect) can also be expected. Furthermore, by introducing a target element into the hyaluronic acid derivative, it becomes possible to target each organ and cell. Examples of a target element include a target tissue-specific peptide, antibody, fragmented antibody, aptamer, RGD peptide for cancer cells, folic acid, anisamide, transferrin, galactose for liver, tocopherol, etc.

Note that in the case of gelling, the modification ratio of carboxy groups of the glucuronic acid moiety of the hyaluronic acid derivative may be low or high.

In terms of formation of a complex with a drug, preferably a protein, the ratio of modification of carboxy groups of the glucuronic acid moiety of the hyaluronic acid derivative with a hydrophobic group(s), i.e., introduction ratio of hydrophobic groups, is preferably 2 to 60%, more preferably 2 to 50%, even more preferably 2 to 40%, further preferably 5 to 20%, even further preferably 7 to 15%. In terms of precipitate formation described above, the ratio is preferably 7 to 15%. In terms of stable dispersion, the ratio is preferably 18 to 42%. In terms of prolongation of residence time in blood, the ratio is preferably 2 to 50%, more preferably 8 to 35%, even more preferably 15 to 22%. In terms of gel formation, the ratio is preferably 2 to 30%, more preferably 2 to 22%, even more preferably 5 to 22%, further preferably 7 to 22%.

In terms of precipitate formation described above, the combination of the molecular weight of the raw material of the hyaluronic acid derivative of the present invention and the introduction ratio of hydrophobic groups is preferably 27 kDa to 230 kDa and 7 to 15%, more preferably 50 kDa to 230 kDa and 7 to 15%, even more preferably 50 kDa to 99 kDa and 7 to 15%. In terms of stable dispersion, the combination is preferably 27 kDa to 230 kDa and 18 to 42%, more preferably 50 kDa to 230 kDa and 18 to 42%, even more preferably 50 kDa to 99 kDa and 18 to 42%. In terms of prolongation of residence time in blood, the combination is preferably 5 kDa to 27 kDa and 2 to 50%, more preferably 5 kDa to 27 kDa and 8 to 35%, even more preferably 5 kDa to 18 kDa and 8 to 35%, further preferably 5 kDa to 18 kDa and 8 to 35%, even further preferably 5 kDa to 18 kDa and 15 to 22%. In terms of gel formation, the combination is preferably 5 kDa to 300 kDa and 2 to 30%, more preferably 5 kDa to 50 kDa and 2 to 22%, even more preferably 5 kDa to 27 kDa and 2 to 22%, further preferably 5 kDa to 27 kDa and 7 to 22%.

Examples of a method of converting carboxy groups of glucuronic acid into amides to introduce a hydrophobic group(s) to thereby produce the hyaluronic acid derivative of the present invention include a method in which hyaluronic acid or a derivative thereof, preferably hyaluronic acid or a derivative thereof consisting of a repeating unit(s) represented by the formula (II), as a raw material is ion-exchanged into a tetraalkylammonium salt (e.g., tetrabutylammonium (TBA) salt), and the hyaluronic acid salt is reacted in a solvent in the presence of an appropriate condensing agent with an amine in which a hydrophobic group represented by the formula $HNR^a$—Y—$NR^b$—R,  $NHR^a$—Y—$NR^b$—COO—R, $HNR^a$—Y—$NR^b$—COO—R, $HNR^a$—Y—$NR^b$—CO—R, $HNR^a$—Y—$NR^b$—CO—$NR^c$—R, $HNR^a$—Y—COO—R, $HNR^a$—Y—O—COO—R, $HNR^a$—Y—S—R, $HNR^a$—Y—CO—$Y^a$—S—R, $HNR^a$—Y—O—CO—$Y^b$—S—R, $HNR^a$—Y—$NR^b$—CO—$Y^b$—S—R, $HNR^a$—Y—S—S—R, or —Z—$NR^a$—Y—$NR^b$—COO—R (in the formula, $R^a$, $R^b$, Rc, Y, $Y^a$, $Y^b$, Z, and R are as already defined herein) is introduced.

There is no particular limitation on the condensing agent that can be used in the above reaction, and examples include 4-(4,6-dimethoxy-1,3,5-triazine)-4-methylmorpholium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazole-1-yl-oxy-tris (dimethylamino) phosphonium hexafluorophosphate (BOP), 1-ethyl-3-(3-dimethylaminopropyl) carbodiimide (EDC), N-hydroxysuccinimide (NHS), etc.

Without being limited thereto, DMT-MM is preferred in that the reaction is developed at high efficiency even in a mixed solvent of water and an organic solvent. Further, use of DMT-MM as a condensing agent enables highly-selective formation of an amide bond by an amino group and a carboxy group while inhibiting formation of an ester bond in a system in which a large number of hydroxy groups are present. The use of this condensing agent prevents, for example, reaction of an alcohol used as a solvent with a carboxy group of the hyaluronic acid moiety, as well as formation of an undesired crosslinkage due to intermolecular or intramolecular bonding of carboxy and hydroxy groups that are present simultaneously in the hyaluronic acid moiety.

Examples of a solvent used in the introduction reaction of a hydrophobic group(s) include water, DMSO, methanol, ethanol, propanol, butanol, acetonitrile, DMF, THF, dichloromethane, chloroform, hexane, diethyl ether, ethyl acetate, and a mixed solvent thereof. For example, in a case of where the introduction ratio of hydrophobic groups is 18 to 42%, it is preferable to use DMSO alone as a reaction solvent in terms of inhibition of precipitation of particles formed after introduction of a hydrophobic group(s) and dispersibility in the solvent.

Alternatively, hyaluronic acid or a derivative thereof as a raw material may be ion-exchanged into a tetraalkylammonium salt (e.g., tetrabutylammonium (TBA) salt), and the hyaluronic acid salt may be reacted with a spacer moiety in a solvent in the presence of an appropriate condensing agent (at this time, protection and deprotection reactions may be conducted as necessary) to convert a carboxy group (—COOH) of the raw material hyaluronic acid or a derivative thereof and thereafter reacted with an appropriate reagent. Examples of a combination of the group induced from the carboxy group and the reaction reagent are as shown below:

—$CONR^a$—Y—$NR^b$H+Hal-R,
—$CONR^a$—Y—$NR^b$H+Hal-COOR,
—$CONR^a$—Y—$NR^b$H+HOCO—R,
—$CONR^a$—Y—$NR^b$H+Hal-CO—R,
—$CONR^a$—Y—$NR^b$—COOH+$HNR^c$—R,
—$CONR^a$—Y—$NR^b$—CO—$NR^c$H+Hal-R,
—$CONR^a$—Y—$NR^b$H+HOCO—$NR^c$—R,
—$CONR^a$—Y—$NR^b$H+Hal-CO—$NR^c$—R,
—$CONR^a$—Y—COOH+HO—R,
—$CONR^a$—Y—OH+Hal-COO—R,
—$CONR^a$—Y—OCOOH+HO—R,
—$CONR^a$—Y—OCOOH+Hal-R,
—$CONR^a$—Y—OCO-Hal+HO—R,
—$CONR^a$—Y—SH+Hal-R,
—$CONR^a$—Y-Hal+HS—R,
—$CONR^a$—Y—CO—$Y^a$-Hal+HS—R
—$CONR^a$—Y—CO—$Y^a$—SH+Hal-R,
—$CONR^a$—Y—O—CO—CH=$CH_2$+HS—R,
—$CONR^a$—Y—$NR^b$—CO—CH($CH_3$)=$CH_2$+HS—R,
—$CONR^a$—Y—SH+HS—R,
—COZ—OH+$HNR^a$—Y—$NR^b$—COO—R, and
—COZ—$NR^a$—Y—$NR^b$H+Hal-COO—R wherein $R^a$, $R^b$, $R^c$, Y, $Y^a$, $Y^b$, and Z are as already defined herein, and Hal represents a halogen atom selected from a fluorine atom, a chlorine atom, a bromine atom, and iodine).

Examples of a reaction mode include nucleophilic addition reactions, such as dehydrohalogenation reaction, condensation reaction, dehydration reaction, and Michael addition, oxidative disulfide formation reaction, etc. These are well-known reactions, and a person skilled in the art may select an appropriate reaction, find suitable reaction conditions, and carry out the reaction under the reaction conditions. In a case where the conversion product or reaction product has a carboxy group, it may be converted into N-hydroxysuccinimide (hereinafter also referred to as "NHS") ester and then reacted.

Another example is a method in which a carboxy group of hyaluronic acid or a derivative thereof as a raw material is reacted with 2-aminoethyl 2-pyridyl disulfide to thereby prepare a hyaluronic acid derivative in which a spacer having a mercapto group modified with a leaving group at a terminal is introduced, and the hyaluronic acid derivative is subjected to nucleophilic substitution reaction with thiocholesterol to form a disulfide bond.

Another example is a method in which hyaluronic acid or a derivative thereof having a carboxy group in which a part of a spacer is introduced and a steryl group in which a part of a spacer is introduced are prepared and then reacted together. Specific examples are partially described above. Another example in a case where —S—S— is inserted in Y is a method in which a hyaluronic acid derivative in which a spacer having a mercapto group at a terminal is introduced into a carboxy group of hyaluronic acid and a steryl group in which a spacer having a mercapto group at a terminal is introduced are prepared and then oxidatively reacted together to form a disulfide bond. At this time, one mercapto group may be reacted with 2-mercaptopyridine to form a disulfide and thereafter substituted with another mercapto group.

After the hyaluronic acid derivative of the present invention is prepared, another substituent may be introduced. For example, 0.1 to 99.5%, preferably 10 to 40%, of carboxy groups in a hyaluronic acid derivative substantially comprising repeating units represented by the formulas (I) and (II) may be converted into —CO—$X^z$, [wherein $X^z$ is selected from the following groups:

—NH—$(CH_2)_{p1}$—O—CO—C($R^{17}$)=$CH_2$;
—NH—$(CH_2)_{p1}$—O—CO—CH($R^{17}$)—$CH_2$—S—$CH_2$—CH(OH)—CH(OH)—$CH_2$—SH;

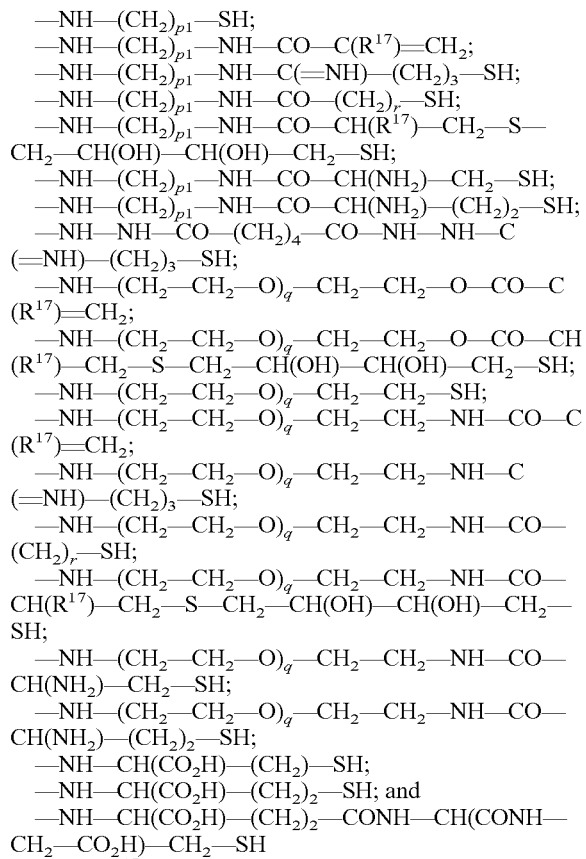

—NH—(CH$_2$)$_{p1}$—SH;
—NH—(CH$_2$)$_{p1}$—NH—CO—C(R$^{17}$)=CH$_2$;
—NH—(CH$_2$)$_{p1}$—NH—C(=NH)—(CH$_2$)$_3$—SH;
—NH—(CH$_2$)$_{p1}$—NH—CO—(CH$_2$)$_r$—SH;
—NH—(CH$_2$)$_{p1}$—NH—CO—CH(R$^{17}$)—CH$_2$—S—CH$_2$—CH(OH)—CH(OH)—CH$_2$—SH;
—NH—(CH$_2$)$_{p1}$—NH—CO—CH(NH$_2$)—CH$_2$—SH;
—NH—(CH$_2$)$_{p1}$—NH—CO—CH(NH$_2$)—(CH$_2$)$_2$—SH;
—NH—NH—CO—(CH$_2$)$_4$—CO—NH—NH—C(=NH)—(CH$_2$)$_3$—SH;
—NH—(CH$_2$—CH$_2$—O)$_q$—CH$_2$—CH$_2$—O—CO—C(R$^{17}$)=CH$_2$;
—NH—(CH$_2$—CH$_2$—O)$_q$—CH$_2$—CH$_2$—O—CO—CH(R$^{17}$)—CH$_2$—S—CH$_2$—CH(OH)—CH(OH)—CH$_2$—SH;
—NH—(CH$_2$—CH$_2$—O)$_q$—CH$_2$—CH$_2$—SH;
—NH—(CH$_2$—CH$_2$—O)$_q$—CH$_2$—CH$_2$—NH—CO—C(R$^{17}$)=CH$_2$;
—NH—(CH$_2$—CH$_2$—O)$_q$—CH$_2$—CH$_2$—NH—C(=NH)—(CH$_2$)$_3$—SH;
—NH—(CH$_2$—CH$_2$—O)$_q$—CH$_2$—CH$_2$—NH—CO—(CH$_2$)$_r$—SH;
—NH—(CH$_2$—CH$_2$—O)$_q$—CH$_2$—CH$_2$—NH—CO—CH(R$^{17}$)—CH$_2$—S—CH$_2$—CH(OH)—CH(OH)—CH$_2$—SH;
—NH—(CH$_2$—CH$_2$—O)$_q$—CH$_2$—CH$_2$—NH—CO—CH(NH$_2$)—CH$_2$—SH;
—NH—(CH$_2$—CH$_2$—O)$_q$—CH$_2$—CH$_2$—NH—CO—CH(NH$_2$)—(CH$_2$)$_2$—SH;
—NH—CH(CO$_2$H)—(CH$_2$)—SH;
—NH—CH(CO$_2$H)—(CH$_2$)$_2$—SH; and
—NH—CH(CO$_2$H)—(CH$_2$)$_2$—CONH—CH(CONH—CH$_2$—CO$_2$H)—CH$_2$—SH (wherein R$^{17}$ is a hydrogen atom or C$_{1-6}$ alkyl group, p1 represents an integer of 2 to 10, q represents an integer of 1 to 200, and r represents an integer of 1 to 3)], whereby intramolecular crosslinkages or intermolecular crosslinkages including other molecules are formed to thereby form a gel.

In the step of gelling the hyaluronic acid derivative of the present invention by chemical crosslinking, conditions may be selected as appropriate. Conditions for crosslinking include a method for their crosslinking, polymer concentration, crosslinking agent concentration, the type of solvent, solvent pH, salt concentration, temperature, time and so on.

In the step of gelling the hyaluronic acid derivative of the present invention, among reaction conditions for crosslinkage formation, for example, the polymer concentration and the introduction ratio of crosslinkable groups during chemical crosslinking can be elevated to thereby increase the crosslinking density of the resulting gel.

As to the crosslinking agent concentration in the step of gelling the hyaluronic acid derivative of the present invention, when using a crosslinking agent having crosslinkable groups at the both ends, it is preferably added at a concentration which allows these groups to rapidly contribute to crosslinking reaction without being either too much or too little. For example, when a polymer modified to have methacryloyl groups is crosslinked using DTT by Michael addition reaction, the MA group:SH group ratio is preferably 3:1 to 1:3, and particularly preferably 2:1 to 1:2.

A preferred solvent selected in the step of gelling the hyaluronic acid derivative of the present invention is one that can sufficiently dissolve polymers and a crosslinking agent. Without being limited thereto, water, dimethyl sulfoxide (DMSO), dimethylacetamide (DMAc), dimethylformamide (DMF), N-methylpyrrolidone (NMP), and mixed solvents selected therefrom are preferred for use. Alternatively, an organic solvent miscible to these solvents may also be mixed and used. Non-limiting examples of a miscible organic solvent include methanol, ethanol, propanol, isopropanol, butanol, acetone, acetonitrile, etc.

The hyaluronic acid derivative of the present invention forms a nanoparticle in an aqueous solution. Thus, by crosslinking under a dilute condition, a nano-size particle gel can be formed, and such a gel can be used as a carrier for sustained release in blood or as a targeting carrier. The dilute condition refers to 10 mg/mL or below, preferably 5 mg/mL or below, more preferably 1 mg/mL or below. On the other hand, by crosslinking under a high-concentration condition, a bulk gel in which particles are crosslinked with one another can be formed. This gel is useful as a subcutaneous sustained-release carrier. The high-concentration condition refers to 5 mg/mL or above, preferably 20 mg/mL or above, more preferably 40 mg/mL.

The step of gelling the hyaluronic acid derivative of the present invention may be performed in bulk or in a discontinuous phase (e.g., in an emulsion or in spray droplets). For example, when this step is performed in a W/O emulsion, an aqueous phase in which polymers and a crosslinking agent are dissolved may be emulsified in a water-immiscible solvent and provided for gelling reaction. Non-limiting examples of a water-immiscible solvent include hexane, chloroform, dichloromethane, ethyl acetate, medium-chain fatty acid triglyceride (MCT), liquid paraffin, soybean oil, etc. A surfactant may also be added for stable emulsification. Moreover, for example, emulsification may be performed in a solvent capable of being removed, such as supercritical carbon dioxide or PEG. In this case, once an aqueous or organic phase in which polymers and a crosslinking agent are dissolved is emulsified and dispersed in the above solvent, the polymers can be concentrated as a result of desolvation (solvent diffusion) to thereby obtain a gel with a higher crosslinking density During or after the step of gelling the hyaluronic acid derivative of the present invention, additional operations may be performed to stop the crosslinking reaction and to inactivate or wash off residual crosslinking functional groups. Crosslinking functional groups which are not used for the reaction, groups which are attached to only one end of crosslinking agent molecules, residual crosslinking agent molecules and so on are preferably removed in terms of safety, storage stability, side reactions with a drug to be encapsulated, etc. Without being limited thereto, for example, when there remain unreacted crosslinking agent molecules, they may be removed by washing with an excessive amount of water. Likewise, for example, when there remain methacryloyl groups substituted onto polymers, an excessive amount of mercaptoethanol or the like may be added to inactivate the methacryloyl groups, followed by washing with an excessive amount of water to remove the excess of mercaptoethanol. Moreover, for example, when there remain mercapto groups, an excessive amount of 3-maleimidopropionic acid, iodoacetic acid or the like may be added to inactivate the mercapto groups, followed by washing with an excessive amount of water to remove the excess of 3-maleimidopropionic acid or iodoacetic acid.

The step of gelling the hyaluronic acid derivative of the present invention may be followed by a grinding step. Grinding techniques include grinding with a pestle and a mortar, grinding in a mill, and so on. Preferred is grinding in a mill Examples of a mill grinder include rotating disk grinders such as a centrifugal mill (Nihonseiki Kaisha Ltd., Japan) and an impact mill (Dalton Co., Ltd., Japan), screen mill grinders such as an atomizer (Tokyo Atomizer Mfg. Co., Ltd., Japan), a sample mill (Tokyo Atomizer Mfg. Co., Ltd., Japan), a bantam mill (Tokyo Atomizer Mfg. Co., Ltd., Japan) and an SK mill (Tokken Inc., Japan), jet mills such as an ultra-micro labo jet mill (A-O jet mill, Seishin Enterprise Co., Ltd., Japan), as well as a Linrex mill (Liquid Gas Co., Ltd., Japan) which allows grinding at ultra-low temperatures, with a SK mill and a Linrex mill being preferred.

The step of gelling the hyaluronic acid derivative of the present invention may be followed by a drying step. Drying techniques include, for example, drying under ventilation, drying in a thermostatic vessel, drying under reduced pressure, and circulating hot air drying. Conditions such as air rate, drying period, temperature and pressure may be selected as appropriate within a range which causes no degradation or deterioration in the gel of the present invention.

A drug is encapsulated into the gel of the hyaluronic acid derivative of the present invention to obtain a pharmaceutical composition.

Techniques for drug encapsulation include those in which a drug solution is added to a pre-crosslinked hyaluronic acid derivative gel. In this technique, a drug is absorbed by diffusion into the inside of a swollen gel, and the absorbed drug is then held in physically crosslinked domains formed by hydrophobic interaction in the hyaluronic acid derivative gel to thereby achieve drug encapsulation. Without being limited thereto, conditions such as the type of solvent, salt concentration, pH, temperature, time, and addition of a denaturant may be selected as appropriate such that a drug is encapsulated stably and in high yields. For example, the salt concentration and pH during drug encapsulation will effect not only the swelling ratio and density of a hyaluronic acid derivative gel, but also the ionized state of a drug, etc. For this reason, suitable conditions may be used as appropriate for each combination between the hyaluronic acid derivative gel and drug. By carrying out drug encapsulation under low salt concentration, electrostatic repulsion between carboxy groups of the hyaluronic acid derivative can be utilized to decrease the gel density, whereby the amount of encapsulated drug can be increased or encapsulation of a drug having a higher molecular weight becomes possible. By increasing the salt concentration after drug encapsulation, electrostatic repulsion can be reduced to thereby increase the gel density and make the gel mesh smaller than the drug size, making it possible to hold the drug stably and retard the release. At this time, the salt concentration may be set to the physiological salt concentration.

Other techniques for drug encapsulation include those in which a drug is complexed with the hyaluronic acid derivative of the present invention, followed by crosslinking to form a gel. Without being limited thereto, conditions for complexation, e.g., the type of solvent, salt concentration, pH, temperature, time, addition of a denaturant, the concentration of the above hydrophilic polysaccharide derivativedrug concentration, and the ratio between HP and drug may be selected as appropriate such that the drug is stable and complexed with the nanogel in high yields. The uncomplexed free drug may be separated and removed by dialysis or size exclusion chromatography (SEC), etc. During crosslinking, it is preferred to use crosslinking conditions which cause no denaturation in the encapsulated drug.

The drug encapsulated in the hyaluronic acid derivative gel of the present invention is released by simple diffusion of the drug in the gel, by degradation of the hyaluronic acid derivative gel, and by substitution of the drug with a biological component. In a case where drug release is induced by diffusion of the drug, the drug release rate can be controlled by the crosslinking density of the gel, as well as the amount and/or hydrophobicity of hydrophobically crosslinked domains. Degradation of the gel includes, for example, degradation of chemically crosslinked domains, skeletal degradation of the hyaluronic acid derivative, etc. These degradations will cause a decrease in the crosslinking density (i.e., an increase in the swelling ratio). Upon decrease in the crosslinking density, the diffusion rate of the drug in the gel will be accelerated to promote its release, and cleavage of the bonds will also promote the release. For this reason, the drug release rate can be controlled by controlling the degradability of chemically crosslinked domains, the degradability of polymer skeletons, the degradability of spacers, etc.

Replacement with biological components is intended to mean, for example, that upon in vivo administration of the gel (e.g., subcutaneously or intravenously), plasma proteins (e.g., albumin) or lipids present in the body penetrate into the gel and replace the drug encapsulated therein to thereby cause drug release. In the gel of the hyaluronic acid derivative of the present invention, drug substitution associated with penetration of biological components can be controlled by not only physical crosslinking between hydrophobic groups but also the chemical crosslinking described above. The penetration rate of biological components can be controlled, e.g., by the crosslinking density of the gel and/or the type of electric charge in the gel. It should be noted that in the above case where a gel is formed by crosslinking before adding a drug solution to encapsulate the drug thereinto, conditions for drug encapsulation can be selected as appropriate, such that the drug is easily absorbed into the gel during encapsulation, while penetration of biological components is inhibited in the body. Without being limited thereto, for example, in the case of protein encapsulation, the encapsulation step may be accomplished near the isoelectric point of the protein to inhibit electrostatic repulsion between hyaluronic acid derivative and drug. Moreover, the encapsulation step may be accomplished below the pKa (ca. 4.0) of carboxylic acid derived from glucuronic acid contained in hyaluronic acid to thereby reduce the negative charge of the gel, which makes it possible to inhibit electrostatic repulsion with proteins which are negatively charged under such conditions and thus to improve the encapsulation efficiency. Further, for example, the encapsulation step may be accomplished at a lower salt concentration than in the body, whereby the gel has a higher swelling ratio than in the body to facilitate encapsulation.

A gel of the hyaluronic acid derivative of the present invention in which a hydrophobic group(s) and a crosslinking functional group(s) are simultaneously introduced can be formed by chemical crosslinking in the presence of a hydrophilic polysaccharide derivative having a hydrophobic group(s). Specifically, the hyaluronic acid derivative of the present invention in which a hydrophobic group(s) and a functional group(s) having an unsaturated bond(s) are introduced is mixed with a hydrophilic polysaccharide derivative having a hydrophobic group(s) and then crosslinked to thereby prepare a hyaluronic acid derivative gel physically encapsulating a hydrophilic polysaccharide derivative having a hydrophobic group(s). This gel formation can also be carried out using HA-AM, HA-ALD, HA-SH.

The hydrophilic polysaccharide derivative having a hydrophobic group(s) means hydrophilic polysaccharides obtainable by introducing into hydrophilic polysaccharides or a derivative thereof at least one or more hydrophobic groups per molecule of a hydrophilic polysaccharide. Such a hydrophilic polysaccharide is not limited in any way, and preferred are pullulan, amylopectin, amylose, dextran, mannan, levan, inulin, chitin, chitosan, hyaluronic acid, and dextrin, which are commercially available or may be prepared to have various average molecular weights according to the reported processes. Particularly preferred for use as hydrophilic polysaccharides are pullulan, hyaluronic acid, and dextrin. A preferred dextrin is Cluster Dextrin®. Cluster Dextrin® can be purchased from Ezaki Glico Co., Ltd. Japan and used for this purpose. Hydrophobic groups are not limited in any way, and preferred are groups such as a $C_{8-50}$ hydrocarbon group, a steryl group, a polylactic acid (PLA) group, and a polylactic acid-glycolic acid copolymer (PLGA) group, or groups containing these groups. Particularly preferred is a group containing a cholesteryl group, a linear or branched $C_{8-30}$ alkyl or a group containing the same. Such a hydrophobic group may be introduced via a spacer.

Such a hydrophilic polysaccharide derivative having a hydrophobic group(s) can be prepared in various known manners. A commercially-available hydrophilic polysaccharide derivative modified to have N-[6-(cholesteryloxycarbonylamino)hexyl]carbamoyl groups which are introduced as hydrophobic groups into hydroxy groups in pullulan as a hydrophilic polysaccharide (the derivative thus obtained is hereinafter also referred to as "cholesterol pullulan" or "CHP") may be purchased (e.g., from NOF Corporation, Japan) and obtained. In such a hydrophilic polysaccharide derivative having a hydrophobic group(s), several molecules will spontaneously associate in an aqueous solution upon hydrophobic interaction to form a nano-size (1 to 1,000 nm) particle (nanogel) having a gel structure, whereby the derivative can be complexed with a hydrophobic drug or with a pharmacologically active protein or peptide.

Although there is no particular limitation on the molecular weight of the hydrophilic polysaccharide derivative having a hydrophobic group(s) used in the present invention, it is preferably 1 kDa to 1,000 kDa, and more preferably 10 kDa to 300 kDa. Moreover, the above hydrophilic polysaccharide derivative may be in the form of a pharmaceutically acceptable salt.

Moreover, for example, hydroxy groups contained in the hyaluronic acid derivative of the present invention and the hydrophilic polysaccharide derivative having a hydrophobic group(s) can also be used as crosslinkable groups. Specifically, hydroxy groups contained in the hyaluronic acid derivative of the present invention and the hydrophilic polysaccharide derivative having a hydrophobic group(s) may be crosslinked with a specific crosslinking agent, such as divinylsulfone (DVS), carbodiimide, or a crosslinking agent having glycidyl ether groups at the both ends of a $C_{2-20}$ alkylene group.

In a case where multiple kinds of substituents are introduced into a carboxy group(s) of hyaluronic acid, these substituents may be introduced simultaneously or consecutively.

The hyaluronic acid derivative of the present invention has a characteristic that it spontaneously associates in an aqueous solution upon hydrophobic interaction of the hydrophobic group(s) to form a nanoscale particle. The nanoparticle formed by the hyaluronic acid derivative of the present invention is a significantly effective means for constructing a desired drug delivery system, and can be used as a capsule which is delivered to a target site while retaining an active ingredient, i.e., protein, peptide, low-molecular-weight compound, in a hydrophobic domain formed therein. Furthermore, by conjugating a drug, it becomes possible to deliver the drug to a target site.

The nanoscale particle can be administered systemically, particularly intravenously, and can be used as a carrier for sustained release of an encapsulated (complexed) drug in blood, or as a targeting carrier for selectively delivering a drug to a target organ and cell. In a case of using as a targeting carrier, a carboxy group(s) of glucuronic acid moiety of the HA derivative may not be highly modified (e.g. modification ratio of 54% or less), whereby delivery of a drug targeting a hyaluronic acid receptor, such as CD44, RHAMM, LYVE-1, or HARE, becomes possible as described above. By targeting especially CD44 or RHAMM, it becomes possible to target a tumor. Further, a carboxy group(s) of glucuronic acid moiety of the HA derivative may be highly modified (e.g. modification ratio of 55% or more) and a target element described above may be added, whereby it becomes possible to target each organ and cell. To ensure retention of a drug in blood, the hyaluronic acid derivative may further be chemically crosslinked.

It is known that in a case where the HA derivative that is not highly modified is used as a carrier for sustained release of a drug in blood or as a targeting carrier, it is instantaneously incorporated into HARE receptors present in sinusoidal endothelium such as liver and metabolized; the HA derivative has a problem that it rapidly disappears from blood. However, the residence time in blood of the HA derivative of the present invention depends on the molecular weight, and an HA derivative prepared using low-molecular-weight HA (5 kDa to 27 kDa) as a raw material can be used as a carrier for sustained release of a drug in blood or targeting carrier excellent in residence time in blood.

Further, it is known that a molecule of a certain size or smaller receives renal excretion; there is a report that polyethyleneglycol (PEG), which is a linear polymer like hyaluronic acid, receives renal excretion at a molecular weight of 40 kDa or less (European Journal of Cancer, Vol. 31, pp. 766-770, 1995). Accordingly, hyaluronic acid and hyaluronic acid derivative of the same or less molecular weight may also receive renal excretion and instantaneously disappear from blood. However, the hydrophobic group-introduced HA derivative of the present invention has excellent residence time in blood, regardless of the modification ratio of carboxy groups and even when its molecular weight is not greater than the molecular weight at which PEG receives renal excretion, making it possible to use the hydrophobic group-introduced HA derivative of the present invention as a carrier for sustained release of a drug in blood or as a targeting carrier.

The particle by the hyaluronic acid derivative is formed by self association in an aqueous solution and, thus, can be formed by dissolving a solid hyaluronic acid derivative in water or salt solution. In another method, the particle can be formed by dissolving in another solvent (e.g. DMSO) and then substituting with water or salt solution. Ultrasonic treatment may be carried out so that the resulting particles have uniform size.

As the introduction ratio of hydrophobic groups of the hyaluronic acid derivative is increased, the solubility in water decreases. Therefore, to form a particle dispersible in an aqueous solution, it is preferable to use a hyaluronic acid derivative prepared such that a percentage of a hydrophobic group(s) introduced via a covalent bond(s) is 80% or less, preferably 60% or less.

Since the hyaluronic acid derivative has a carboxy group(s) which is a dissociable group, the solubility is lower at higher ion intensities in the system. Thus, by controlling the introduction ratio, a hyaluronic acid derivative that dissolves under low salt concentration or salt-free conditions and aggregates and/or precipitates at the physiological salt concentration can be prepared, and such a hyaluronic acid derivative may be used as a matrix for a formulation for sustained release in the subcutis. Further, the hyaluronic acid derivative in which a hydrophobic group(s) is introduced to an extent that stable particles are formed even at the physiological salt concentration may be used as a systemic-administration type drug carrier.

It is shown that the HA derivative of the present invention has a range of introduction of a hydrophobic group(s) into carboxy groups in which the HA derivative aggregates at the physiological salt concentration to form a precipitate, and that the HA derivative is precipitated with a protein (erythropoietin) being encapsulated (complexed). Further, it is confirmed that when a pharmaceutical composition comprising the hyaluronic acid derivative of the present invention which encapsulates (is complexed with) human growth hormone and is precipitated is subcutaneously administered to rats, the pharmaceutical composition exhibits sustained-release effect. It is also confirmed that the pharmaceutical composition administered in the form of a solution (dispersion) also precipitates in the subcutis (at the physiological salt concentration) and exhibits sustained-release effect.

Although the particle size of the particle formed is not limited in any way, the particle size is preferably 200 μm or smaller, more preferably 100 μm or smaller, so that when the particle is administered by injection, it can pass through a needle without clogging the needle. In a case of intravenous administration, the particle size is preferably 500 nm or smaller, more preferably 200 nm, in order not to occlude peripheral blood vessels. To avoid the intake by the eticuloendothelial system and to increase the residence time in blood, the particle size is preferably 100 nm or smaller.

The hyaluronic acid derivative of the present invention can be used as a drug carrier for a pharmaceutical formulation. The hyaluronic acid derivative of the present invention spontaneously forms a complex with a drug in an aqueous solution. Thus, no special operation is required, and a carrier-drug complex can be formed simply by mixing the hyaluronic acid derivative with a drug in an aqueous solution and then incubating the mixture. The driving force of complex formation is mainly hydrophobic interaction between the hydrophobic group(s) of the hyaluronic acid derivative and the drug, but in a case where the drug is basic, electrostatic interaction between the hyaluronic acid derivative and carboxylic acid may contribute to the complex formation. At the salt concentration of the living body, the electrostatic interaction is weak, whereas the hydrophobic interaction is strong. It is therefore considered that a complex is formed mainly by hydrophobic interaction.

In a case where Y of the group —$NR^a$—Y—$X^1$ in the above formula (I) is alkylene, the longer the carbon chain of alkylene is, the higher the hydrophobicity of the group is, making it possible to form stable particles by strong hydrophobic interaction. Further, the longer the alkylene group is, the more the intermolecular tangling occurs, making it possible to increase the viscosity. By changing the length of the alkylene group, the particle size can be controlled.

In a case where a linker (spacer) moiety in the hydrophobic group(s) is an ester or carbonate (e.g., a case where $X^1$ is —COO—R and —O—COO—R), the ester or carbonate is decomposed in the living body and the hydrophobicity of the hyaluronic acid derivative is decreased, which further increases the biodegradability. This is preferable in terms of safety. Further, it is known that the pH around tumor tissue is low. In a case of having such a spacer, an association product of the hyaluronic acid derivative of the present invention holding an intended drug is decayed around the tumor, whereby the drug is released around the tumor.

Especially in a case of a linker having a β-thioester structure such as —O—CO—$CH_2$—$CH_2$—S—, even a slight decrease in pH (ca. pH 6) will promote decomposition. Thus, the pH response is sharper than a normal ester. Further, in a case of aiming at delivering a drug into cells, it also responds to a pH decrease in endosome, making it possible to release the drug only after the drug is incorporated into the cells.

In a case where the linker (spacer) moiety has a disulfide bond(s) (e.g., a case where $X^1$ is —S—S—R), the linker is decomposed under a reduction situation, and the hydrophobicity of the hyaluronic acid derivative is decreased, whereby an association product of the hyaluronic acid derivative of the present invention is decayed. It is known that in cytoplasm is a reducing environment. Thus, a drug is encapsulated into the hyaluronic acid derivative using the above linker and then administered, whereby the drug is released only in cytoplasm while the drug is not released in blood.

In a case where the linker (spacer) moiety has a peptide that is enzyme-specifically cleaved (e.g., a case where the hydrophobic group is —Z—$NR^a$—Y—$NR^b$—COO—R), the linker is decomposed only at a site where an enzyme is present, and a part of the hydrophobic group(s) is eliminated, whereby an association product of the hyaluronic acid derivative of the present invention is decayed. For example, in lysosome, Gly-Phe-Leu-Gly is specifically cleaved. Further, in a case where the linker contains a peptide that is cleaved by peptidase expressed at a tumor or inflamed site, it is possible to release the drug specifically at the tumor.

In a case where the linker moiety is not a linker that receives physical chemical cleavage, such as an ester bond, a carbonate bond, or a disulfide bond, there is an advantage that storage stability in a formulation is excellent.

Conditions for formation of a carrier-drug complex, e.g., the type of solvent, salt concentration, pH, temperature, time, and addition of a denaturant may be changed as appropriate depending on a drug used. For example, the salt concentration and pH during encapsulation of a drug will effect not only the density of a hyaluronic acid derivative but also the ionized state of the drug, etc. Examples of a denaturant used include urea, guanidine hydrochloride, sodium dodecyl sulfate, etc. In a case where a denaturant is added, the excess of denaturant can be removed by washing with an excessive amount of water or the like after a complex is formed.

Without being limited thereto, for example, in the case of forming a complex of the hyaluronic acid derivative of the present invention and a protein, the complex formation may be accomplished near the isoelectric point of the protein to inhibit electrostatic repulsion between hyaluronic acid derivative and protein, making it possible to increase the amount of protein contained in the complex. Moreover, the complex formation step may be accomplished under conditions below the pKa (ca. 4.0) of carboxy group(s) of glucuronic acid moiety to thereby reduce the negative charge of the hyaluronic acid derivative, which makes it possible to inhibit electrostatic repulsion in a case where proteins are negatively charged under such conditions and thus to increase the amount of proteins contained in the complex. Further, for example, the complex formation step may be accomplished at a lower salt concentration than in the body, whereby the particle density of the hyaluronic acid derivative formed in an aqueous solution is decreased, making it possible to increase the amount of protein contained in the complex. Further, by increasing the salt concentration in that state, the particle density can be increased, making it possible to stably encapsulate a protein.

Formation of a complex of the hyaluronic acid derivative and protein may also be affected by the molecular weight of the protein. In general, a protein having a lower molecular weight moves into a hyaluronic acid derivative particle at a higher rate. Further, the particle density, which depends on the introduction ratio of hydrophobic groups, may also affect the rate of formation of a complex with a protein and the amount of the protein contained in the complex.

The drug release from the complex of the hyaluronic acid derivative and the drug in the living body is promoted by replacement of the drug with biological components as well as diffusion of the drug from the complex. By increasing or decreasing the particle density to thereby control the above diffusion or replacement, the sustained release of the drug can be controlled.

In the living body, biological components such as plasma proteins and lipids are present. In a case where a complex of a hyaluronic acid derivative and a drug is administered to the living body, e.g., in the subcutis or into blood, the biological components may replace the drug in the complex to thereby cause drug release. A major protein in the living body that causes the above replacement is albumin. By reducing the introduction ratio of hydrophobic groups of the hyaluronic acid derivative of the present invention, the negative charge of carboxy group(s) of glucuronic acid moiety can be increased, whereby replacement with albumin having negative charge (pI=4.6) can be inhibited.

Examples of a method using the hyaluronic acid derivative of the present invention as a drug carrier include a method in which a drug is conjugated to the hyaluronic acid derivative of the present invention, as well as the above-described method in which the hyaluronic acid derivative spontaneously forms a complex with a drug in an aqueous solution.

As a method for the preparation of a conjugate comprising the hyaluronic acid derivative of the present invention and a drug, a method used to prepare a known polymer-drug conjugate can be used. For example, the following reactions may be used:

Reaction of a carboxy group(s) of glucuronic acid moiety of hyaluronic acid derivative with an amino group(s), hydroxy group(s), iodo group(s), or bromo group(s) of a drug or an amino group(s), hydroxy group(s), bromo group(s), or iodo group(s) introduced in a drug;

Reaction of hydroxy in position 6 of N-acetylglucosamine moiety of hyaluronic acid derivative with a carboxy group(s) of a drug or a carboxy group(s) introduced in a drug;

Reaction of an amino group(s) introduced in a hyaluronic acid derivative with a carboxy group(s) of a drug or a carboxy group(s) introduced in a drug;

Reaction of an amino group(s) introduced in a hyaluronic acid derivative with a drug converted by modification into isothiocyanate, isocyanate, acyl azide, NHS ester, epoxide or the like;

Reaction of an amino group(s) of a drug or an amino group(s) introduced in a drug with a hyaluronic acid derivative converted by modification into isothiocyanate, isocyanate, acyl azide, carbonyl, NHS ester, epoxide or the like;

Schiff base formation and reductive amination reaction of an amino group(s) introduced in a hyaluronic acid derivative with a drug having a carbonyl group(s) or with a drug in which a carbonyl group(s) is introduced (e.g., aldehyde, ketone, etc.);

Schiff base formation and reductive amination reaction of an amino group(s) of a drug or an amino group(s) introduced in a drug with a hyaluronic acid derivative in which a carbonyl group(s) is introduced by modification;

Reaction of a mercapto group(s) introduced in a hyaluronic acid derivative with a drug which is a compound having an unsaturated bond(s) (e.g., maleimido, acrylic ester, acrylamide, methacrylic ester, methacrylamide, allylation product, vinylsulfone, etc.), halide (e.g., chloroacetic acid ester, bromoacetic acid ester, iodoacetic acid ester, chloroacetic acid amide, bromoacetic acid amide, iodoacetic acid amide, etc.) or thiol, or with a drug converted by modification into any of the above compounds; and Reaction of a mercapto group(s) introduced in a drug with a hyaluronic acid derivative converted by modification into a compound having an unsaturated bond(s) (e.g., maleimido, acrylic ester, acrylamide, methacrylic ester, methacrylamide, allylation product, vinylsulfone, etc.), halide (e.g., chloroacetic acid ester, bromoacetic acid ester, iodoacetic acid ester, chloroacetic acid amide, bromoacetic acid amide, iodoacetic acid amide, etc.) or thiol.

The linkers (spacers) used to introduce the above-described hydrophobic group(s) into the HA derivative(s) and containing an ester, carbonate, βthioester, disulfide, and/or peptide which is cleaved in a specific site may be used as a linker for conjugation with a drug. As described above, these linkers are cleaved in a target site to thereby release a drug in the target site.

The reagent used to modify a hyaluronic acid derivative or drug to thereby prepare a conjugate is not limited in any way as long as it does not cause any inconvenient reaction in the conjugate preparation. The compound is available as a reagent, or may be synthesized by reference to publicly-known methods described in prior arts.

Specifically, the hyaluronic acid derivative of the present invention is synthesized, reacted with a drug having an amino group(s) or an amino group-introduced drug using a condensing agent such as DMT-MM to thereby conjugate the drug via an amide bond(s). At this time, the drug may be added together with cholesteryl 6-aminohexylcarbamate hydrochloride and the like to thereby introduce a hydrophobic group(s) simultaneously. Further, the compound may be added after or before the drug. The hyaluronic acid derivative of the present invention may be synthesized and purified and thereafter reacted with a drug, or a hydrophobic group derivative may be introduced after a drug-introduced hyaluronic acid derivative is synthesized and purified.

Alternatively, the hyaluronic acid derivative of the present invention may be synthesized and then reacted with a drug having a hydroxy group(s) or with a hydroxy group-introduced drug using a condensing agent such as DMT-MM and 1,3-dichlorohexylcarbodiimide (DCC) to thereby conjugate the drug to the hyaluronic acid derivative via an ester bond(s). At this time, the drug may be added together with cholesteryl 6-aminohexylcarbamate hydrochloride and the like to thereby introduce a hydrophobic group(s) simultaneously. Further, the compound may be added after or before the drug. To avoid hydrolysis of an ester, however, it is preferable to conjugate the drug after introduction of a hydrophobic group(s). The above method can be carried out by reference to, for example, a report that paclitaxel was introduced into HA via an ester (Bioconjugate, Vol. 19, pp. 1319-1325, 2008).

The hyaluronic acid derivative of the present invention may be synthesized and then reacted with a drug which is a bromide or iodide or with a drug converted by modification into a bromide or iodide to thereby convert a carboxy group(s) of a glucuronic acid moiety into an ester(s), whereby the drug is conjugated. To avoid hydrolysis of an ester(s), it is desirable to conjugate the drug after introduction of a hydrophobic group(s).

The hyaluronic acid derivative of the present invention may be synthesized, and a drug having a carboxy group(s) or a carboxy group-introduced drug may be converted into NHS ester and thereafter reacted with hydroxy in position 6 of N-acetylglucosamine moiety to thereby conjugate the drug via an ester bond(s). At this time, the drug may be added either after or before introduction of a hydrophobic group(s) into HA via cholesteryl6-aminohexylcarbamate hydrochloride or the like. Further, the hyaluronic acid derivative of the present invention may be synthesized and purified and thereafter reacted with a drug, or a hydrophobic group derivative may be introduced after a drug-introduced hyaluronic acid derivative is synthesized and purified. To avoid hydrolysis of an ester bond(s), it is desirable to conjugate the drug after introduction of a hydrophobic group derivative. The above method can be carried out by reference to, for example, a report that camptothecin was introduced into HA via an ester (International Publication No. WO2009/074678) and the like.

In one embodiment, the hyaluronic acid derivative of the present invention is synthesized, and then a carboxy group(s) of a glucuronic acid moiety is subjected to dehydration condensation reaction with a diamine such as ethylenediamine to thereby introduce an amino group(s). Further, N-succinimidyl iodoacetate (PIERCE) or N-succinimidyl[4-iodoacetyl] aminobenzoate (PIERCE) may be reacted with the amino group(s) to thereby synthesize a hyaluronic acid derivative in which an iodoacetyl group(s) is introduced. A drug having a thiol group may be conjugated to this hyaluronic acid derivative. The above method is especially effective, because even a high-molecular-weight drug containing many reactive groups such as amino groups, e.g., protein, peptide, nucleic acid, can be thiol-selectively conjugated. At this time, the drug may be introduced either before or after introduction of a hydrophobic group derivative into HA.

The hyaluronic acid derivative of the present invention in which $X^1$ is —$NH_2$—COO—R is synthesized, and a portion of carboxy groups of a glucuronic acid moiety is reacted with 2-aminoethyl 2-pyridyl disulfide hydrochloride. A drug having a mercapto group(s) or a mercapto group-introduced drug can be introduced into this hyaluronic acid derivative by disulfide bond-interchange reaction, i.e., substitution reaction.

To effectively maintain the biological activity of the conjugate, the length of the linker between the drug and the hyaluronic acid derivative can be adjusted. Further, a peptide linker which will be cleaved by an enzyme or the like in a specific site in the living body may be introduced. The foregoing can be accomplished by reference to, for example, a report that methotrexate was introduced into HA via a peptide-containing linker (International Publication No. WO2005/095464), a report that doxorubicin was introduced via a linker containing HPMA (N-(2-hydroxypropyl)methacrylamide) and peptide (International Publication No. WO2002/090209), and the like.

There are many reports of ADC (Antibody Drug Conjugate) in which a low-molecular-weight compound was conjugated to an antibody (International Publication No. WO2009/026274; Expert Opinion, Vol. 15, pp. 1087-1103, 2005; Bioconjugate Chem., Vol. 19, pp. 1960-1963, 2008; Bioconjugate Chem., in press, Bernhard Stump et al., Antibody-Drug Conjugates: Linking Cytotoxic Payloads to Monoclonal Antibodies). By reference to these reports, a conjugate of a hyaluronic acid derivative and a low-molecular-weight compound can be prepared.

A pharmaceutical composition containing the hyaluronic acid derivative of the present invention and at least one drug and a conjugate of the hyaluronic acid derivative of the present invention and at least one drug may be in the form of a nanoparticle, microparticle, solution, emulsion, suspension, gel, micelle, implant, powder, or film. The powder may be produced by grinding a solid obtained by lyophilization or spray drying, or by drying a precipitate.

The route of administration of the pharmaceutical composition and conjugate of the present invention may be oral, parenteral, intranasal, intravaginal, intraocular, subcutaneous, intravenous, intramuscular, intracutaneous, intraperitoneal, intracerebral, or intraoral.

The pharmaceutical composition and conjugate of the present invention are preferably 200 µm or smaller, more preferably 100 µm or smaller, so that they can pass through a needle without clogging, especially in a case where they aim at local sustained-release.

The size of the pharmaceutical composition and conjugate of the present invention is preferably 5 µm or smaller, especially in a case where they aim at targeting a hyaluronic acid receptor such as CD44. The hyaluronic acid derivative used preferably has an introduction ratio of hydrophobic groups of 10% or less so that binding to a hyaluronic acid receptor is not inhibited.

The size of the pharmaceutical composition and conjugate of the present invention is preferably 500 nm or smaller, more preferably 200 nm or smaller, especially in a case of aiming at, especially, prolongation of residence time in blood, as well as accumulation in tumor or inflamed tissue. To avoid the uptake by the reticuloendothelial system and to prolong the residence time in blood, the size is preferably 100 nm or smaller. At this time, it is preferable to use a hyaluronic acid derivative in which carboxy groups of a glucuronic acid moiety are mostly converted to thereby inhibit binding to a hyaluronic acid receptor.

The size of the pharmaceutical composition and conjugate of the present invention is preferably 200 µm or smaller in a case where they have mucoadhesive properties and are to be used for the purpose of noninvasive administration. In terms of mucoadhesive properties, the introduction ratio of hydrophobic groups of the hyaluronic acid derivative used is preferably low.

The drug with which the hyaluronic acid derivative of the present invention forms a complex is not limited in any way as long as it is a drug that can be entrapped. Further, the drug to which the hyaluronic acid derivative of the present invention is conjugated is not limited in any way as long as a conjugate can be prepared. Examples of such a drug include proteins and/or peptides, polysaccharides, nucleic acids, and low-molecular-weight compounds, preferably, proteins and/or peptides.

Examples of a low-molecular-weight compound include carcinostatic agents (e.g., alkylating agents, antimetabolites, alkaloids), immunosuppressive agents, anti-inflammatory agents (e.g., steroid drugs, nonsteroidal anti-inflammatory agents), antirheumatic agents, antibacterial agents (e.g., β-lactam antibiotics, aminoglycoside antibiotics, macrolide antibiotics, tetracycline antibiotics, new quinolone antibiotics, sulfa drugs) and so on.

Examples of a protein or peptide include erythropoietin (EPO), granulocyte colony-stimulating factor (G-CSF), interferon-α, β, γ, (INF-α, β, γ), thrombopoietin (TPO), ciliary neurotrophic factor (CNTF), tumor necrosis factor (TNF), tumor necrosis factor binding protein (TNFbp), interleukin-10 (IL-10), FMS-like tyrosine kinase (Flt-3), growth hormone (GH), insulin, insulin-like growth factor-1 (IGF-1), platelet-derived growth factor (PDGF), interleukin-1 receptor antagonist (IL-1ra), brain-derived neurotrophic factor (BDNF), keratinocyte growth factor (KGF), stem cell factor (SCF), megakaryocyte growth and development factor (MGDF), osteoprotegerin (OPG), leptin, parathyroid hormone (PTH), basic fibroblastic growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), antibody, diabody, minibody, fragmented antibody, and so on.

Examples of nucleic acids include DNA, RNA, antisense, decoy, ribozyme, small interfering RNA, RNA aptamer, and so on.

In the present invention, —NR$^a$ in the formula (I) forms an amide bond with carbonyl (CO), and a hydrophobic group having a steryl group is introduced by conversion of a carboxy group of hyaluronic acid or a salt thereof into an amide. It is also possible to introduce a hydrophobic group by conversion of a carboxy group into an ester. Specifically, —COOH contained in hyaluronic acid or a salt thereof may be converted into —COOA, wherein A is —R,
—Y—NR$^b$—R,
—Y—NR$^b$—COO—R,
—Y—NR$^b$—CO—R,
—Y—NR$^b$—CO—NR$^c$—R,
—Y—COO—R,
—Y—O—COO—R,
—Y—S—R,
—Y—CO—Y$^a$—S—R,
—Y—O—CO—Y$^b$—S—R,
—Y—NR$^b$—CO—Y$^b$—S—R, or
—Y—S—S—R (R, Y, R$^b$, R$^c$, Y$^a$, and Y$^b$ are as defined above).

It is also possible to introduce a hydrophobic group having a steryl group into hyaluronic acid or a salt thereof by conversion of a hydroxy group (—OH), instead of a carboxy group, of hyaluronic acid or a salt thereof into —OAa, wherein Aa is —R,
—CO—Y—NR$^b$—COO—R,
—OCO—Y—NR$^b$—COO—R,
—CO—NR$^a$—Y—NR$^b$—COO—R,
—CO—Y—COO—R,
—OCO—Y—COO—R,
—CO—NR$^a$—Y—COO—R,
—CO—Y—OCOO—R,
—OCO—Y—OCOO—R,
—CO—NR$^a$—Y—OCOO—R,
—CH$_2$CH(OH)—O—R,
—CH(CH$_2$OH)—OR, and
—CH$_2$CHR$^h$—SO$_2$—OR (R, Y, R$^a$, and R$^b$ are as defined above, and R$^h$ is a hydrogen atom or C$_{1-6}$ alkyl).

In a case where Z in the above formula (I) is a peptide linker comprising 2 to 30 arbitrary amino acid residues, the group —Z—N(R$^a$)—Y—X$^1$ may be converted into the group —N(R$^a$)—Y—NR$^b$—Z—X$^{1a}$ (R$^a$, Y, R$^b$, R, R$^c$, and Y$^b$ are as defined herein, and X$^{1a}$ represents the formula:

—R,
—COO—R,
—CO—R,
—CO—NR$^c$—R, or
—CO—Y$^b$—S—R).

The peptide linker binds to the group X$^{1a}$ at the N terminal.

EXAMPLES

Preferred embodiments of the present invention are specifically described in the following examples.

In the following description, the term "HA unit" is intended to mean a repeating unit (1 unit) composed of N-acetylglucosamine-glucuronic acid in hyaluronic acid.

Example 1

Preparation of Cholesteryl Group-Introduced HA Derivative

Example 1-1

Preparation of Cholesteryl 6-Aminohexylcarbamate Hydrochloride

To a solution of cholesteryl chloroformate (3.37 g, 7.5 mmol) in anhydride dichloromethane (20 mL), triethylamine (TEA, 1.05 mL) was added in an argon atmosphere and stirred. On ice, 6-(t-butoxycarbonyl)amino-1-aminohexane (1.12 mL, 5 mmol) was added by dropping, stirred for 30 minutes on the ice, and then heated to room temperature, and the mixture was stirred overnight. The reaction mixture was washed with ultrapure water and with brine and then dried with anhydrous magnesium sulfate, and thereafter the solvent was distilled off under reduced pressure. The resulting residue was purified by silica gel column chromatography (eluent: ethyl acetate:n-hexane=1:4). The fractions of an intended product were combined together, and the solvent was distilled off under reduced pressure.

The resulting residue was dissolved in ethyl acetate (40 mL), and 4N hydrochloric acid/ethyl acetate solution (40 mL) was added and stirred overnight at room temperature. The resulting precipitate was removed by centrifugal separation. The resulting solid was washed four times with ethyl acetate and then dried under reduced pressure to give a hydrochloride (1.2 g) of cholesteryl 6-aminohexylcarbamate (Chol-C$_6$). The $^1$H-NMR spectrum (JNM-ECA500 JEOL Ltd.; EtOH-d$_6$) of the product is shown in FIG. 1.

Example 1-2

Preparation of Cholesteryl 2-Aminoethylcarbamate Hydrochloride

Figure 2:
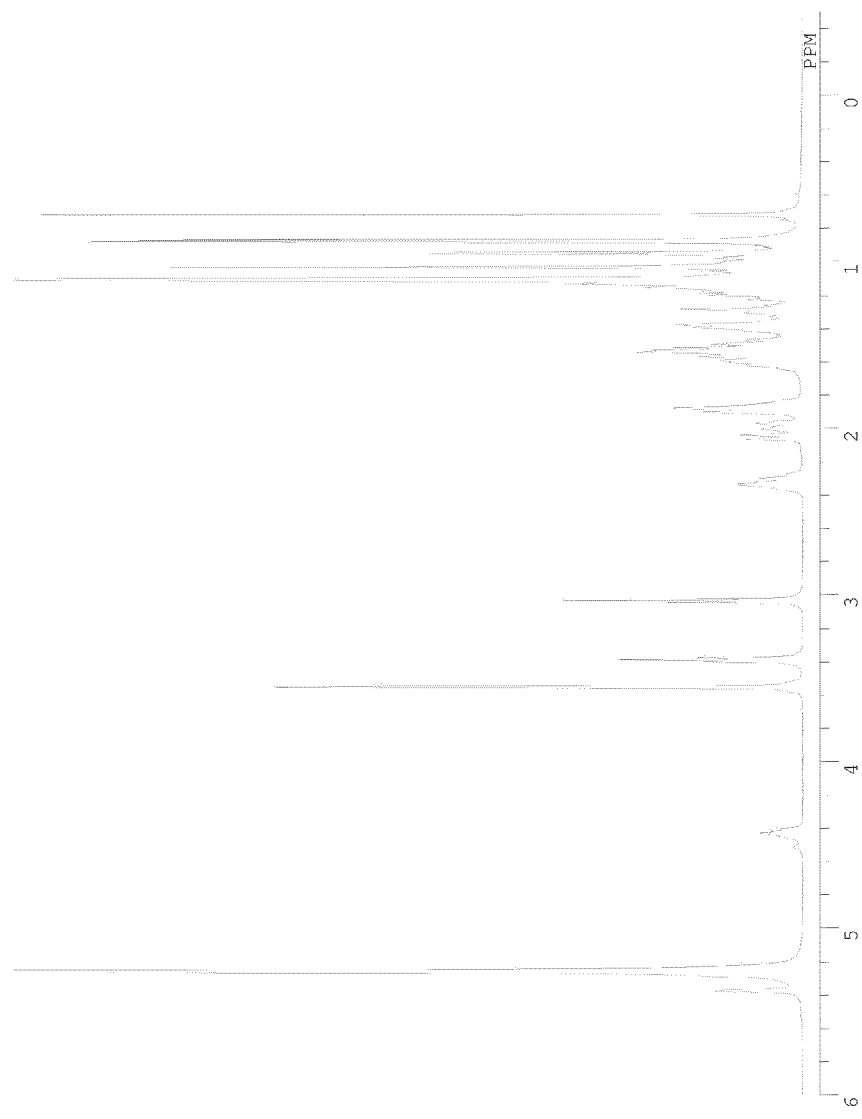
FIG. 2 is one example of the $^1$H-NMR spectrum of cholesteryl 2-aminoethylcarbamate hydrochloride prepared in Example 1-2.

Except that 2-(t-butoxycarbonyl)amino-1-aminoethane (0.79 mL, 5 mmol) was used in place of 6-(t-butoxycarbonyl)amino-1-aminohexane and ethyl acetate:n-hexane=1:2 was used as an eluent in the silica gel column chromatography, the procedure of Example 1-1 was repeated to give a hydrochloride (2.3 g) of cholesteryl 2-aminoethylcarbamate (Chol-C$_2$). The $^1$H-NMR spectrum (JNM-ECA500 JEOL Ltd.; EtOH-d$_6$) of the product is shown in FIG. 2.

Example 1-3

Preparation of Cholesteryl 8-Aminooctylcarbamate Hydrochloride

To a solution of 8-(t-butoxycarbonyl)amino-1-aminooctane (1.21 g, 5 mmol) in anhydride dichloromethane (100 mL) and anhydrous toluene (200 mL), TEA (0.7 mL) was added in an argon atmosphere and stirred. On ice, an anhydrous dichloromethane solution of cholesteryl chloroformate (2.66 g, 6 mmol) was added by dropping, stirred on the ice for 30 minutes, and then heated to room temperature, and the mixture was stirred overnight. The reaction mixture was concentrated under reduced pressure, and the resulting residue was purified by silica gel column chromatography (eluent:

ethyl acetate:n-hexane=1:4). The fractions of an intended product were combined together, and the solvent was distilled off under reduced pressure.

Figure 3:
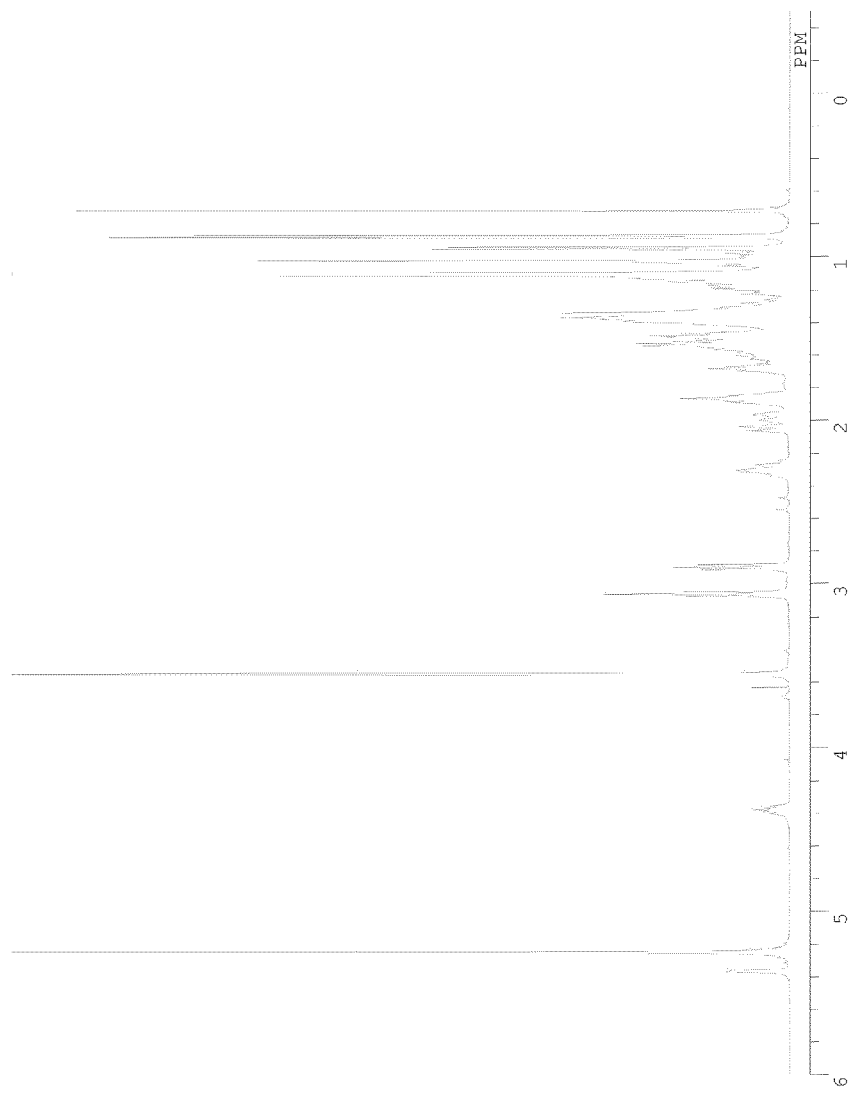
FIG. 3 is one example of the $^1$H-NMR spectrum of cholesteryl 8-aminooctylcarbamate hydrochloride prepared in Example 1-3.

The resulting residue was dissolved in dichloromethane (1.5 mL), and trifluoroacetic acid (1.5 mL) was added and stirred at room temperature for 2 hours. The solvent was distilled off under reduced pressure, and the resulting residue was purified by silica gel column chromatography (eluent: ethyl acetate:methanol:ammonia water=9:1:0.5). The fractions of an intended product were combined together, and the solvent was distilled off under reduced pressure. To the resulting residue, 4N hydrochloric acid/dioxane was added, and then ethyl acetate was added to give a solid. The solid was recovered, washed with ethyl acetate, and dried under reduced pressure to give a hydrochloride (0.5 g) of cholesteryl 8-aminooctylcarbamate (Chol-$C_8$). The $^1$H-NMR spectrum (JNM-ECA500 JEOL Ltd.; EtOH-$d_6$) of the product is shown in FIG. 3.

Example 1-4

Preparation of Cholesteryl 12-Aminododecylcarbamate Hydrochloride

Figure 4:
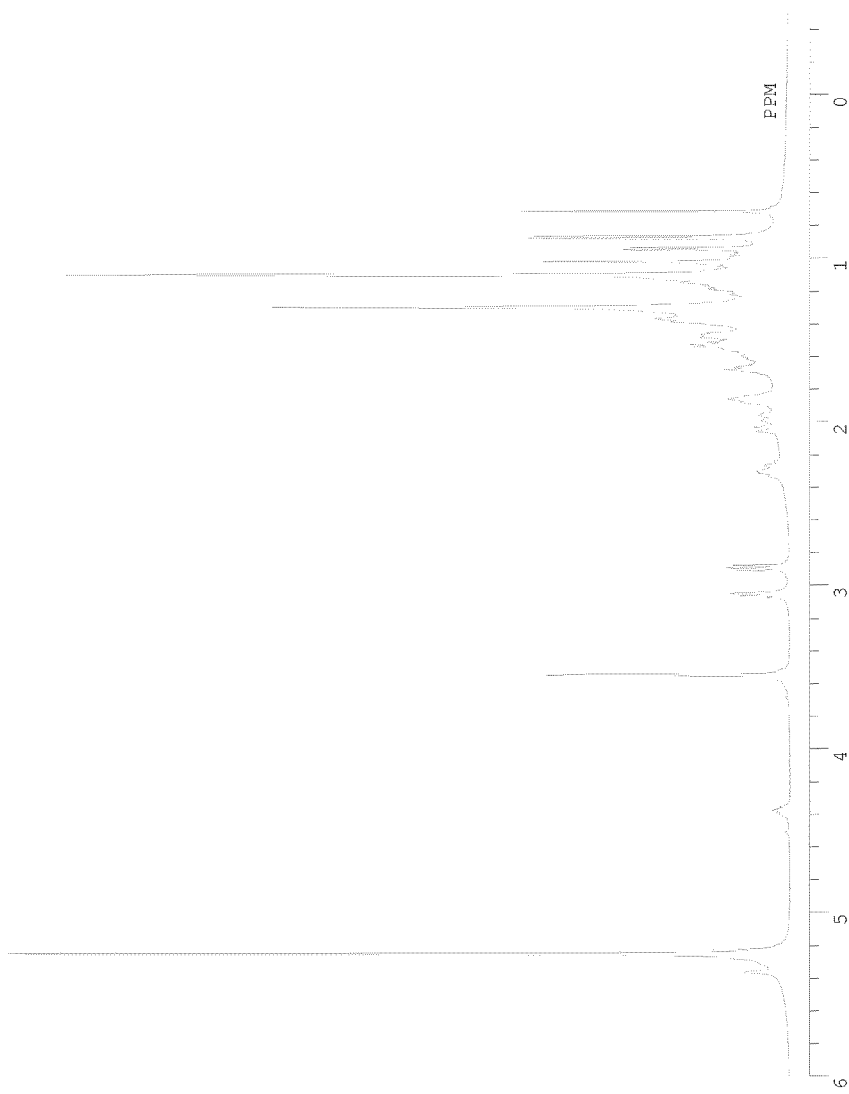
FIG. 4 is one example of the $^1$H-NMR spectrum of cholesteryl 12-aminododecylcarbamate hydrochloride prepared in Example 1-4.

Except that 12-(t-butoxycarbonyl)amino-1-aminododecane (1.59 g, 5 mmol) was used in place of 6-(t-butoxycarbonyl)amino-1-aminohexane, the procedure of Example 1-1 was repeated to give a hydrochloride (1.0 g) of cholesteryl 12-aminododecylcarbamate (Chol-$C_{12}$). The $^1$H-NMR spectrum (JNM-ECA500 JEOL Ltd.; EtOH-$d_6$) of the product is shown in FIG. 4.

Example 2

Preparation of Cholesteryl Group-Introduced HA Derivative

Example 2-1

Conversion of Cation Exchange Resin into Tetrabutylammonium (TBA) Salt Form

DOWEX® 50WX-8-400 (Aldrich) was suspended in ultrapure water and the resin was washed about three times with ultrapure water by decantation. A 40 wt % aqueous solution of tetrabutylammonium hydroxide (TBA-OH) (Aldrich) was added in an amount of about 1.5-fold molar equivalents relative to the cation exchange capacity of the resin, followed by stirring for about 30 minutes. After removing the excess of the TBA-OH solution by decantation, the resin was further washed with an excessive amount of ultrapure water to give a TBA salt of the cation exchange resin.

Example 2-2

Preparation of TBA Salt of HA

Hyaluronic acid sodium salt (HA-Na, Shiseido Co., Ltd.) having a molecular weight of 27 kDa, 50 kDa, or 100 kDa was dissolved in ultrapure water at a concentration of 15 mg/mL. A suspension of the TBA salt of the cation exchange resin obtained in Example 2-1 was added in an amount of 5-fold molar equivalents relative to HA units (unit molecular weight: 401.3), calculated as the ion exchange capacity of the resin. After stirring for 15 minutes, filtration was performed with a 0.45 μm filter and the filtrate was lyophilized to give hyaluronic acid TBA salt (HA-TBA) as a white solid.

Figure 5:
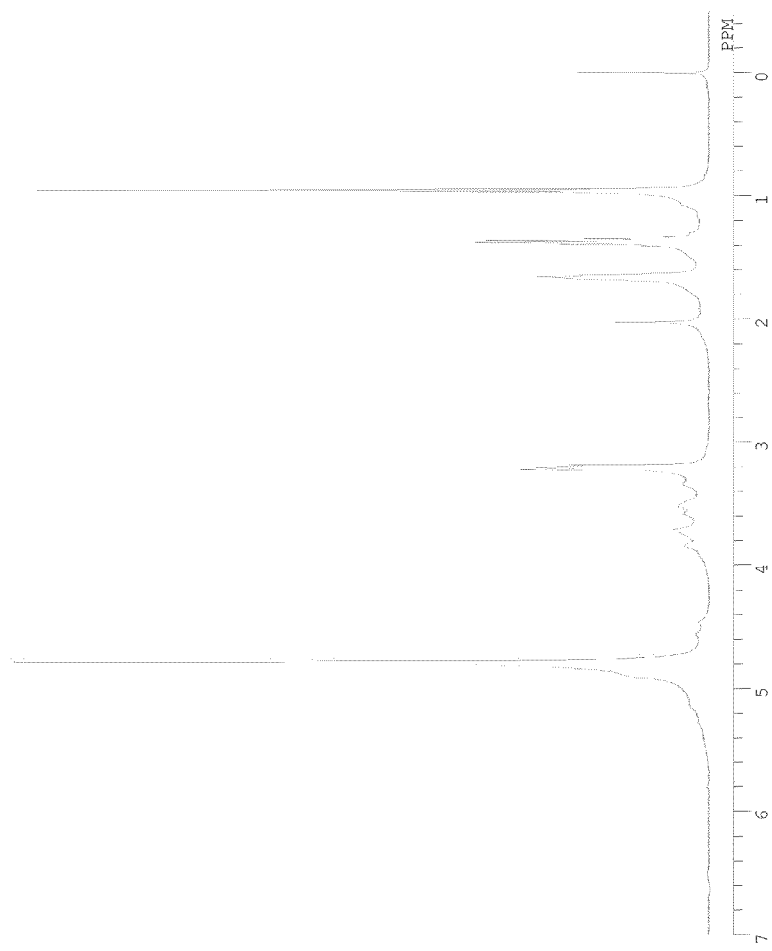
FIG. 5 is one example of the $^1$H-NMR spectrum of a hyaluronic acid tetrabutylammonium salt prepared in Example 2-2 using 50 kDa of sodium hyaluronate salt as a starting material.

As an exemplary example, the $^1$H-NMR spectrum (JNM-ECA500 JEOL Ltd.; EtOH-$d_6$) of the product prepared using 50 kDa of HA-Na as a starting material is shown in FIG. 5. The amount ratio of TBA to HA units was calculated from the integrated value for acetyl group in glucosamine (COCH$_3$, 2.0 ppm; 3H) and the integrated value for two methylenes in TBA (N(CH$_2$CH$_2$CH$_2$CH$_3$)$_4$, 1.3 to 1.8 ppm; 16H), and the unit average-molecular weight of HA-TBA was calculated from the ratio. For example, HA-TBA prepared using 50 kDa of HA-Na as a starting material had a unit-average molecular weight of 692.5.

Example 2-3

Preparation of Cholesteryl Group-Introduced HA Derivative

Example 2-3-1

Preparation of Cholesteryl 6-Aminohexylcarbamate-Introduced HA Derivative

An anhydrous DMSO solution of HA-TBA (10 mg/mL) prepared in Example 2-2 using HA-Na (50 kDa) as a starting material was prepared. Then, the Chol-$C_6$ hydrochloride prepared in Example 1-1 was added to each solution at the ratio relative to HA-TBA units indicated in Table 1 below. Thereafter, 4-(4,6-dimethoxy-1,3,5-triazine-2-yl)-4-methylmorpholinium chloride (DMT-MM) was added at the ratio relative to HA-TBA units indicated in Table 1 and stirred overnight at room temperature. The reaction solution was dialyzed (SpectraPor 4, molecular weight cutoff (MWCO): 12 k to 14 kDa) successively against 0.3M ammonia acetate/DMSO solution, 0.15M NaCl aqueous solution, and ultrapure water, and the resulting dialysate was lyophilized to give an intended product (HA-$C_6$-Chol) as a white solid.

Figure 6:
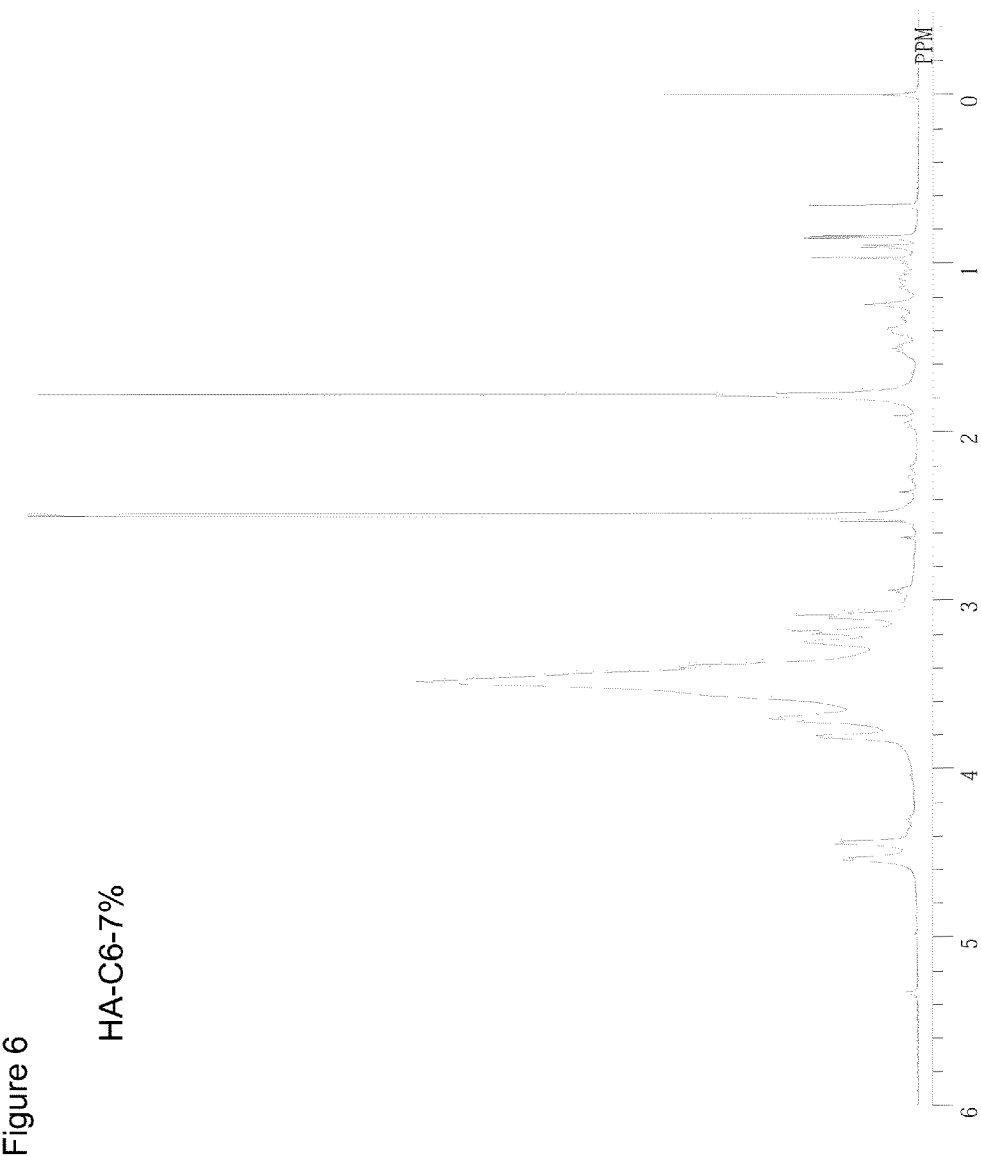
FIG. 6 is one example of the $^1$H-NMR spectrum of a cholesteryl 6-aminohexylcarbamate-introduced HA derivative (HA-$C_6$-Chol) prepared in Example 2-3-1.

The $^1$H-NMR spectrum (JNM-ECA500 JEOL Ltd.) of the product (introduction ratio 7%) using a 0.02N DCl DMSO-$d_6$/$D_2$O mixed solution (2N DCl $D_2$O:DMSO-$d_6$=1:99) as a measurement solvent is shown in FIG. 6. According to the formula shown below, the introduction ratio of cholesteryl groups relative to HA units was calculated from the integrated value for peaks derived from acetyl groups in glucosamine (COCH$_3$, 1.6 to 2.0 ppm; 3H) and the integrated value for peaks derived from methyl groups in cholesteryl groups (CH$_3$, 0.7 ppm; 3H) (Table 1). Note that since cholesteryl group-derived peaks (5H) are superposed on peaks near 1.6 to 2.0 ppm, which include peaks derived from acetyl groups of glucosamine, a value obtained by subtracting 5/3 of an integrated value for cholesteryl group methyl-derived peaks (0.7 ppm) from an integrated value for peaks near 1.6 to 2.0 ppm (i.e., integrated value (1.6 to 2.0 ppm)−integrated value (0.7 ppm)×5/3) was used as an integrated value for HA-derived acetyl groups in the calculation of the introduction ratio.

$$\text{Introduction ratio \%} = \frac{\text{Integrated value for methyl groups derived from cholesteryl groups (0.7 ppm)}}{\text{Integrated value for acetyl groups derived from } HA(1.6 \text{ to } 2.0 \text{ ppm, modified value})} \times 100 \quad \text{[Formula 7]}$$

TABLE 1

Amount of reagent used in the preparation of HA-$C_6$-Chol and introduction ratio

| Abbreviation | Added molar ratio of Chol-$C_6$ hydrochloride and DMT-MM (HA-TBA unit/DMT-MM/Chol-$C_6$) | Introduction ratio of Chol (unit %) |
|---|---|---|
| HA-$C_6$-Chol-2% | 100/2/2.2 | 2 |
| HA-$C_6$-Chol-3% | 100/4/4.4 | 3 |
| HA-$C_6$-Chol-6% | 100/6.5/7.2 | 6 |
| HA-$C_6$-Chol-7% | 100/8/8.8 | 7 |
| HA-$C_6$-Chol-15% | 100/16/17.6 | 15 |
| HA-$C_6$-Chol-18% | 100/20/22 | 18 |
| HA-$C_6$-Chol-21% | 100/24/26.4 | 21 |
| HA-$C_6$-Chol-25% | 100/28/30.8 | 25 |
| HA-$C_6$-Chol-27% | 100/32/35.2 | 27 |
| HA-$C_6$-Chol-34% | 100/40/44 | 34 |
| HA-$C_6$-Chol-42% | 100/50/55 | 42 |
| HA-$C_6$-Chol-50% | 100/60/66 | 50 |

Example 2-3-2

Preparation of HA Derivative Modified with Cholesteryl 2-Aminoethylcarbamate

Figure 7:
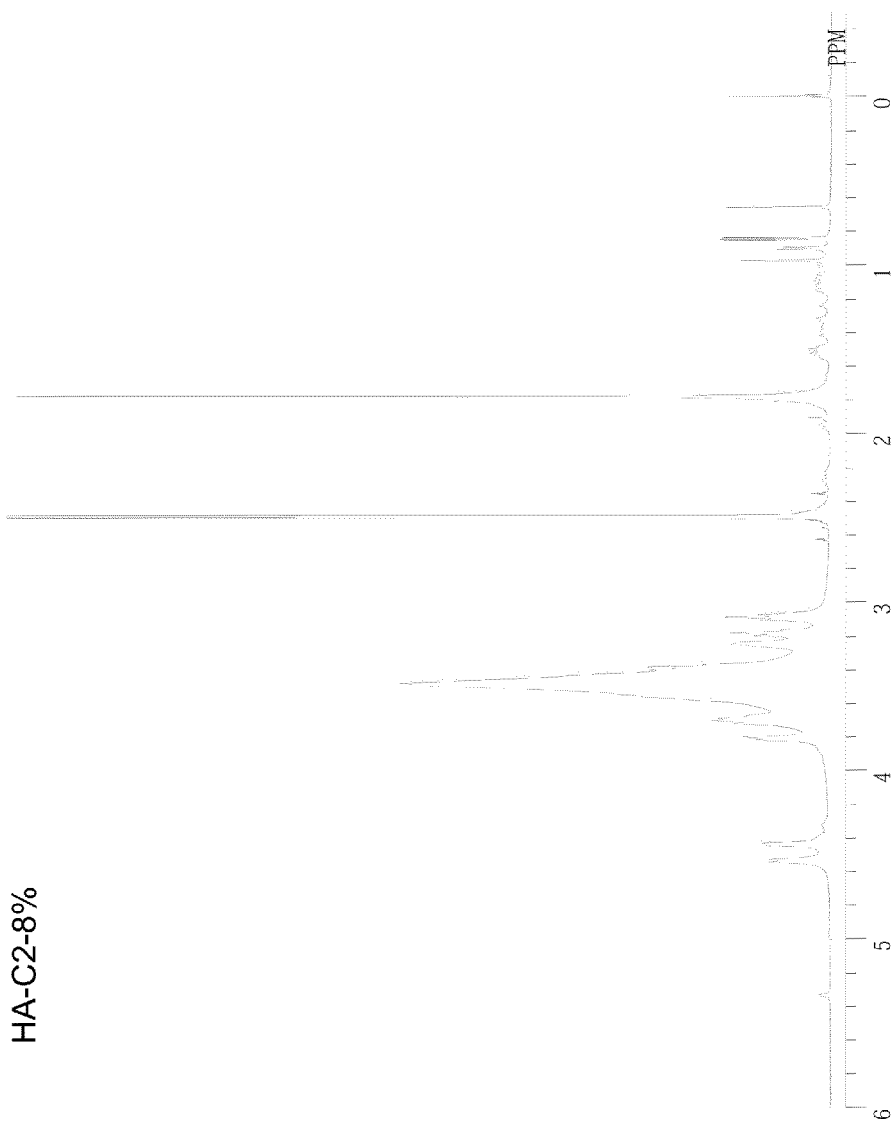
FIG. 7 is one example of the $^1$H-NMR spectrum of a cholesteryl 2-aminoethylcarbamate-introduced HA derivative (HA-$C_2$-Chol) prepared in Example 2-3-2.

HA-TBA prepared in Example 2-2 using HA-Na (50 kDa) as a starting material was dissolved at 10 mg/mL in anhydrous DMSO. Thereafter, the Chol-$C_2$ hydrochloride prepared in Example 1-2 was added to each solution at the ratio relative to HA-TBA units indicated in Table 2 below. Then, DMT-MM was added at the ratio relative to HA-TBA units indicated in Table 2 below and stirred overnight at room temperature. Sodium nitrate was added to the reaction solution to 0.3M, and isopropyl alcohol (IPA) was added. The resulting precipitate was recovered, washed with IPA and ethanol. Thereafter, the precipitate was dissolved in ultrapure water and dialyzed successively against 0.15M NaCl aqueous solution and ultrapure water (SpectraPor 4, molecular weight cutoff (MWCO): 12 k-14 kDa). The resulting dialysate was lyophilized to give HA-$C_2$-Chol as a white solid. HA-$C_2$-Chol can also be obtained by subjecting the above reaction solution to the same treatment as that in Example 2-3-1 (lyophillization of the dialysate obtained by dialysis successively against 0.3M ammonia acetate/DMSO solution, 0.15M NaCl aqueous solution, and ultrapure water). The $^1$H-NMR spectrum of the product (introduction ratio 8%) as measured under the same conditions as those in Example 2-3-1 is shown in FIG. 7. The introduction ratio of cholesteryl groups relative to HA units calculated according to the formula indicated in Example 2-3-1 is shown in Table 2.

TABLE 2

Amount of reagent used in the preparation of HA-$C_2$-Chol and introduction ratio

| Abbreviation | Added molar ratio of Chol-$C_2$ hydrochloride and DMT-MM (HA-TBA unit/DMT-MM/Chol-$C_2$) | Introduction ratio of Chol (unit %) |
|---|---|---|
| HA-$C_2$-Chol-2% | 100/2.2/2.4 | 2 |
| HA-$C_2$-Chol-4% | 100/4.4/4.8 | 4 |
| HA-$C_2$-Chol-8% | 100/8.8/9.7 | 8 |
| HA-$C_2$-Chol-16% | 100/16/17.6 | 16 |
| HA-$C_2$-Chol-20% | 100/20/22 | 20 |
| HA-$C_2$-Chol-24% | 100/24/26.4 | 24 |

TABLE 2-continued

Amount of reagent used in the preparation of HA-$C_2$-Chol and introduction ratio

| Abbreviation | Added molar ratio of Chol-$C_2$ hydrochloride and DMT-MM (HA-TBA unit/DMT-MM/Chol-$C_2$) | Introduction ratio of Chol (unit %) |
|---|---|---|
| HA-$C_2$-Chol-30% | 100/32/35.2 | 30 |
| HA-$C_2$-Chol-42% | 100/50/55 | 42 |

Example 2-3-3

Preparation of HA Derivative Modified with Cholesteryl 8-Aminooctylcarbamate

Figure 8:
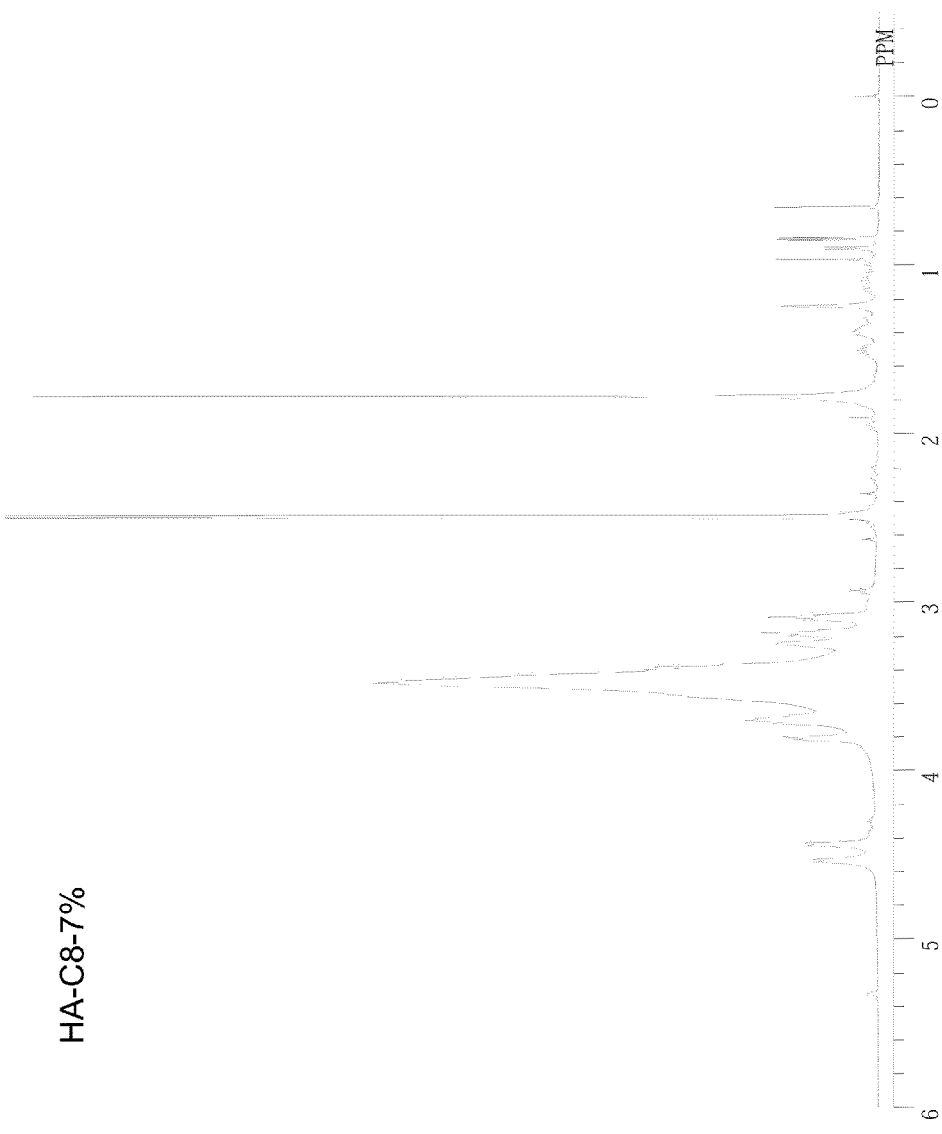
FIG. 8 is one example of the $^1$H-NMR spectrum of a cholesteryl 8-aminooctylcarbamate-introduced HA derivative (HA-$C_8$-Chol) prepared in Example 2-3-3.

Except that the Chol-$C_8$ hydrochloride prepared in Example 1-3 was used in place of Chol-$C_2$ hydrochloride, and Chol-$C_8$ hydrochloride and DMT-MM were added at the ratio indicated in Table 3 below, the procedure of Example 2-3-2 was repeated to give HA-$C_8$-Chol as a white solid. The $^1$H-NMR spectrum of the product (introduction ratio 7%) as measured under the same conditions as those in Example 2-3-1 is shown in FIG. 8. The introduction ratio of cholesteryl groups relative to HA units calculated according to the formula indicated in Example 2-3-1 is shown in Table 3.

TABLE 3

Amount of reagent used in preparation of HA-$C_8$-Chol and introduction ratio

| Abbreviation | Added molar ratio of Chol-$C_8$ hydrochloride and DMT-MM (HA-TBA unit/DMT-MM/Chol-$C_8$) | Introduction ratio of Chol (unit %) |
|---|---|---|
| HA-$C_8$-Chol-2% | 100/2/2.2 | 2 |
| HA-$C_8$-Chol-3% | 100/4/4.4 | 3 |
| HA-$C_8$-Chol-7% | 100/8/8.8 | 7 |

Example 2-3-4

Preparation of HA Derivative Modified with Cholesteryl 12-Aminododecylcarbamate

Figure 9:
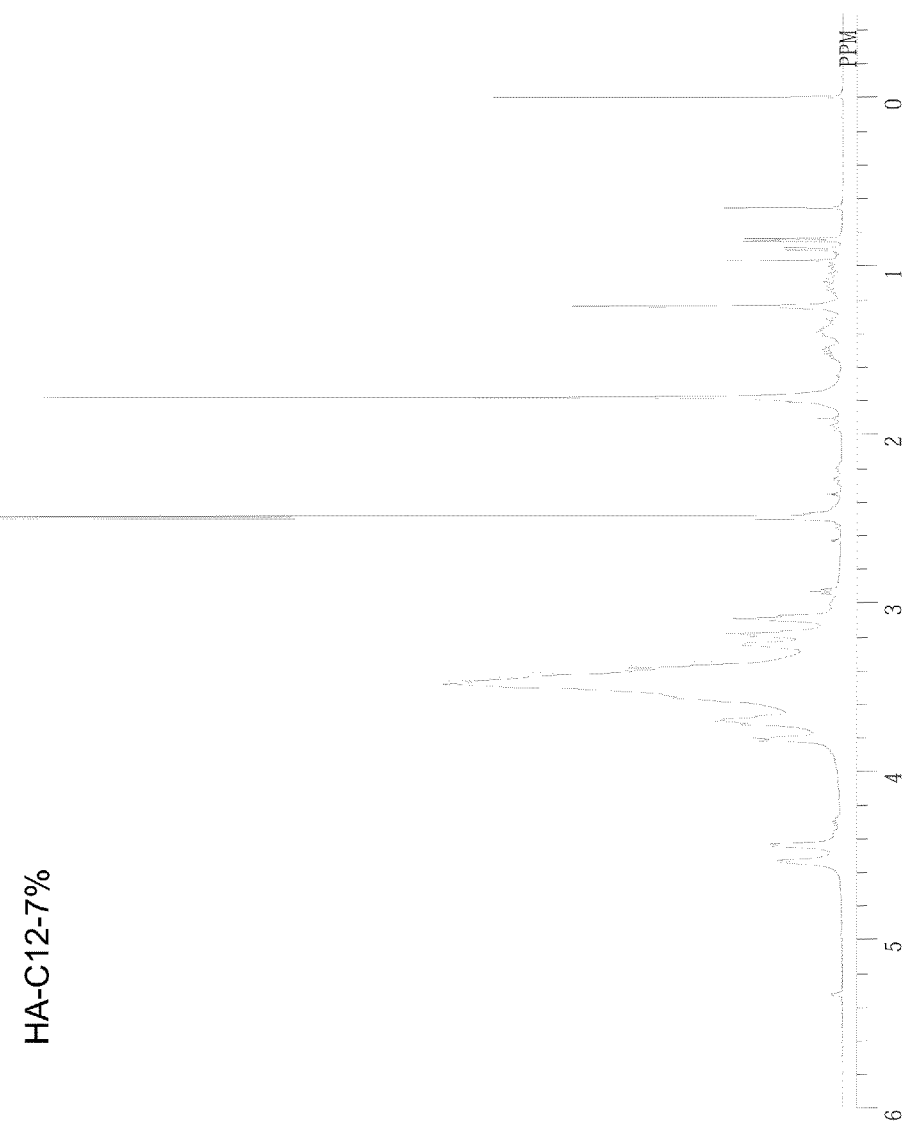
FIG. 9 is one example of the $^1$H-NMR spectrum of a cholesteryl 12-aminododecylcarbamate-introduced HA derivative (HA-$C_{12}$-Chol) prepared in Example 2-3-4.

Except that the Chol-$C_{1-2}$ hydrochloride prepared in Example 1-4 was used in place of Chol-$C_2$ hydrochloride, and Chol-$C_{1-2}$ hydrochloride and DMT-MM were added at the ratio indicated in Table 4 below, the procedure of Example 2-3-2 was repeated to give HA-$C_{12}$-Chol as a white solid. The $^1$H-NMR spectrum of the product (introduction ratio 7%) as measured under the same conditions as those in Example 2-3-1 is shown in FIG. 9. The introduction ratio of cholesteryl groups relative to HA units calculated according to the formula indicated in Example 2-3-1 is shown in Table 4.

TABLE 4

Amount of reagent used in preparation of HA-$C_{12}$-Chol and introduction ratio

| Abbreviation | Added molar ratio of Chol-$C_{12}$ hydrochloride and DMT-MM (HA-TBA unit/DMT-MM/Chol-$C_{12}$) | Introduction ratio of Chol (unit %) |
|---|---|---|
| HA-$C_{12}$-Chol-2% | 100/2/2.2 | 2 |
| HA-$C_{12}$-Chol-3% | 100/4/4.4 | 3 |
| HA-$C_{12}$-Chol-7% | 100/8/8.8 | 7 |
| HA-$C_{12}$-Chol-16% | 100/16/17.6 | 16 |
| HA-$C_{12}$-Chol-19% | 100/20/22 | 19 |
| HA-$C_{12}$-Chol-23% | 100/24/26.4 | 23 |
| HA-$C_{12}$-Chol-30% | 100/32/35.2 | 30 |
| HA-$C_{12}$-Chol-43% | 100/50/55 | 43 |

Example 3

Figures 1, 10:
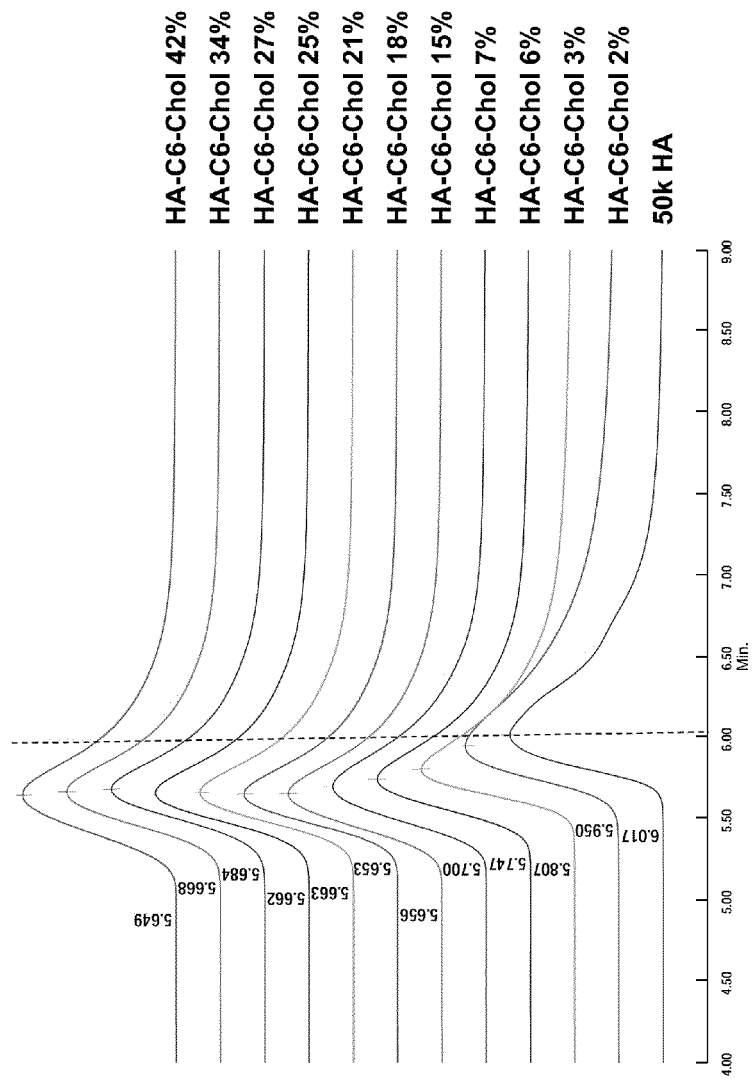
Figures 2, 10:
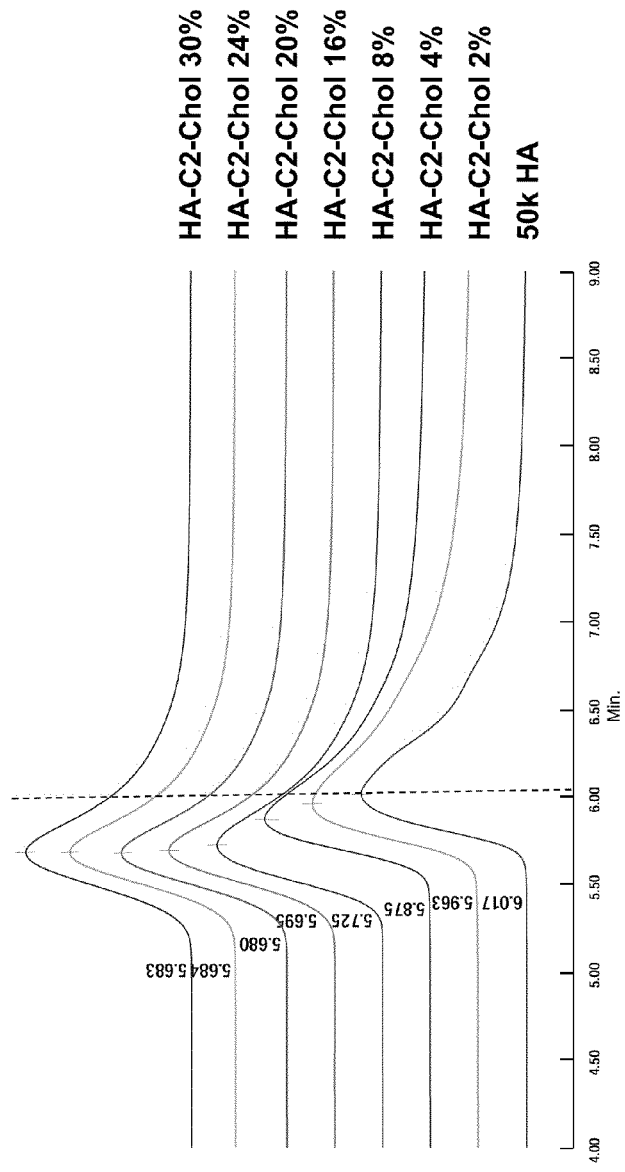
Figures 3, 10:
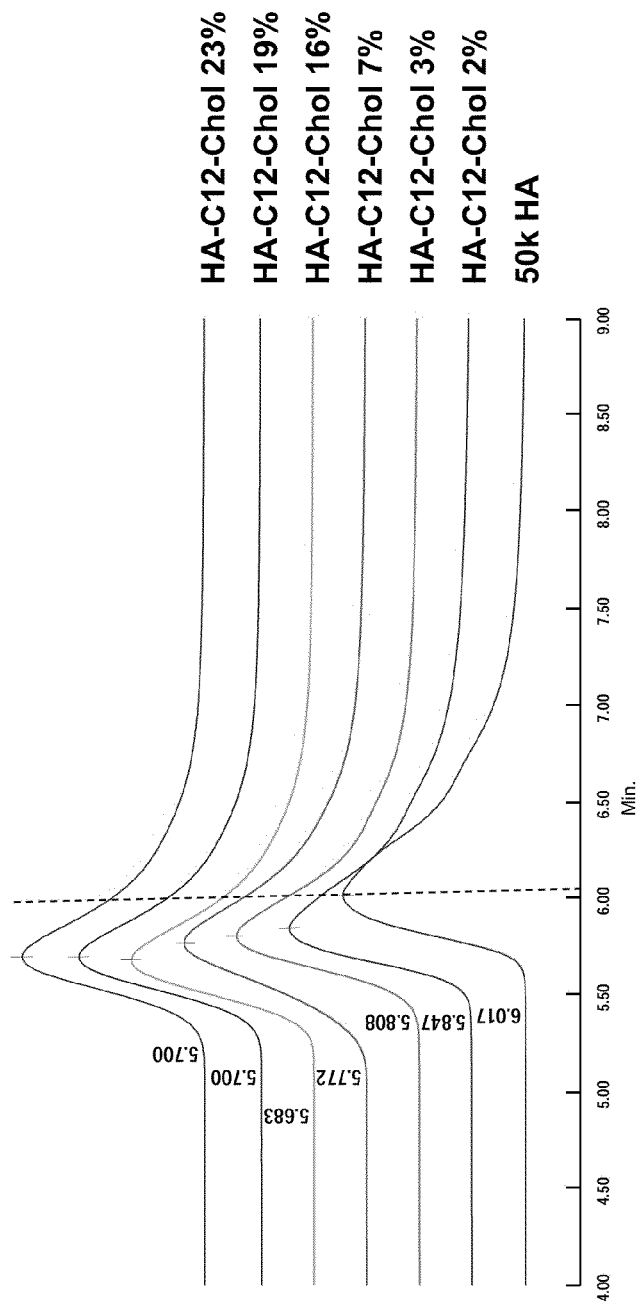
Figures 4, 10:
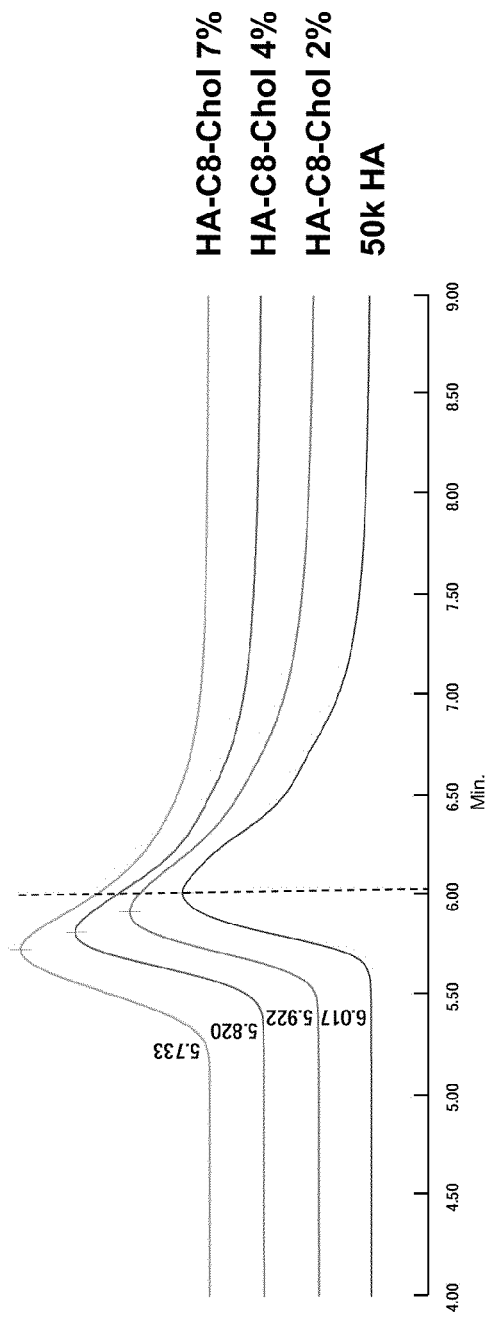

Confirmation of Formation of Association Product by Size Exclusion Chromatography Using PBS Each of the HA derivatives obtained in Examples 2-3-1 to 2-3-4 was dissolved at a concentration of 1 mg/mL in distilled water (ultrapure water). Each of them was subjected to size exclusion chromatography (SEC), and formation of an association product was observed from changes in retention time of the HA derivative (FIGS. 10-1 to 10-4). SEC conditions were as follows.
Column: G3000SWXL (Tosoh Corporation, Japan)
Eluent: PBS (pH 7.4)
Flow rate: 1 mL/min
Amount of injection: 50 μL
Detection: Differential refractive index.

Example 4

Figures 1, 11:
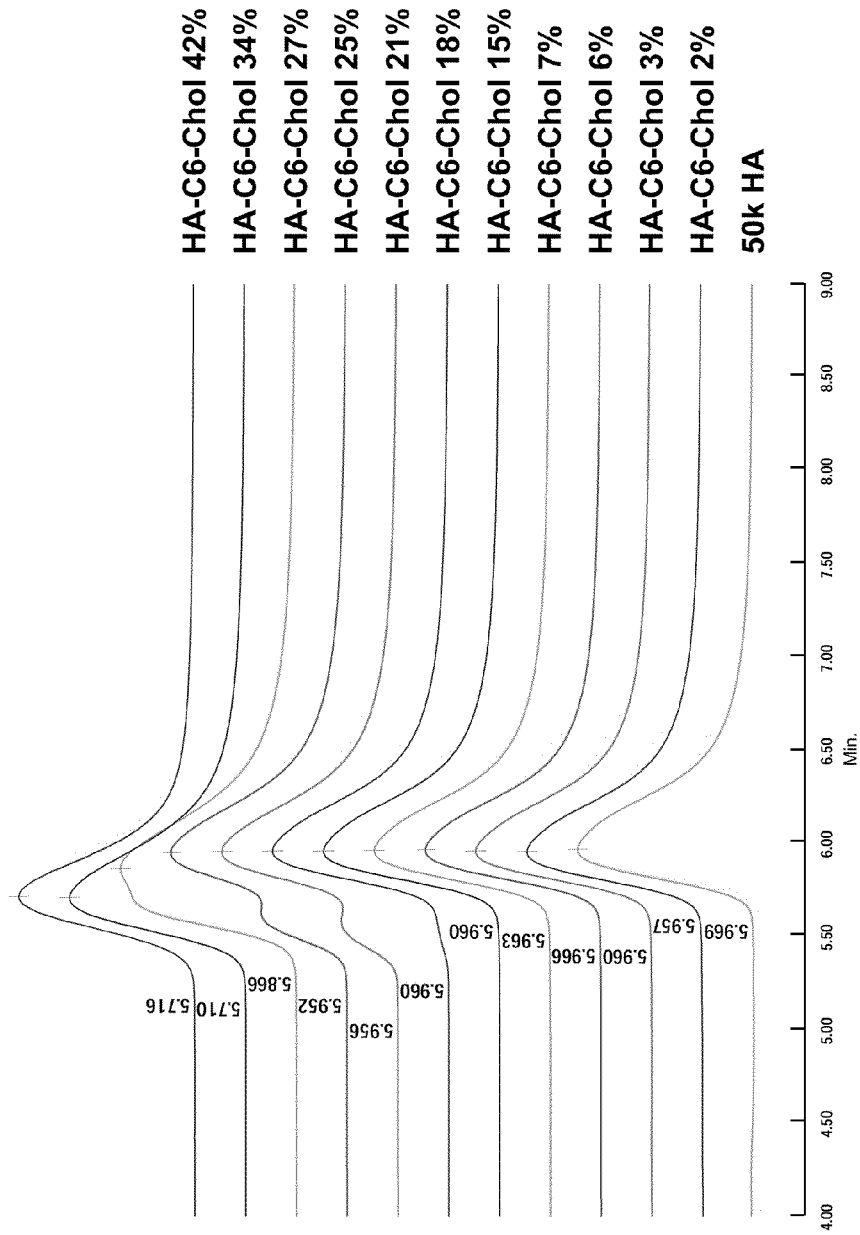
Figures 2, 11:
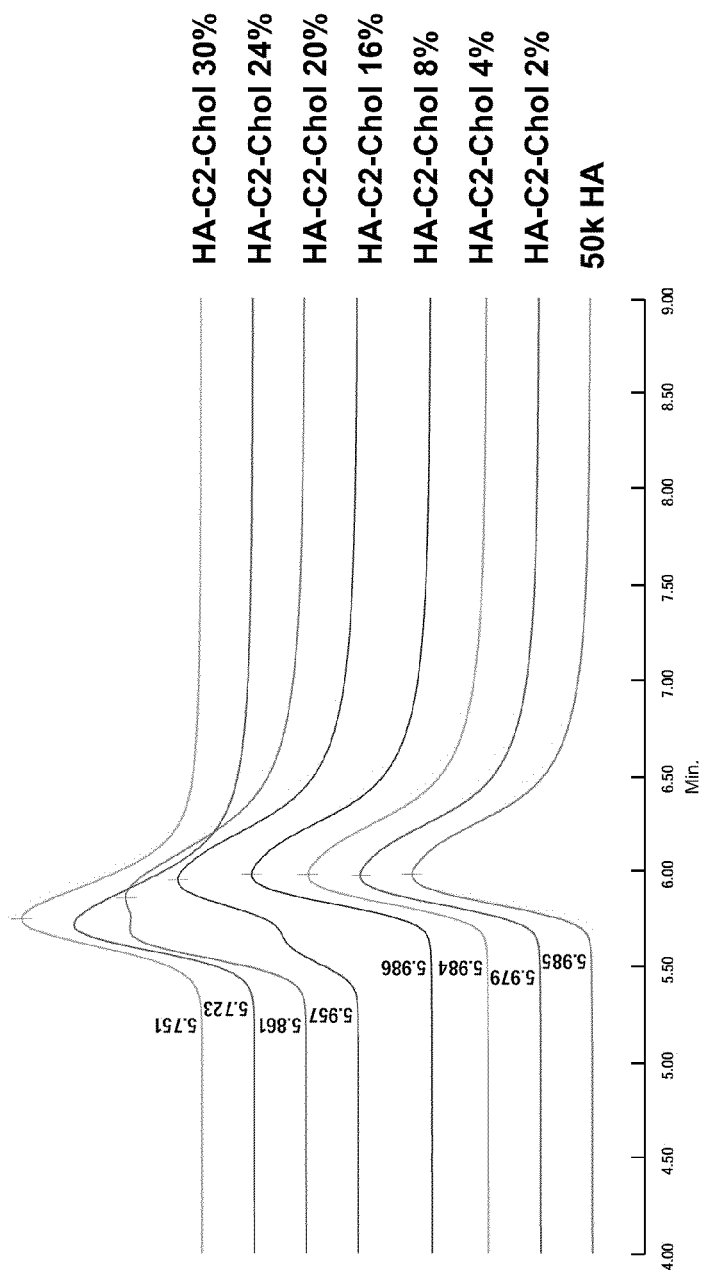
Figures 3, 11:
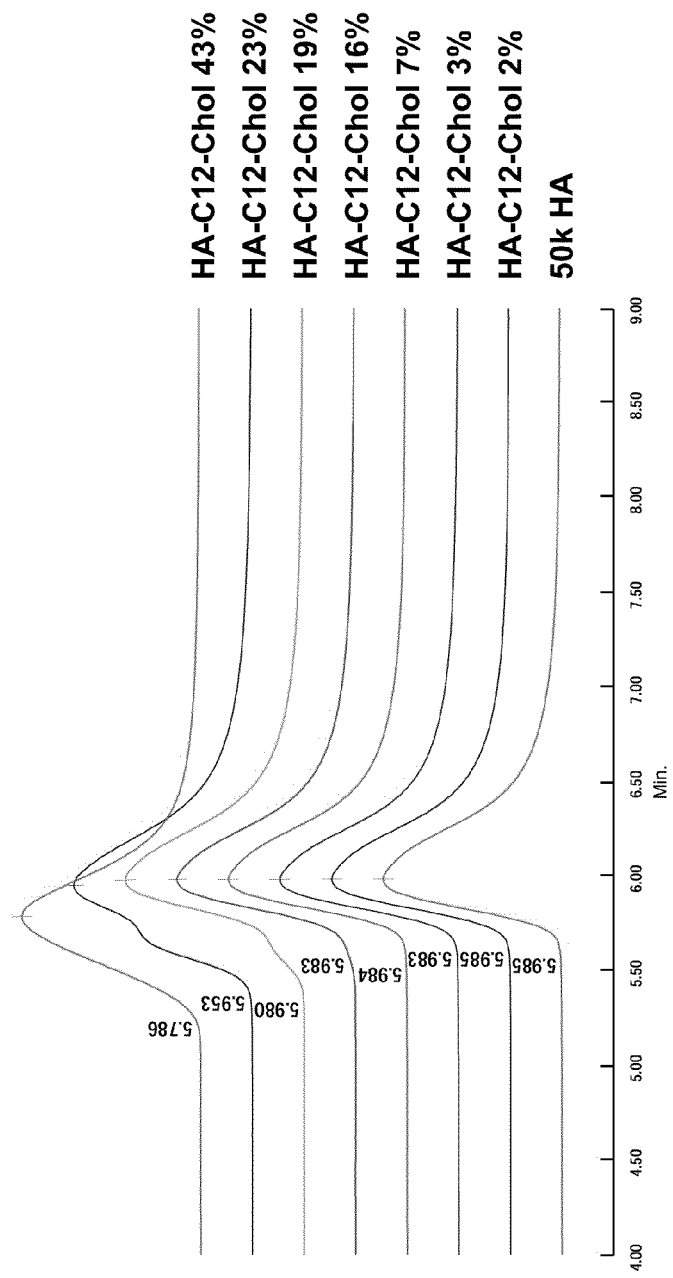
Figures 4, 11:
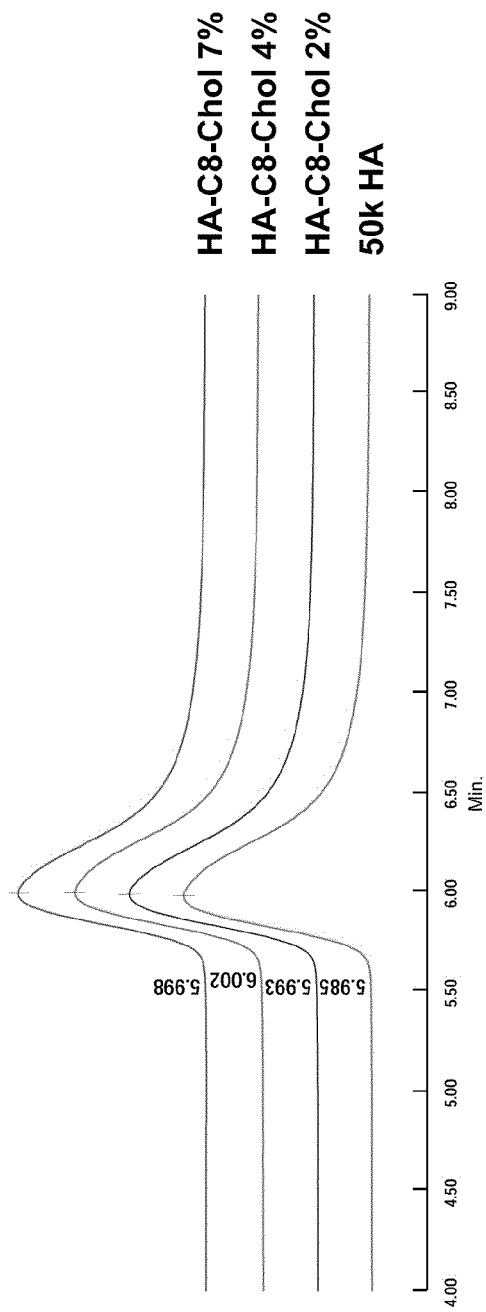

Confirmation of Decay of Association Product by Size Exclusion Chromatography Using hydroxypropyl-β-cyclodextrin-Added PBS Each of the HA derivatives obtained in Examples 2-3-1 to 2-3-4 was dissolved at a concentration of 1 mg/mL in distilled water (ultrapure water). A hydroxypropyl-β-cyclodextrin (HP-β-CD) PBS solution (33 mM, 30 μL) was added to each 70 μL HA derivative and then incubated at 37° C. for 1 hour. Each sample was subjected to size exclusion chromatography (SEC), and decay of an association product of the HA derivative was observed from changes in retention time (FIGS. 11-1 to 11-4).
SEC conditions were as follows.
Column: G3000SWXL (Tosoh Corporation, Japan)
Eluent: 10 mM HP-β-CD/PBS (pH 7.4)
Flow rate: 1 mL/min
Amount of injection: 50 μL
Detection: Differential refractive index.

While elution of HA derivative was faster than that of raw material HA in SEC using PBS (Example 3), they were the same in SEC using HP-β-CD (Example 4). From the results, it is considered that the HA derivative of the present invention, like CHP, forms a multimolecularassociative particle in the aqueous solution using hydrophobic interaction of cholesteryl groups as a driving force. HA-$C_6$-Chol of 18% or greater (FIG. 11-1), HA-$C_2$-Chol of 16% or greater (FIG. 11-2), and HA-$C_{12}$-Chol of 19% or greater (FIG. 11-3) had a peak at an early elution time in SEC using HP-β-CD; this is considered as a peak corresponding to the multimolecular associative particle. From the results it was confirmed that the HA derivative of the present invention was capable of forming an associative particle which was stable enough not to be decayed completely under the above HP-β-CD-added conditions, suggesting that the particle is useful as a carrier for holding a drug stably in blood and in the subcutis.

Example 5

Preparation of Complex of Cholesteryl Group-Introduced HA Derivative and Protein (Erythropoietin)

Each of the HA derivatives obtained in Examples 2-3-1 to 2-3-4 was dissolved at a concentration of 1 mg/mL in distilled water (ultrapure water). As a comparative example, HA-Na (molecular weight: 50 kDa) used as a raw material in Example 2-2, and cholesteryl-introduced pullulan (CHP; trade name PUREBRIGHT CP-100T, NOF Corporation, Japan) in which 1.38 —CONH—$(CH_2)_6$—NHCOO— cholesteryl groups per 100 monosaccharides in pullulan (molecular weight 100 kDa) were introduced in hydroxy thereof was dissolved at a concentration of 1 mg/mL in distilled water (ultrapure water).

To an aqueous solution (2 mg/mL, 50 μL) of erythropoietin (EPO), concentrated PBS (50 μL) was added to give a final concentration of 1×PBS, and then the HA derivative (1 mg/mL, 100 μL) was added. After incubation at 37° C. for 24 hours, the mixture was subjected to centrifugal separation at 2000 G, and the supernatant in which all free EPO and dispersible complex were present was subjected to size exclusion chromatography. From the results of chromatography, the amount of free EPO that was not incorporated into the complex and thus remained in the aqueous solution was calculated, and the amount of EPO contained in the complex was calculated. Further, the amount of EPO contained in the complex per unit weight of the HA derivative (complexation %; (weight of EPO in the complex/weight of HA derivative)× 100) was calculated. The results are shown in Table 5 below. An exemplary chromatogram is shown in an upper part of FIG. 12.
SEC Measurement Conditions No. 1
Column: G4000SWXL (Tosoh Corporation, Japan)
Eluent: PBS (pH 7.4)
Flow rate: 1 mL/min
Amount of injection: 50 μL
Detection: UV (280 nm).
SEC Measurement Conditions No. 2
Column: QC-PAK-GFC300 (Tosoh Corporation, Japan)
Eluent: PBS (pH 7.4)
Flow rate: 1.2 mL/min
Amount of injection: 20 μL
Detection: UV (280 nm).

TABLE 5

Results of preparation of HA derivative-erythropoietin the complex

| Abbreviation | Introduction ratio % | Complexation % |
|---|---|---|
| 50k HA-Na | 0 | 0 |
| HA-$C_2$-Chol-2% | 2 | 28 |
| HA-$C_2$-Chol-4% | 4 | 55 |
| HA-$C_6$-Chol-2% | 2 | 30 |
| HA-$C_6$-Chol-3% | 3 | 54 |
| HA-$C_8$-Chol-2% | 2 | 25 |

TABLE 5-continued

Results of preparation of HA derivative-erythropoietin the complex

| Abbreviation | Introduction ratio % | Complexation % |
|---|---|---|
| HA-C$_8$-Chol-3% | 3 | 58 |
| HA-C$_{12}$-Chol-2% | 2 | 38 |
| HA-C$_{12}$-Chol-3% | 3 | 62 |
| CHP | 3 | 18 |

As to the introduction ratio of the cholesteryl-introduced pullulan (CHP), a ratio of introduction per 1 unit of disaccharide of pullulan is indicated as the introduction ratio for the purpose of comparison with the HA derivatives. The introduction ratio was calculated from the number of cholesteryl groups (1.38 cholesteryl groups) introduced per 100 monosaccharides, which was indicated on the purchased product.

The value of complexation % of the HA derivative of the present invention was about 3-fold higher than that of CHP; it was confirmed that the HA derivative of the present invention efficiently formed a complex with EPO.

Example 6

Analysis of Erythropoietin Released from Complex

To each sample (200 μL) incubated at 37° C. for 24 hours in Example 5, a hydroxypropyl-β-cyclodextrin (HP-β-CD) PBS solution (50 mM, 50 μL) was added and incubated at 37° C. for 1 hour. Each sample was subjected to size exclusion chromatography. The concentration of free EPO including EPO released from the complex (the concentration was calculated using a calibration curve prepared from a standard sample of EPO) was calculated from the EPO peak area. The recovery ratio (%; weight of free EPO/initial weight of EPO× 100) is shown in Table 6 below. An exemplary chromatogram is shown in a lower part of FIG. 12.
SEC Measurement Conditions
Column: G4000SWXL (Tosoh Corporation, Japan)
Eluent: 10 mM HP-β-CD/PBS (pH 7.4)
Flow rate: 1 mL/min
Amount of injection: 50 μL
Detection: UV (280 nm)

TABLE 6

Amount of EPO recovered after addition of HP-β-CD

| Abbreviation | Introduction ratio % | Recovery ratio (%) |
|---|---|---|
| EPO only | — | 100 |
| 50k HA-Na | 0 | 100 |
| HA-C$_2$-Chol-2% | 2 | 100 |
| HA-C$_2$-Chol-4% | 4 | 99 |
| HA-C$_6$-Chol-2% | 2 | 101 |
| HA-C$_6$-Chol-3% | 3 | 100 |
| HA-C$_8$-Chol-2% | 2 | 100 |
| HA-C$_8$-Chol-3% | 3 | 99 |
| HA-C$_{12}$-Chol-2% | 2 | 100 |
| HA-C$_{12}$-Chol-3% | 3 | 99 |
| CHP | 3 | 100 |

From the size exclusion chromatography, it was confirmed that EPO released upon the decay of the associative particle of the HA derivative by addition of HP-β-CD was in an intact state. Accordingly, it was confirmed that the HA derivative of the present invention formed a complex, held the protein in the complex, and thereafter released the protein while keeping the protein in a stable state.

Example 7

Precipitability and Dispersibility of Cholesteryl Group-Introduced HA Derivative Example 7-1

Behavior at the Physiological Salt Concentration

Figure 13:
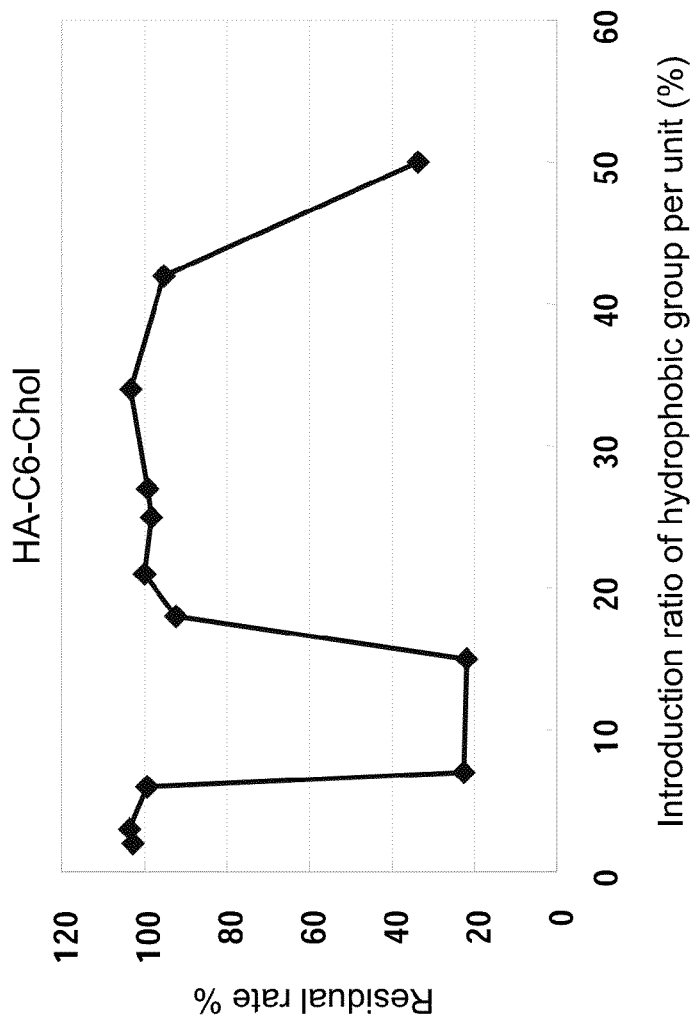
FIG. 13 is a graph of the residual ratio of the HA derivative in the solution calculated in Example 7-1 against the introduction ratio of hydrophobic groups of the HA derivative.

The HA derivative obtained in Example 2-3-1 was dissolved at a concentration of 6 mg/mL in distilled water (ultrapure water). A concentrated buffer solution was added to give a final buffer solution composition of 10 mM PB (pH 7.4) and 150 mM NaCl, and the HA derivative concentration was set to 4.5 mg/mL. After incubation at 37° C. for 20 minutes, the mixture was subjected to centrifugal separation at 2000 G for 1 minute. The supernatant was diluted 2-fold with HP-β-CD/PBS solution (250 mM), incubated for 2 hours, and then subjected to SEC. From the detected peak area of the HA derivative, the residual ratio of the HA derivative in the solution with respect to the initial amount used was calculated. The graph of the residual ratio against the introduction ratio of hydrophobic groups of the HA derivative is shown in FIG. 13.
SEC Measurement Conditions
Column: QC-PAK-GFC200 (Tosoh Corporation, Japan)
Eluent: 10 mM HP-β-CD/PBS (pH 7.4)
Flow rate: 1.2 mL/min
Amount of injection: 20 μL
Detection: Differential refractive index.

It was confirmed that the HA derivative having an introduction ratio of hydrophobic groups of 7 to 15% aggregated at the physiological salt concentration and formed a precipitate. This suggests that the HA derivative may be used as a carrier for a long-term sustained-release formulation which aggregates under the physiological salt concentration condition to thereby reside in the subcutis for a long period of time to enable sustained release of a protein or peptide. It was also confirmed that in the case of 18 to 42%, the HA derivative was stably dispersed even under the physiological salt concentration condition. This indicates that the HA derivative may be used as a systemic-administration type protein carrier.

Example 7-2

Effect of NaCl Concentration on Dispersibility of HA Derivative

Figure 14:
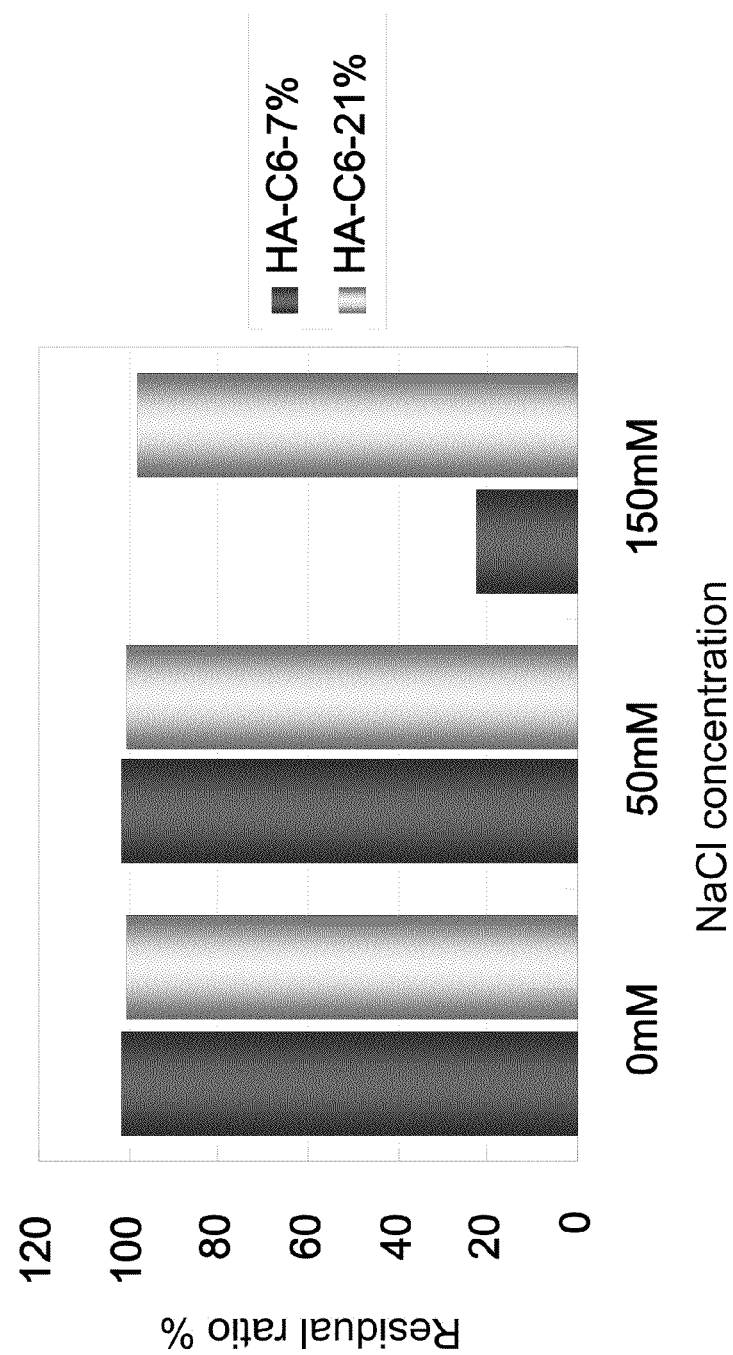
FIG. 14 is a graph of the residual ratio of the HA derivative in the solution calculated in Example 7-2 against the NaCl concentration.

The HA derivative obtained in Example 2-3-1 was dissolved at a concentration of 6 mg/mL in distilled water (ultrapure water). A concentrated buffer solution was added to give a final buffer solution composition of 10 mM PB and 0 mM NaCl or a final buffer solution composition of 10 mM PB and 50 mM NaCl, and the HA derivative concentration was set to 4.5 mg/mL. After incubation at 37° C. for 20 minutes, the mixture was centrifuged at 2000 G for 1 minute. The supernatant was diluted 2-fold with HP-β-CD/PBS solution (250 mM), incubated for 2 hours, and then subjected to SEC. From the detected peak area of the HA derivative, the residual ratio of the HA derivative in the solution with respect to the initial amount used was calculated. The graph of the residual ratio of each HA derivative against the salt concentration is shown in FIG. 14. Note that the SEC measurement conditions were the same as those in Example 7-1.

It was confirmed that the HA derivative having an introduction ratio of 7% showed salt concentration-dependent behaviors that while it was uniformly dispersed under conditions of a low salt concentration (10 mM PB pH 7.4, 0 or 50 mM NaCl), it was precipitated at the physiological salt concentration (150 mM). The results suggest that by preparing a solution of low salt concentration isotonized with sugar or the like, the HA derivative of the present invention may be used as a carrier for a formulation which precipitates in the subcutis after administration.

Further, it was confirmed that the HA derivative having an introduction ratio of 21% did not precipitate even at the physiological salt concentration, and was stably dispersed as in Example 7-1.

Example 8

Precipitability and Dispersibility of HA Derivative/Protein (Erythropoietin) Complex The HA derivative obtained in Example 2-3-1 and shown in Table 7 was dissolved at a concentration of 4 mg/mL in distilled water (ultrapure water). To an aqueous solution of erythropoietin (1 mg/mL, 25 μL), concentrated PBS (50 μL) was added to give a final concentration of 1×PBS, and then the HA derivative (4 mg/mL, 25 μL) was added. After incubation at 37° C. for 2 hours, the mixture was subjected to centrifugal separation at 2000 G. The supernatant was subjected to size exclusion chromatography, and a peak area of HA derivative-EPO complex present in the supernatant and a peak area of free EPO that was not incorporated into the complex were calculated. To obtain a peak area of EPO alone added in the present experiments and a peak area of HA derivative alone added in the present experiments, another solution was prepared and subjected to size exclusion chromatography. A percentage of the sum of the peak area of HA derivative-EPO complex present in the supernatant and the peak area of free EPO with respect to the sum of the peak area of added EPO alone and the peak area of added HA derivative alone was calculated as a residual ratio (Table 7). Note that in this experiment system, all EPO in a free state is present in the supernatant even after centrifugation and will not be precipitated.

$$\text{Residual ratio \%} = \frac{\text{Peak area of complex of } HA \text{ derivative and } EPO + \text{Peak area of free } EPO}{\text{Peak area of added } EPO + \text{Peak area of added } HA \text{ derivative}} \times 100 \quad \text{[Formula 8]}$$

Figure 15:
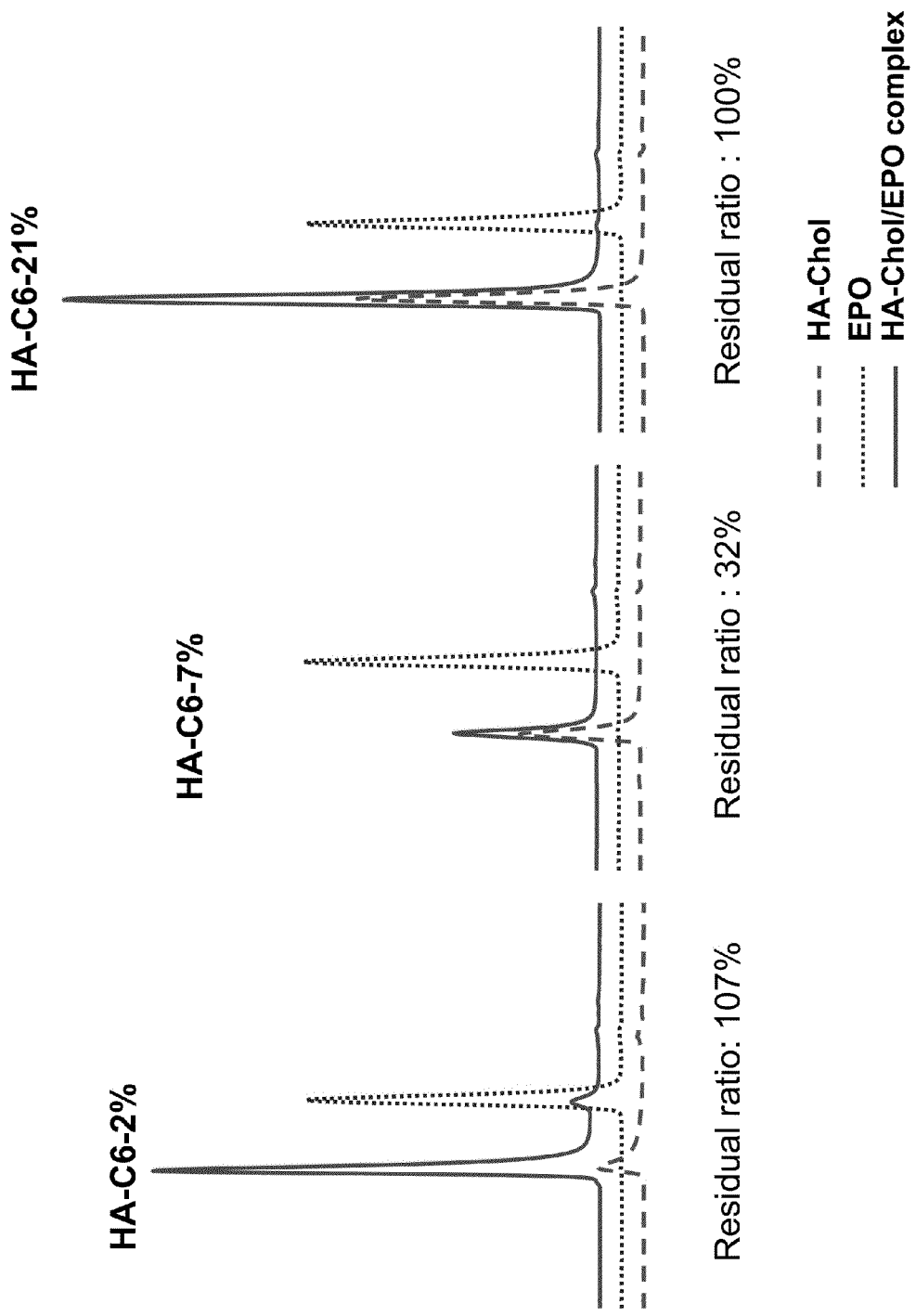
FIG. 15 is a chart of size exclusion chromatography measured in Example 8.

The chromatogram is shown in FIG. 15.

SEC Measurement Conditions

Column: QC-PAK-GFC300 (Tosoh Corporation, Japan)

Eluent: PBS (pH 7.4)

Flow rate: 1.2 mL/min

Amount of injection: 20 μL

Detection: UV (215 nm)

TABLE 7

Residual ratio of HA derivative and EPO

| Abbreviation | Introduction ratio % | Residual ratio (%) |
| --- | --- | --- |
| HA-$C_6$-Chol-2% | 2 | 107 |
| HA-$C_6$-Chol-7% | 7 | 32 |
| HA-$C_6$-Chol-21% | 21 | 100 |

In the cases of HA-$C_6$-Chol-2% and HA-$C_6$-Chol-21%, the residual ratio was about 100%; it was confirmed that the HA derivative/protein complex was a stable dispersive particle. In the case of HA-$C_6$-Chol-7%, the residual ratio was 32%; it was confirmed that the HA derivative/protein complex was precipitable. Specifically, the results show that the HA derivative of the present invention maintained its precipitability and dispersibility even after it formed the complex with the protein.

Example 9

Preparation of HA Derivative Modified with Cholesteryl 8-Amino-3,6-Dioxaoctylcarbamate

Example 9-1

Preparation of Cholesteryl 8-Amino-3,6-Dioxaoctylcarbamate Hydrochloride

To a solution of cholesteryl chloroformate (1.7 g, 4.7 mmol) in anhydride dichloromethane (50 mL), triethylamine (TEA, 0.53 mL) was added in an argon atmosphere and stirred. On ice, 8-(t-butoxycarbonyl)amino-3,6-dioxaoctylamine (0.59 mL, 2.5 mmol) was added by dropping, stirred on the ice for 30 minutes, and then heated to room temperature, and the mixture was stirred overnight. The reaction mixture was washed with ultrapure water and brine and then dried with anhydrous magnesium sulfate. Thereafter, the solvent was distilled off under reduced pressure. The resulting residue was purified by silica gel column chromatography (eluent: ethyl acetate:n-hexane=1:1). The fractions of an intended product were combined together, and the solvent was distilled off under reduced pressure.

Figure 16:
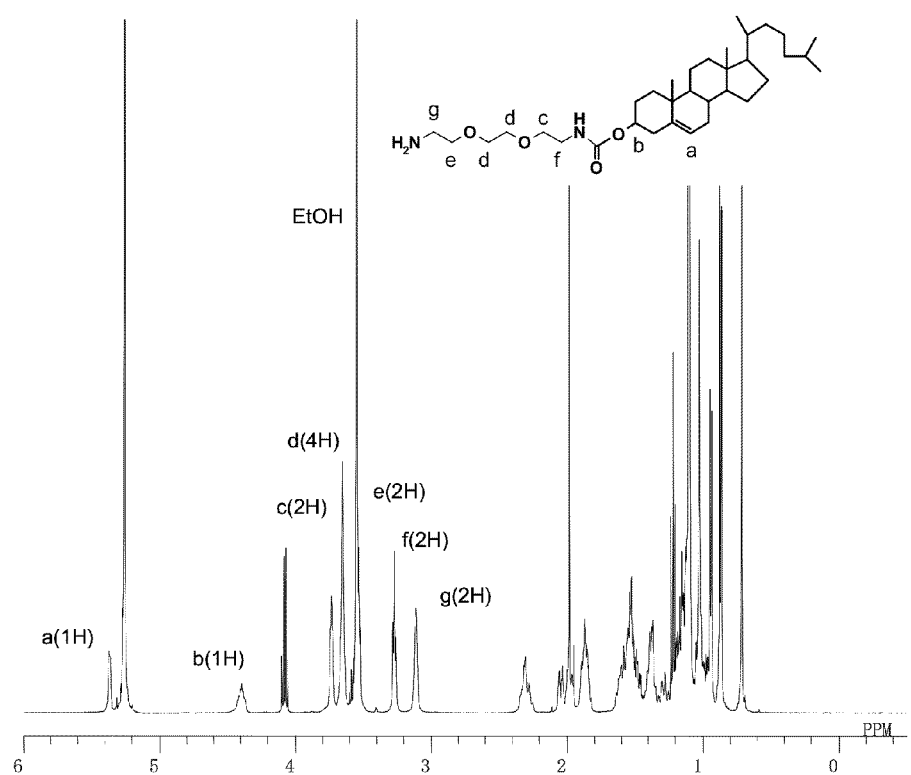
FIG. 16 is one example of the $^1$H-NMR spectrum of a cholesteryl 8-amino-3,6-dioxaoctylcarbamate (Chol-EO2) hydrochloride prepared in Example 9-1.

The resulting residue was dissolved in ethyl acetate (40 mL), and 4N hydrochloric acid/ethyl acetate solution (40 mL) was added and stirred overnight at room temperature. The resulting precipitate was recovered by centrifugal separation. The resulting solid was washed five times with ethyl acetate and then dried under reduced pressure to give a hydrochloride (1.3 g) of cholesteryl 8-amino-3,6-dioxaoctylcarbamate (Chol-EO2). The $^1$H-NMR spectrum (JNM-ECA500 JEOL Ltd.; MeOH-$d_4$) of the product is shown in FIG. 16.

Example 9-2

Figure 17:
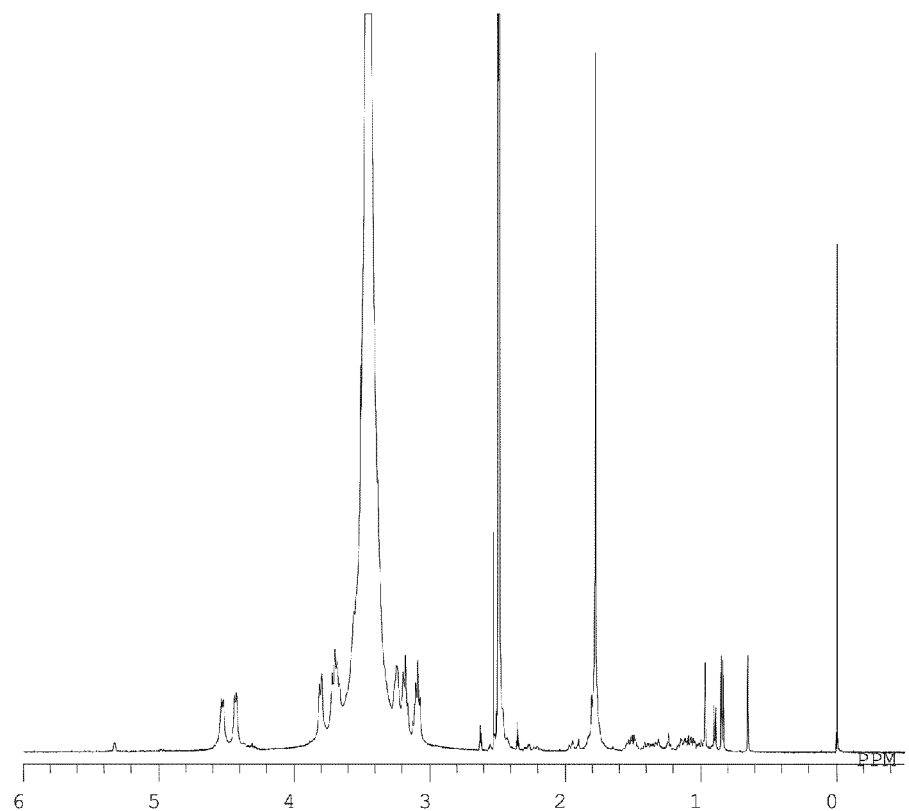
FIG. 17 is one example of the $^1$H-NMR spectrum of a cholesteryl 8-amino-3,6-dioxaoctylcarbamate-introduced HA derivative (HA-EO2-Chol) prepared in Example 9-2.

Preparation of HA Derivative Modified with Cholesteryl 8-Amino-3,6-Dioxaoctylcarbamate Except that the Chol-EO2 hydrochloride prepared in Example 9-1 was used in place of Chol-$C_6$ hydrochloride, and Chol-EO2 hydrochloride and DMT-MM were added at the ratio indicated in Table 8 below, the procedure of Example 2-3-1 was repeated to give HA-EO2-Chol as a solid. The $^1$H-NMR spectrum of the product (introduction ratio 7%) as measured under the same conditions as those in Example 2-3-1 is shown in FIG. 17. The introduction ratio of cholesteryl groups relative to HA units calculated according to the formula indicated in Example 2-3-1 is shown in Table 8.

TABLE 8

Amount of reagent used in synthesis of HA-EO2-Chol and results of synthesis

| Abbreviation | Added molar ratio of Chol-EO2 and DMT-MM (HA-TBA unit/DMT-MM/Chol-EO2) | Introduction ratio of Chol (unit %) |
|---|---|---|
| HA-EO2-Chol-2% | 100/2/2.2 | 2 |
| HA-EO2-Chol-3% | 100/4/4.4 | 3 |
| HA-EO2-Chol-7% | 100/8/8.8 | 7 |
| HA-EO2-Chol-14% | 100/16/17.6 | 14 |
| HA-EO2-Chol-22% | 100/24/26.4 | 22 |
| HA-EO2-Chol-31% | 100/40/44 | 31 |

Example 10

Preparation of HA Derivative Modified with 2-Aminoethyl Cholesteryl Disulfide

Figure 18:
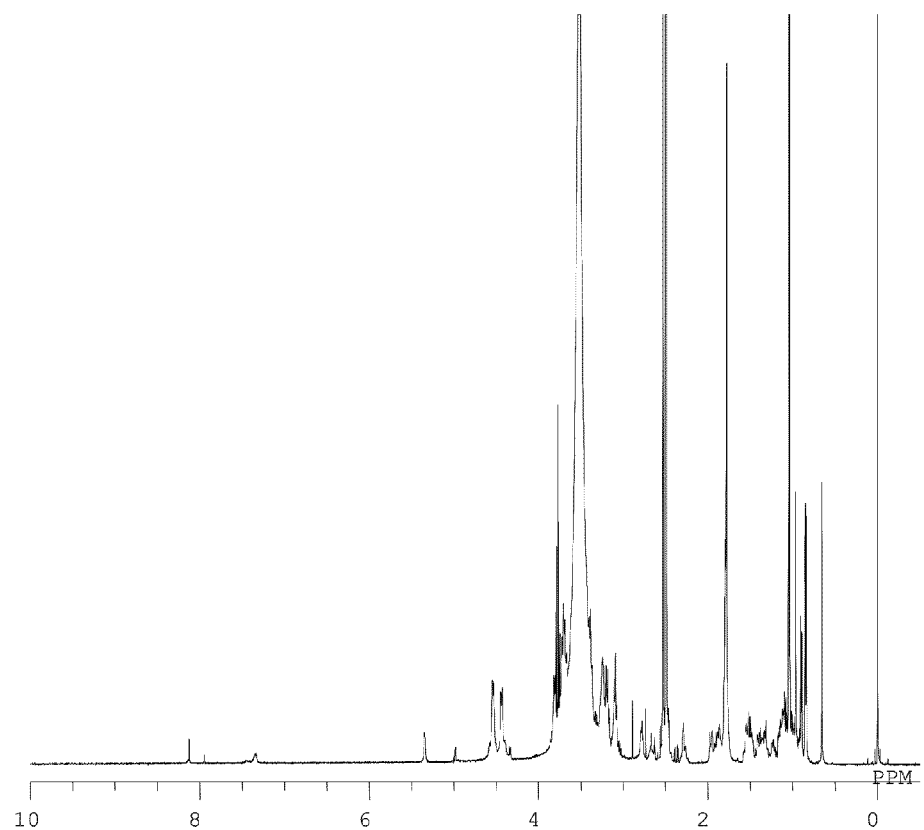
FIG. 18 is one example of the $^1$H-NMR spectrum of a 2-aminoethyl cholesteryl disulfide-introduced HA derivative (HA-SS-Chol) prepared in Example 10.

An anhydrous DMSO solution (10 mg/mL) of HA-TBA prepared by the same procedure as in Example 2-2 using HA-Na (Shiseido Co., Ltd.) having a molecular weight of 10 kDa as a raw material was prepared. Then, 2-aminoethyl 2-pyridyl disulfide hydrochloride (Py-SS-AM, Toronto) was added to each solution at the ratio relative to HA-TBA units indicated in Table 9 below. Thereafter, 4-(4,6-dimethoxy-1,3,5-triazin-2-yl)-4-methylmorpholinium chloride (DMT-MM) was added at the ratio relative to HA-TBA units indicated in Table 9 below and stirred overnight at room temperature. Then, thiocholesterol (Chol-SH, Sigma Aldrich) was added at the ratio indicated in Table 9 below and stirred overnight at room temperature. Sodium nitrate was added to the reaction solution to 0.3 M, and isopropyl alcohol (IPA) was added. The resulting precipitate was recovered, washed with IPA, and then dried under reduced pressure to give an intended product (HA-SS-Chol) as a white solid. The $^1$H-NMR spectrum as measured under the same conditions as those in Example 2-3-1 is shown in FIG. 18. The introduction ratio of cholesteryl groups relative to HA units calculated according to the formula indicated in Example 2-3-1 is shown in Table 9.

TABLE 9

Amount of reagent used in synthesis of HA-SS-Chol and results of synthesis

| Abbreviation | Added molar ratio of Py-SS-AM and DMT-MM (HA-Chol unit/DMT-MM/Py-SS-AM) Added molar ratio of Chol-SH (HA-TBA unit/Chol-SH) | Introduction ratio of Chol (unit %) |
|---|---|---|
| HA-SS-Chol-18% | 100/20/22<br>100/26 | 18 |

Example 11

Figure 19:
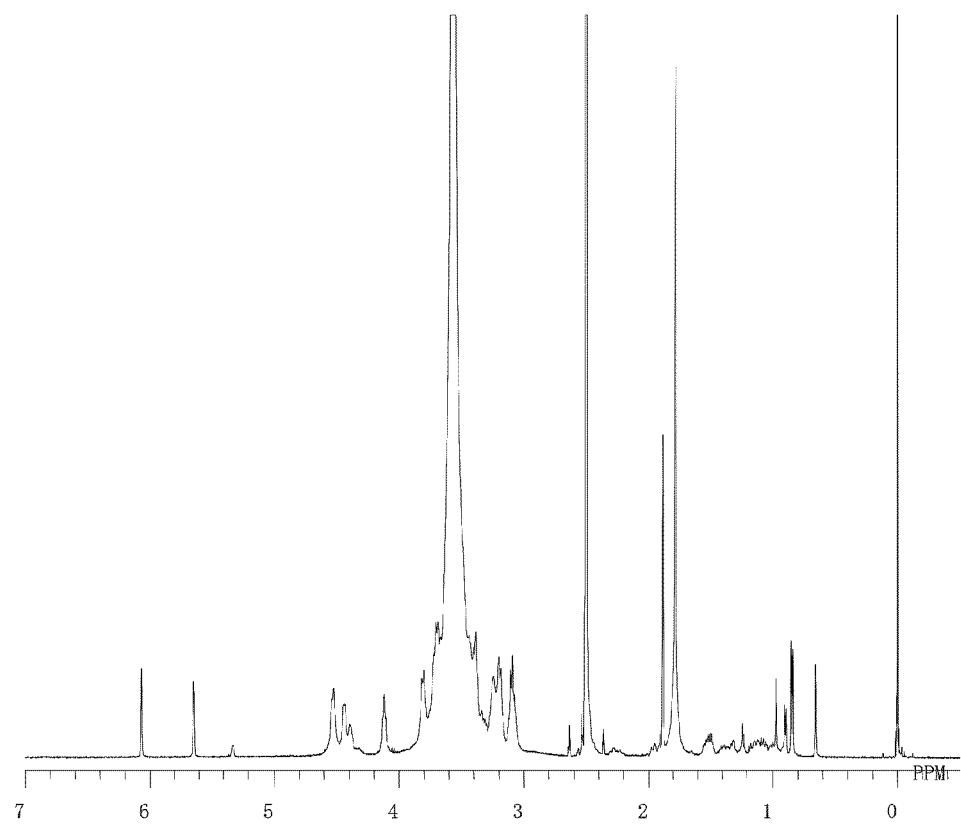
FIG. 19 is one example of the $^1$H-NMR spectrum of the HA derivative prepared in Example 11 in which cholesteryl 2-aminoethylcarbamate and aminoethylmethacrylate are introduced (HA-C$_2$-Chol/AEMA).

Preparation of HA Derivative Modified with Cholesteryl 2-Aminoethylcarbamate and Aminoethyl Methacrylate HA-TBA prepared in Example 2-2 using HA-Na (50 kDa) as a starting material was dissolved at 10 mg/mL in anhydrous DMSO. Then, the Chol-$C_2$ hydrochloride prepared in Example 1-2 was added to each solution at the ratio relative to HA-TBA units indicated in Table 10 below. Thereafter, DMT-MM was added at the ratio relative to HA-TBA units indicated in Table 10 below and stirred at room temperature for 4 hours. Then, aminoethylmethacrylate (AEMA, Polysciences, Inc.) hydrochloride and DMT-MM were added at the ratio indicated in Table 10 below and stirred overnight at room temperature. Treatments thereafter are the same as those shown in Example 2-3-1, whereby HA-$C_2$-Chol/AEMA was obtained as a white solid. The $^1$H-NMR spectrum as measured under the same conditions as those in Example 2-3-1 is shown in FIG. 19. The introduction ratio of cholesteryl groups relative to HA units calculated according to the formula specified in Example 2-3-1 is shown in Table 10. Further, the introduction ratio of methacryl groups relative to HA units calculated according to the formula below from a mean value of methacryloyl group-derived signals at 5.6 ppm and 6.0 ppm is shown in Table 10.

$$\text{Introduction ratio \%} = \frac{\text{Integrated value for methylene group derived from methacryloyl group (6.0, 5.6 ppm)}/2}{\text{Integrated value for acetyl group derived from } HA(1.6 \text{ to } 2.0 \text{ ppm, modified value})/3} \times 100 \quad \text{[Formula 9]}$$

TABLE 10

Amount of reagent used in synthesis of HA-$C_2$-Chol/AEMA and results of synthesis

| Abbreviation | Added molar ratio of Chol-$C_2$ hydrochloride and DMT-MM (HA-TBA unit/DMT-MM/Chol-$C_2$ hydrochloride)<br>Added molar ratio of AEMA hydrochloride and DMT-MM (HA-TBA unit/DMT-MM/AEMA hydrochloride) | Introduction ratio of Chol<br>Introduction ratio of AEMA (unit %) |
|---|---|---|
| HA-$C_2$-Chol-8%/AEMA-27% | 100/8/8.8<br>100/33/60 | 8<br>27 |
| HA-$C_2$-Chol-23%/AEMA-29% | 100/24/26.4<br>100/33/60 | 23<br>29 |

Example 12

Preparation of HA Derivative Modified with 5-Aminomethylfluorescein and Cholesteryl 6-Aminoheptylcarbamate A low-molecular-weight compound was introduced into the HA derivative of the present invention by the procedure described below to obtain a fluorescence-labeled HA derivative. HA-TBA prepared in Example 2-2 using HA-Na (50 kDa) as a starting material was dissolved at 10 mg/mL in anhydrous DMSO. Then, the Chol-$C_6$ hydrochloride prepared in Example 1-1 was added to each solution at the ratio relative to HA-TBA units indicated in Table 11 below. Thereafter, DMT-MM was added at the ratio relative to HA-TBA units indicated in Table 11 below and stirred at room temperature for 4 hours. Then, 5-aminomethylfluorescein (FL, Invitrogen) hydrochloride and DMT-MM were added at the ratio indicated in Table 11 below and stirred overnight at room temperature. Treatments thereafter are the same as those shown in Example 2-3-1, whereby an intended product (HA-$C_6$-Chol/FL) was obtained as a yellow solid. The introduction ratio of cholesteryl groups relative to HA units calculated according to the formula specified in Example 2-3-1 from the $^1$H-NMR spectrum as measured under the same conditions as those in Example 2-3-1 is shown in Table 11. Further, the introduction ratio of fluorescein was calculated from the molar absorption coefficient of 80000 $M^{-1}$ $cm^{-1}$ at 494 nm. Note that labeling with FL was accomplished by formation of an amide bond(s) by an amino group(s) of FL and a carboxy group(s) of HA-TBA.

TABLE 11

Amount of reagent used in synthesis of HA-C6-Chol/FL and results of synthesis

| Abbreviation | Added molar ratio of Chol-$C_6$ hydrochloride and DMT-MM (HA-TBA unit/DMT-MM/Chol-$C_6$ hydrochloride) Added molar ratio of FL hydrochloride and DMT-MM (HA-TBA unit/DMT-MM/FL hydrochloride) | Introduction ratio of Chol Introduction ratio of FL (unit %) |
|---|---|---|
| HA-$C_6$-Chol-20%/FL | 100/24/26.4 | 20 |
|  | 100/4/4.4 | 1 |
| HA-$C_6$-Chol-22%/FL | 100/28/30.8 | 22 |
|  | 100/4/4.4 | 1 |
| HA-$C_6$-Chol-27%/FL | 100/32/35.2 | 27 |
|  | 100/4/4.4 | 1 |
| HA-$C_6$-Chol-34%/FL | 100/40/44 | 34 |
|  | 100/4/4.4 | 1 |

Example 13

Figure 20:
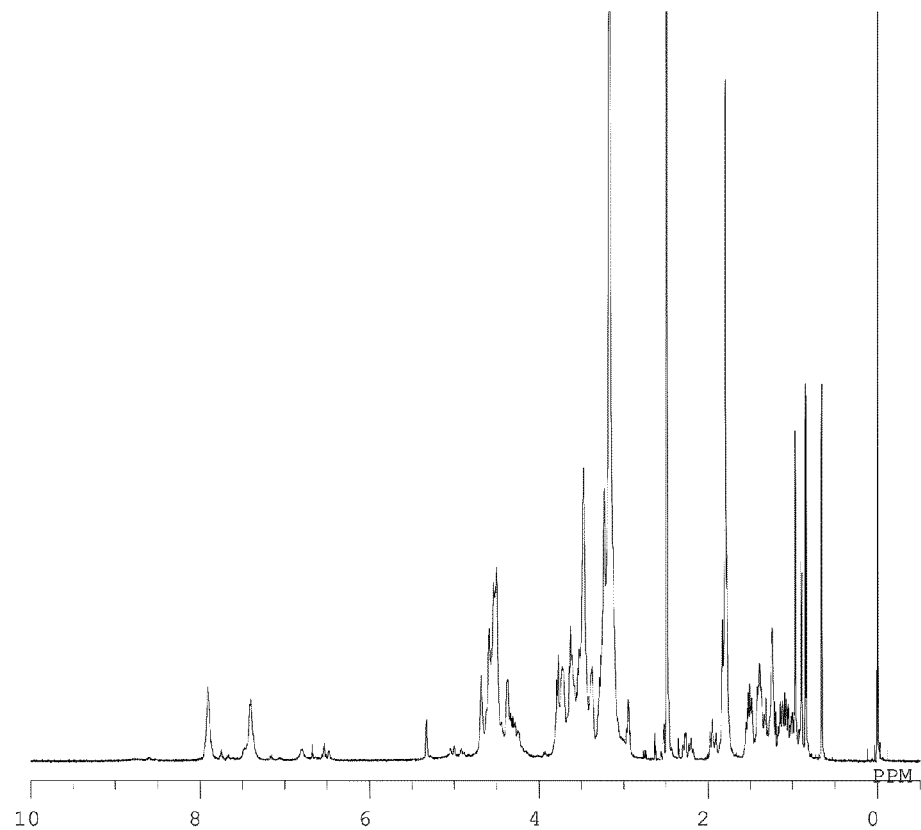
FIG. 20 is one example of the $^1$H-NMR spectrum of the HA derivative prepared in Example 13 in which 5-aminomethylfluorescein, cholesteryl 6-aminoheptylcarbamate, and ethanolamine are introduced (HA-C$_6$-Chol/C$_2$—OH/FL).

Preparation of HA Derivative Modified with 5-Aminomethylfluorescein, Cholesteryl 6-Aminoheptylcarbamate and Ethanolamine or Propanolamine An anhydrous DMSO solution (10 mg/mL) of HA-TBA prepared by the same procedure as in Example 2-2 using HA-Na having a molecular weight of 10 kDa as a raw material was prepared. Then, the Chol-$C_6$ hydrochloride prepared in Example 1-1 was added to each solution at the ratio relative to HA-TBA units indicated in Table 12 below. Thereafter, DMT-MM was added at the ratio relative to HA-TBA units indicated in Table 12 below and stirred at room temperature for 2 hours. Then, 5-aminomethylfluorescein (FL) hydrochloride and DMT-MM were added at the ratio indicated in Table 12 below and stirred overnight at room temperature. Thereafter, ethanolamine (HO—$C_2$) hydrochloride or propanolamine (HO—$C_3$) hydrochloride and DMT-MM were added at the ratio indicated in Table 12 below and stirred at room temperature for 5 hours. Treatments thereafter are the same as those shown in Example 2-3-1, whereby HA-$C_6$-Chol/$C_2$—OH/FL or HA-$C_6$-Chol/$C_3$—OH/FL was obtained as a yellow solid. The $^1$H-NMR spectrum (JNM-ECA500 JEOL Ltd.) as measured using DMSO-$d_6$ as a measurement solvent is shown in FIG. 20 (HA-$C_6$-Chol/$C_2$—OH/FL). The total introduction ratio of Chol-$C_6$, HO—$C_2$ or HO—$C_3$, and FL was calculated from the introduction ratio of cholesteryl groups relative to HA units calculated according to the formula specified in Example 2-3-1, NHCO derived from an amide group(s) of glucosamine, Chol-$C_6$, HO—$C_2$ or HO—$C_3$, and (NH) derived from an amide group(s) of FL. The results are shown in Table 12.

Total introduction ratio % =

$$\frac{\text{Integrated value for amide group-derived (NH) formed by modification (7.9 ppm)}}{\text{Integrated value for (NH) derived from amide group of glucosamine (7.9 ppm)}} \times 100$$

[Formula 10]

TABLE 12

Amount of reagent used in synthesis of HA-$C_6$-Chol/$C_2$-OH/FL and HA-$C_6$-Chol/$C_3$-OH/FL and results of synthesis

| Abbreviation | Added molar ratio of Chol-$C_6$ hydrochloride and DMT-MM (HA-TBA unit/DMT-MM/Chol-$C_6$ hydrochloride) Added molar ratio of FL hydrochloride and DMT-MM (HA-TBA unit/DMT-MM/FL hydrochloride) Added molar ratio of alcohol hydrochloride and DMT-MM (HA-TBA unit/DMT-MM/alcohol hydrochloride) | Introduction ratio of Chol Total introduction ratio of Chol (unit %) |
|---|---|---|
| HA-$C_6$-Chol-19%/$C_2$-OH/FL-95% | 100/24/26.4<br>100/4/4.4<br>100/150/300 (HO-$C_2$) | 19<br>95 |
| HA-$C_6$-Chol-19%/$C_3$-OH/FL-96% | 100/24/26.4<br>100/4/4.4<br>100/150/300 (HO-$C_3$) | 19<br>96 |

Example 14

Preparation of HA Derivatives by Modification of Hyaluronic Acid TBA Salts of Different Molecular Weights with Various Cholesterylcarbamates Under the same conditions as in Example 2-3-1, HA derivatives were prepared by modifying HA-TBAs of various molecular weights with various cholesterylcarbamates. The amount of reagent used in each cholesteryl group-introduced HA derivative and results of synthesis are shown in Table 13. All hyaluronic acids used as raw material were products of Shiseido Co., Ltd.

TABLE 13

Amount of reagent used in synthesis of HA-Chol and results of synthesis

| Abbreviation | Molecular weight of HA | Substituent | Added molar ratio (HA-TBA/DMT-MM/substituent) | Introduction ratio of Chol (unit %) |
|---|---|---|---|---|
| 10k HA-$C_2$-Chol-4% | 10k | Chol-$C_2$ hydrochloride | 100/4/4.4 | 4% |
| 10k HA-$C_2$-Chol-8% | 10k | Chol-$C_2$ hydrochloride | 100/8/8.8 | 8% |
| 10k HA-$C_2$-Chol-16% | 10k | Chol-$C_2$ hydrochloride | 100/16/17.6 | 16% |
| 10k HA-$C_2$-Chol-23% | 10k | Chol-$C_2$ hydrochloride | 100/24/26.4 | 23% |
| 10k HA-$C_2$-Chol-31% | 10k | Chol-$C_2$ hydrochloride | 100/32/35.2 | 31% |
| 10k HA-$C_2$-Chol-40% | 10k | Chol-$C_2$ hydrochloride | 100/40/44 | 40% |
| 10k HA-$C_6$-Chol-4% | 10k | Chol-$C_6$ hydrochloride | 100/4/4.4 | 4% |
| 10k HA-$C_6$-Chol-9% | 10k | Chol-$C_6$ hydrochloride | 100/8/8.8 | 9% |
| 10k HA-$C_6$-Chol-15% | 10k | Chol-$C_6$ hydrochloride | 100/16/17.6 | 15% |
| 10k HA-$C_6$-Chol-23% | 10k | Chol-$C_6$ hydrochloride | 100/24/26.4 | 23% |
| 10k HA-$C_6$-Chol-31% | 10k | Chol-$C_6$ hydrochloride | 100/32/35.2 | 31% |
| 10k HA-$C_6$-Chol-40% | 10k | Chol-$C_6$ hydrochloride | 100/40/44 | 40% |
| 10k HA-$C_{12}$-Chol-8% | 10k | Chol-$C_{12}$ hydrochloride | 100/8/8.8 | 8% |
| 10k HA-$C_{12}$-Chol-24% | 10k | Chol-$C_{12}$ hydrochloride | 100/24/26.4 | 24% |
| 10k HA-EO2-Chol-24% | 10k | Chol-EO2 hydrochloride | 100/24/26.4 | 24% |
| 27k HA-$C_2$-Chol-24% | 27k | Chol-$C_2$ hydrochloride | 100/24/26.4 | 24% |
| 27k HA-$C_2$-Chol-31% | 27k | Chol-$C_2$ hydrochloride | 100/32/35.2 | 31% |
| 27k HA-$C_6$-Chol-16% | 27k | Chol-$C_6$ hydrochloride | 100/16/17.6 | 16% |
| 27k HA-$C_6$-Chol-21% | 27k | Chol-$C_6$ hydrochloride | 100/24/26.4 | 21% |
| 27k HA-$C_6$-Chol-29% | 27k | Chol-$C_6$ hydrochloride | 100/32/35.2 | 29% |
| 27k HA-$C_{12}$-Chol-8% | 27k | Chol-$C_{12}$ hydrochloride | 100/16/17.6 | 16% |
| 27k HA-$C_{12}$-Chol-24% | 27k | Chol-$C_{12}$ hydrochloride | 100/24/26.4 | 24% |
| 27k HA-$C_{12}$-Chol-32% | 27k | Chol-$C_{12}$ hydrochloride | 100/32/35.2 | 32% |
| 27k HA-EO2-Chol-23% | 27k | Chol-EO2 hydrochloride | 100/24/26.4 | 23% |

TABLE 13-continued

Amount of reagent used in synthesis of HA-Chol and results of synthesis

| Abbreviation | Molecular weight of HA | Substituent | Added molar ratio (HA-TBA/DMT-MM/ substituent) | Introduction ratio of Chol (unit %) |
|---|---|---|---|---|
| 27k HA-EO2-Chol-29% | 27k | Chol-EO2 hydrochloride | 100/32/35.2 | 29% |
| 99k HA-$C_2$-Chol-22% | 99k | Chol-$C_2$ hydrochloride | 100/24/26.4 | 22% |
| 99k HA-$C_2$-Chol-29% | 99k | Chol-$C_2$ hydrochloride | 100/32/35.2 | 29% |
| 99k HA-$C_6$-Chol-14% | 99k | Chol-$C_6$ hydrochloride | 100/16/17.6 | 14% |
| 99k HA-$C_6$-Chol-23% | 99k | Chol-$C_6$ hydrochloride | 100/24/26.4 | 23% |
| 99k HA-$C_6$-Chol-29% | 99k | Chol-$C_6$ hydrochloride | 100/32/35.2 | 29% |
| 99k HA-$C_6$-Chol-33% | 99k | Chol-$C_6$ hydrochloride | 100/40/44 | 33% |
| 99k HA-$C_6$-Chol-37% | 99k | Chol-$C_6$ hydrochloride | 100/50/55 | 37% |
| 99k HA-$C_{12}$-Chol-7% | 99k | Chol-$C_{12}$ hydrochloride | 100/8/8.8 | 7% |
| 99k HA-$C_{12}$-Chol-22% | 99k | Chol-$C_{12}$ hydrochloride | 100/24/26.4 | 22% |
| 99k HA-$C_{12}$-Chol-27% | 99k | Chol-$C_{12}$ hydrochloride | 100/32/35.2 | 27% |
| 99k HA-EO2-Chol-21% | 99k | Chol-EO2 hydrochloride | 100/24/26.4 | 21% |
| 99k HA-EO2-Chol-26% | 99k | Chol-EO2 hydrochloride | 100/32/35.2 | 26% |
| 230k HA-$C_6$-Chol-12% | 230k | Chol-$C_6$ hydrochloride | 100/16/17.6 | 12% |
| 230k HA-$C_6$-Chol-17% | 230k | Chol-$C_6$ hydrochloride | 100/24/26.4 | 17% |
| 230k HA-$C_6$-Chol-23% | 230k | Chol-$C_6$ hydrochloride | 100/32/35.2 | 23% |
| 230k HA-$C_6$-Chol-27% | 230k | Chol-$C_6$ hydrochloride | 100/40/44 | 27% |
| 230k HA-$C_6$-Chol-33% | 230k | Chol-$C_6$ hydrochloride | 100/50/55 | 33% |
| 230k HA-$C_{12}$-Chol-7% | 230k | Chol-$C_{12}$ hydrochloride | 100/8/8.8 | 7% |
| 50k HA-$C_6$-Chol-7% | 50k | Chol-$C_6$ hydrochloride | 100/8/8.8 | 7% |
| 50k HA-$C_6$-Chol-14% | 50k | Chol-$C_6$ hydrochloride | 100/16/17.6 | 14% |
| 50k HA-$C_6$-Chol-24% | 50k | Chol-$C_6$ hydrochloride | 100/24/26.4 | 24% |
| 50k HA-$C_6$-Chol-31% | 10k | Chol-$C_6$ hydrochloride | 100/32/35.2 | 31% |

Example 15

Preparation of HA Derivatives by Modification of Hyaluronic Acid TBA Salts of Different Molecular Weights with Various Cholesterylcarbamates and 5-Aminomethylfluoresceins Under the same conditions as in Example 12, HA derivatives were prepared by modification of HA-TBAs of different molecular weights with various cholesterylcarbamates and 5-aminomethylfluoresceins (FL). The same amount of FL was used as in Example 12. As raw material used, hyaluronic acid of 5 kDa was a product of R&D Systems, and others were obtained from Shiseido Co., Ltd.

The amount of reagent used in each cholesteryl group-introduced HA derivative and results of synthesis are shown in Table 14.

TABLE 14

Amount of reagent used in synthesis of HA-Chol/FL and results of synthesis

| Abbreviation | Molecular weight of HA | Substituent | Added molar ratio (HA-TBA/DMT-MM/ substituent) | Introduction ratio of Chol (unit %) |
|---|---|---|---|---|
| 5k HA-$C_6$-Chol-19%/FL | 5k | Chol-$C_6$ hydrochloride | 100/20/22 | 19% |
| 5k HA-$C_6$-Chol-23%/FL | 5k | Chol-$C_6$ hydrochloride | 100/24/26.4 | 23% |
| 10k HA-$C_6$-Chol-15%/FL | 10k | Chol-$C_6$ hydrochloride | 100/16/17.6 | 15% |
| 10k HA-$C_6$-Chol-22%/FL | 10k | Chol-$C_6$ hydrochloride | 100/24/26.4 | 22% |
| 10k HA-$C_6$-Chol-29%/FL | 10k | Chol-$C_6$ hydrochloride | 100/32/35.2 | 29% |
| 10k HA-$C_2$-Chol-22%/FL | 10k | Chol-$C_2$ hydrochloride | 100/24/26.4 | 22% |
| 10k HA-$C_{12}$-Chol-22%/FL | 10k | Chol-$C_{12}$ hydrochloride | 100/24/26.4 | 22% |
| 10k HA-EO2-Chol-20%/FL | 10k | Chol-EO2 hydrochloride | 100/24/26.4 | 20% |
| 18k HA-$C_6$-Chol-15%/FL | 18k | Chol-$C_6$ hydrochloride | 100/20/22 | 15% |
| 18k HA-$C_6$-Chol-20%/FL | 18k | Chol-$C_6$ hydrochloride | 100/24/26.4 | 20% |
| 18k HA-$C_6$-Chol-24%/FL | 18k | Chol-$C_6$ hydrochloride | 100/32/35.2 | 24% |
| 27k HA-$C_6$-Chol-22%/FL | 27k | Chol-$C_6$ hydrochloride | 100/24/26.4 | 22% |
| 27k HA-$C_6$-Chol-30%/FL | 27k | Chol-$C_6$ hydrochloride | 100/32/35.2 | 30% |
| 99k HA-$C_6$-Chol-19%/FL | 99k | Chol-$C_6$ hydrochloride | 100/24/26.4 | 19% |
| 99k HA-$C_6$-Chol-25%/FL | 99k | Chol-$C_6$ hydrochloride | 100/32/35.2 | 25% |
| 99k HA-$C_6$-Chol-30%/FL | 99k | Chol-$C_6$ hydrochloride | 100/40/44 | 30% |
| 230k HA-$C_6$-Chol-20%/FL | 99k | Chol-$C_6$ hydrochloride | 100/24/26.4 | 20% |
| 230k HA-$C_6$-Chol-24%/FL | 99k | Chol-$C_6$ hydrochloride | 100/32/35.2 | 24% |

Example 16

Preparation of HA Derivatives by Modification with Hilyte Fluor™ 750 Amine and 6-Aminohexylcarbamate (for In Vivo Imaging)

Except that Hilyte Fluor™ 750 amine (Hilyte) TFA salt was used in place of 5-aminomethylfluorescein (FL) hydrochloride, the procedure of Example 12 was repeated under the same conditions to prepare the above-identified HA derivative (HA-$C_6$-Chol/Hilyte). The added molar ratios are shown in Table 15. After addition of Hilyte Fluor™ 750 amine TFA salt, ethanolamine hydrochloride was reacted as in Example 13 to thereby prepare HA-$C_6$-Chol/$C_2$—OH/Hilyte. The added molar ratios are shown in Table 15. The introduction ratio was calculated by the same method as in Examples 12 and 13. Note that the labeling with Hilyte Fluor™ 750 amine was accomplished by an amide bond(s) formed by an amino group(s) of Hilyte Fluor™ 750 amine with a carboxy group(s) of HA-TBA.

TABLE 15

Amount of reagent used in synthesis of HA-$C_6$-Chol/Hilyte and results of synthesis

| Abbreviation | Added molar ratio of Chol-$C_6$ hydrochloride and DMT-MM (HA-TBA unit/DMT-MM/Chol-$C_6$ hydrochloride) Added molar ratio of Hilyte TFA salt and DMT-MM (HA-TBA unit/DMT-MM/FL hydrochloride) Added molar ratio of HO-$C_2$ hydrochloride and DMT-MM (HA unit/DMT-MM/HO-$C_2$ hydrochloride) | Introduction ratio of Chol Total introduction ratio (unit %) |
|---|---|---|
| 10k HA-$C_6$-Chol-22%/Hilyte | 100/20/22<br>100/6/3<br>—/—/— | 22<br>— |
| 50k HA-$C_6$-Chol-27%/Hilyte | 100/28/30.8<br>100/6/3<br>—/—/— | 27<br>— |
| 10k HA-$C_6$-Chol-22%/HO-$C_2$/Hilyte | 100/20/22<br>100/6/3<br>100/150/300 | 22<br>80.5 |

Example 17

DLS Measurement of Cholesteryl Group-Introduced HA Derivative

Figure 21:
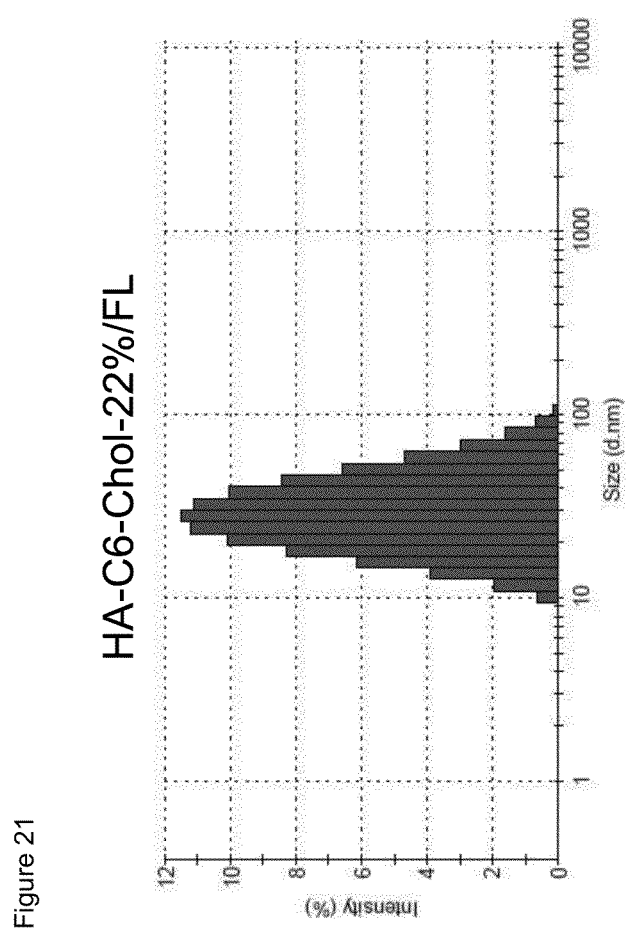
FIG. 21 is one example of a chart showing the results of measurement of the particle size of the HA derivative (50 k HA-C$_6$-Chol-22%/FL) by dynamic light scattering (DLS).

PBS solutions (0.25 mg/mL) of the HA derivatives synthesized in Examples 12 and 15 were prepared, and particle sizes were measured by dynamic light scattering (DLS). As a measurement device, Zetasizer Nano ZS (Malvern) was used. The z-average particle sizes are shown in Table 16. The size distribution of 50 k HA-$C_6$-Chol-22%/FL is shown in FIG. 21.

TABLE 16

Particle size of HA derivative

| Abbreviation | Diameter nm |
|---|---|
| 10k HA-$C_6$-Chol-22%/FL | 26.9 |
| 50k HA-$C_6$-Chol-27%/FL | 40.0 |
| 230k HA-$C_6$-Chol-20%/FL | 36.9 |

From the results it was confirmed that the HA derivative formed an extremely small particle of 50 nm or smaller in PBS. The particle of the above size is suitable for use as a drug carrier, because the uptake by the reticuloendothelial system in the living body can be avoided.

Example 18

Preparation of Complex of Cholesteryl Group-Introduced HA Derivative and Protein

Example 18-1

Lysozyme

Figures 1, 22:
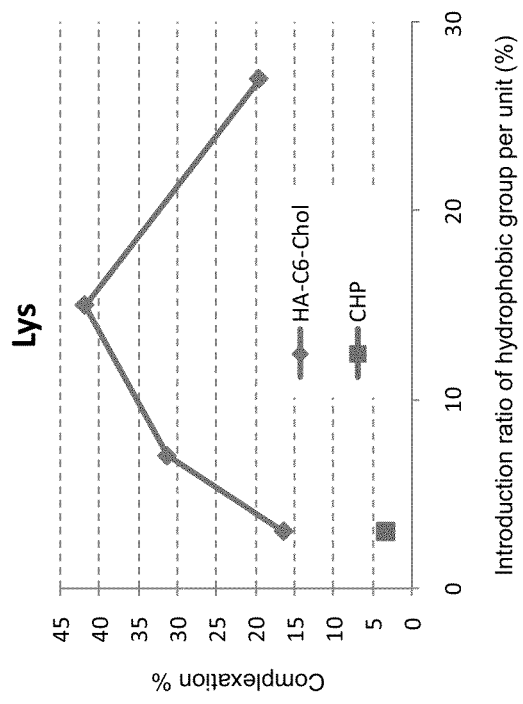
Figures 2, 22:
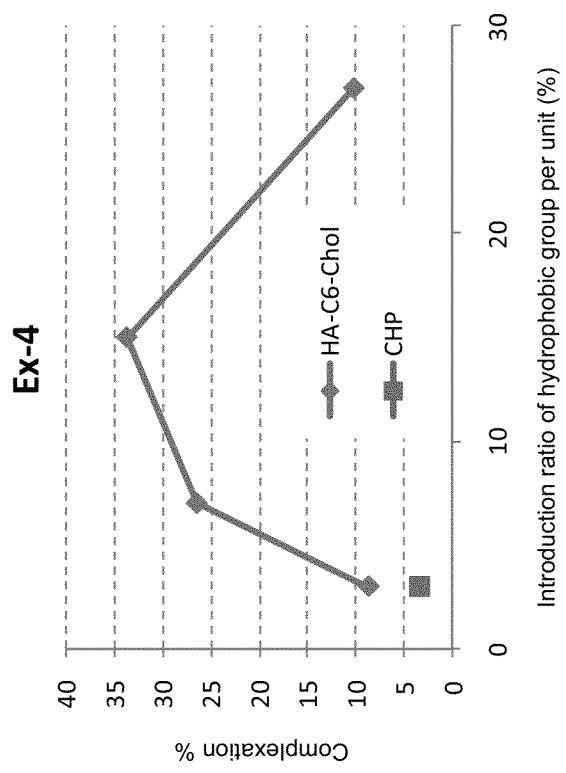
Figures 3, 22:
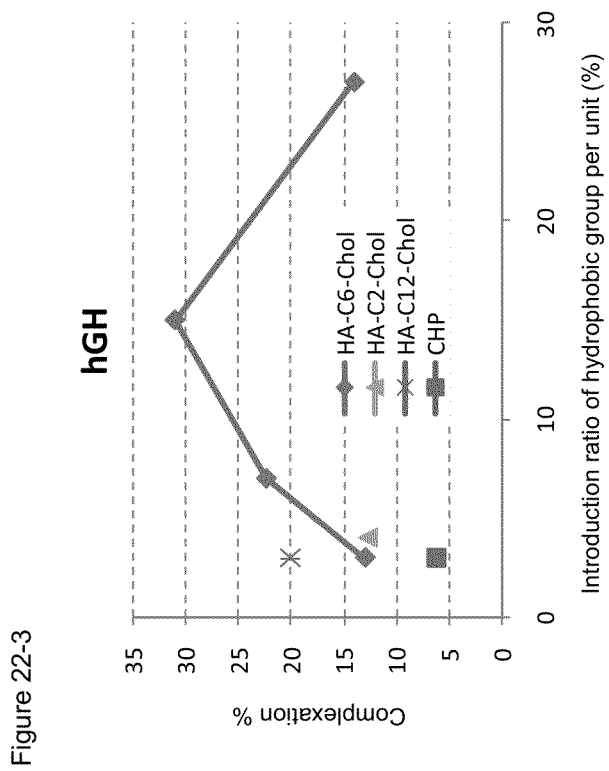
Figures 4, 22:
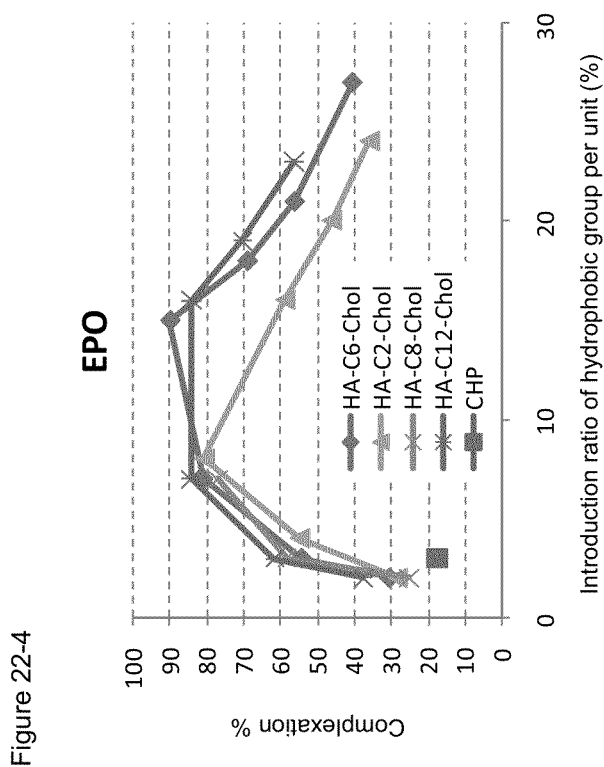

The procedure of Example 5 was repeated to prepare complexes of lysozyme (Lys: Lysozyme from chicken egg white, Sigma) with HA derivatives and CHP shown in Table 17. Concentrated PBS (50 μL) was added to an aqueous solution of Lys (4 mg/mL, 25 μL) to give a final concentration of 1×PBS, and then the HA derivative or CHP (4 mg/mL, 25 μL) was added. After incubation at 37° C. for 24 hours, the mixture was subjected to centrifugal separation at 6000 G, and the supernatant in which all free Lys and dispersible complex were present was subjected to size exclusion chromatography. From the results of chromatography, the amount of free Lys that was not incorporated into the complex and thus remained in the aqueous solution was determined, and the amount of Lys contained in the complex was calculated. Further, the amount of Lys contained in the complex per unit weight of the HA derivative and CHP (complexation %; (weight of Lys in the complex/weight of HA derivative)×100) was calculated. The results are shown in Table 17 below, and the graph is shown in FIG. 22-1.

SEC Measurement Conditions
Column: G3000PWXL (Tosoh Corporation, Japan)
Eluent: 2×PBS (pH 7.4)
Flow rate: 1 mL/min
Amount of injection: 50 μL
Detection: UV (280 nm).

TABLE 17

Amount of complexed lysozyme of modified HA

| Abbreviation | Introduction ratio unit % | Complexation % |
|---|---|---|
| HA-$C_6$-Chol-3% | 3 | 16 |
| HA-$C_6$-Chol-7% | 7 | 31 |
| HA-$C_6$-Chol-15% | 15 | 42 |
| HA-$C_6$-Chol-27% | 27 | 20 |
| CHP | 3 | 3 |

The value of complexation % of the HA derivative of the present invention was about 5- to 12-fold higher than that of CHP; it was confirmed that the HA derivative of the present invention efficiently formed a complex with Lys.

Example 18-2

Exendin-4

The procedure of Example 5 was repeated to form complexes of exendin-4 (Ex-4, American Peptide Co. Inc.) with HA derivatives and CHP shown in Table 18. Concentrated PBS (44.8 µL) was added to an aqueous solution of Ex-4 (3.31 mg/mL, 30.2 µL) to give a final concentration of 1×PBS, and then the HA derivative or CHP (4 mg/mL, 25 µL) was added. After incubation at 37° C. for 24 hours, the mixture was subjected to centrifugal separation at 6000 G, and the supernatant in which all free Ex-4 and dispersible complex was present were subjected to size exclusion chromatography. From the results of chromatography, the amount of free Ex-4 that was not incorporated into the complex and thus remained in the aqueous solution was determined, and the amount of Ex-4 contained in the complex was calculated. Further, the amount of Ex-4 contained in the complex per unit weight of HA derivative and CHP (complexation %; (weight of Ex-4 in the complex/weight of HA derivative)×100) was calculated. The results are shown in Table 18 below, and the graph is shown in FIG. 22-2.

SEC Measurement Conditions
Column: QC-PAK-GFC200 (Tosoh Corporation, Japan)
Eluent: PBS (pH 7.4)
Flow rate: 1.2 mL/min
Amount of injection: 50 µL
Detection: UV (280 nm).

TABLE 18

Amount of complexed exendin-4 of modified HA

| Abbreviation | Introduction ratio unit % | Complexation % |
|---|---|---|
| HA-$C_6$-Chol-3% | 3 | 9 |
| HA-$C_6$-Chol-7% | 7 | 26 |
| HA-$C_6$-Chol-15% | 15 | 34 |
| HA-$C_6$-Chol-27% | 27 | 10 |
| CHP | 3 | 3 |

The value of complexation % of the HA derivative of the present invention was about 3- to 11-fold higher than that of CHP; it was confirmed that the HA derivative of the present invention efficiently formed a complex with exendin-4.

Example 18-3

Human Growth Hormone

The procedure of Example 5 was repeated to prepare complexes of human growth hormone (hGH: Genotropin® for injection) with HA derivatives and CHP shown in Table 19. Genotropin® was dialyzed to replace the solvent with a phosphate buffer solution (10 mM, pH 7.4) and used as hGH. Concentrated PBS (60.4 µL) was added to an aqueous solution of hGH (3.5 mg/mL, 14.3 µL) to give a final concentration of 1×PBS, and then the HA derivative or CHP (4 mg/mL, 25 µL) was added. After incubation at 37° C. for 24 hours, the mixture was subjected to centrifugal separation at 6000 G, and the supernatant in which all free hGH and dispersible complex were present was subjected to size exclusion chromatography. From the results of chromatography, the amount of free hGH that was not incorporated into the complex and thus remained in the aqueous solution was calculated, and the amount of hGH contained in the complex was calculated. Further, the amount of hGH contained in the complex per unit weight of the HA derivative (complexation %; (weight of Ex-4 in the complex/weight of HA derivative)×100) was calculated. The results are shown in Table 19 below, and the graph is shown in FIG. 22-3.

SEC Measurement Conditions
Column: QC-PAK-GFC300 (Tosoh Corporation, Japan)
Eluent: PBS (pH 7.4)
Flow rate: 1.2 mL/min
Amount of injection: 30 µL
Detection: UV (280 nm).

TABLE 19

Amount of complexed hGH of modified HA

| Abbreviation | Introduction ratio unit % | Complexation % |
|---|---|---|
| HA-$C_6$-Chol-3% | 3 | 13 |
| HA-$C_6$-Chol-7% | 7 | 22 |
| HA-$C_6$-Chol-15% | 15 | 31 |
| HA-$C_6$-Chol-27% | 27 | 14 |
| HA-$C_2$-Chol-4% | 4 | 13 |
| HA-$C_{12}$-Chol-3% | 3 | 20 |
| CHP | 3 | 6 |

The value of complexation % of the HA derivative of the present invention was about 2- to 5-fold higher than that of CHP; it was confirmed that the HA derivative of the present invention efficiently formed a complex with hGH.

Example 18-4

Amount of Complexed EPO of Modified HA (No. 2)

The procedure of Example 5 was repeated to prepare complexes of HA derivatives shown in Table 20 and EPO, and each complexation % was calculated. The graph is shown in FIG. 22-4.

TABLE 20

Amount of complexed erythropoietin of modified HA

| Abbreviation | Introduction ratio unit % | Complexation % |
|---|---|---|
| HA-$C_6$-Chol-6% | 6 | 70 |
| HA-$C_6$-Chol-7% | 7 | 73 |
| HA-$C_6$-Chol-15% | 15 | 87 |
| HA-$C_6$-Chol-18% | 18 | 69 |
| HA-$C_6$-Chol-21% | 21 | 56 |
| HA-$C_6$-Chol-27% | 27 | 43 |
| HA-$C_2$-Chol-8% | 8 | 74 |
| HA-$C_2$-Chol-16% | 16 | 59 |
| HA-$C_2$-Chol-20% | 20 | 46 |
| HA-$C_2$-Chol-24% | 24 | 36 |
| HA-$C_{12}$-Chol-7% | 7 | 78 |
| HA-$C_{12}$-Chol-16% | 16 | 84 |
| HA-$C_{12}$-Chol-19% | 19 | 70 |
| HA-$C_{12}$-Chol-23% | 23 | 56 |
| HA-$C_8$-Chol-7% | 7 | 80 |

The value of complexation % of the HA derivative of the present invention was about 5-fold, at the most, higher than that of CHP; it was confirmed that the HA derivative of the present invention efficiently formed a complex with EPO.

Example 19

EPO In Vitro Release

Example 19-1

Preparation of Alexa-EPO

To an aqueous solution of EPO treated to replace a buffer solution with a carbonic acid buffer solution (0.3M, pH 9.0), 1 mg of Alexa Fluor® 488 5-TFP (Invitrogen) was added by dropping, and stirred at room temperature for 1 hour. After purification by gel filtration with a PD-10 column, purification by dialysis (7000 MWCO dialysis membrane) was carried out with a phosphate buffer solution (10 mM, pH 7.4), whereby an EPO (Alexa-EPO) solution fluorescence-labeled with Alexa Fluor® 488 was obtained. Note that the labeling with Alexa Fluor® 488 was accomplished by an amide bond(s) formed by a carboxy group(s) of Alexa Fluor® 488 and an amino group(s) of EPO.

Example 19-2

Alexa-EPO Sustained-Release Effect of HA Derivative

Figures 1, 23:
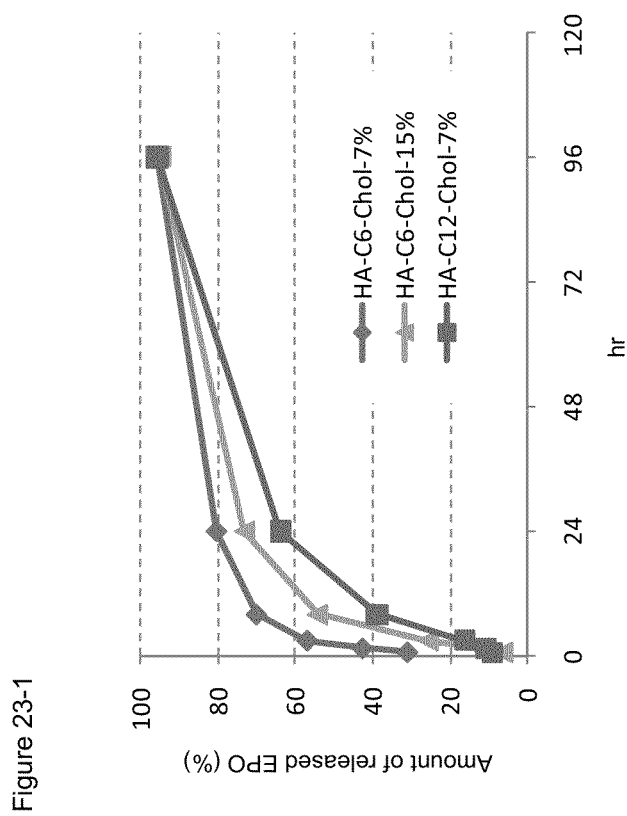
Figures 2, 23:
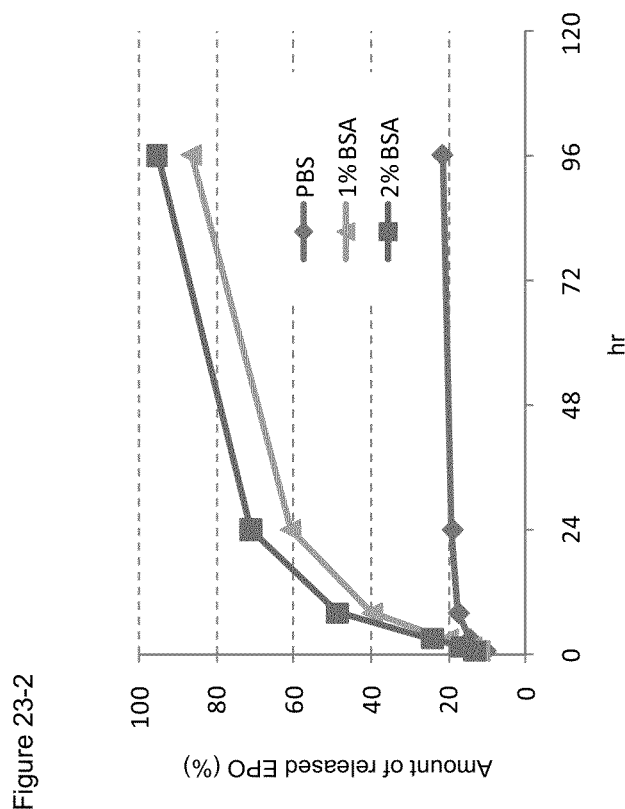

Concentrated PBS (90 µL) was added to the Alexa-EPO solution (3.34 mg/mL, 10 µL) obtained in Example 19-1 to give a final concentration of 1×PBS, and then the HA derivative (6 mg/mL, 100 µL) was added. HA-$C_6$-Chol-7%, HA-$C_6$-Chol-15%, and HA-$C_{12}$-Chol-7% were used as the HA derivative (the molecular weight of each HA-Na used as a raw material was 50 kDa). The mixture was incubated at 37° C. for 24 hours and then lyophilized. A bovine serum albumin (BSA: Sigma)/PBS solution (200 µL) was added at 20 mg/mL with respect to a total amount of the lyophilization product, and the mixture was centrifuged over time. Thereafter, the supernatant (100 µL) was collected, and fresh BSA/PBS solution (100 µL) was added. The supernatant was diluted 2-fold with HP-β-CD aqueous solution (100 mM), incubated at 37° C. for 1 hour, and then subjected to SEC. The concentration of Alexa-EPO was calculated, and the amount of Alexa-EPO released was calculated. The results are shown in FIG. 23-1.
  SEC Analysis Conditions
  Column: G3000SWXL (Tosoh Corporation, Japan)
  Eluent: 10 mM HP-β-CD/PBS (pH 7.4)
  Flow rate: 1 mL/min
  Amount of injection: 50 µL
  Detection: Fluorescence detection 494/525

It was demonstrated that every HA derivative had sustained-release effect. Furthermore, it became clear that the sustained-release effect was greater in the case of an introduction ratio of cholesteryl groups of 15% than 7% and in the case of $C_{12}$ spacer than $C_6$ spacer.

Example 19-3

Effect of BSA Concentration on Release Solution

Concentrated PBS (133.3 µL) was added to the Alexa-EPO solution (3.34 mg/mL, 10 µL) obtained in Example 19-1 to give a final concentration of 1×PBS, and then HA-$C_{12}$-Chol-7% (6 mg/mL, 16.7 µL) was added (the molecular weight of HA-Na used as a raw material was 50 kDa). The mixture was incubated at 37° C. for 24 hours and then lyophilized A bovine serum albumin (BSA: Sigma)/PBS solution (200 µL) was added at 20 mg/mL, 10 mg/mL, or 0 mg/mL with respect to a total amount of the lyophilization product, and the mixture was centrifuged over time. Thereafter, 100 µL of supernatant was collected, and fresh BSA/PBS solution (100 µL) was added. The supernatant was diluted 2-fold with an aqueous solution of HP-β-CD (100 mM), incubated at 37° C. for 1 hour, and then subjected to SEC. The Alexa-EPO concentration was calculated, and the amount of released Alexa-EPO was calculated. The results are shown in FIG. 23-2. SEC conditions were the same as those in Example 19-2.

From the results it became clear that the release rate of EPO encapsulated in (complexed with) the HA derivative of the present invention depended on the BSA concentration.

Comparative Example 1

Pharmacokinetic Study of hGH Rats

Figure 24:
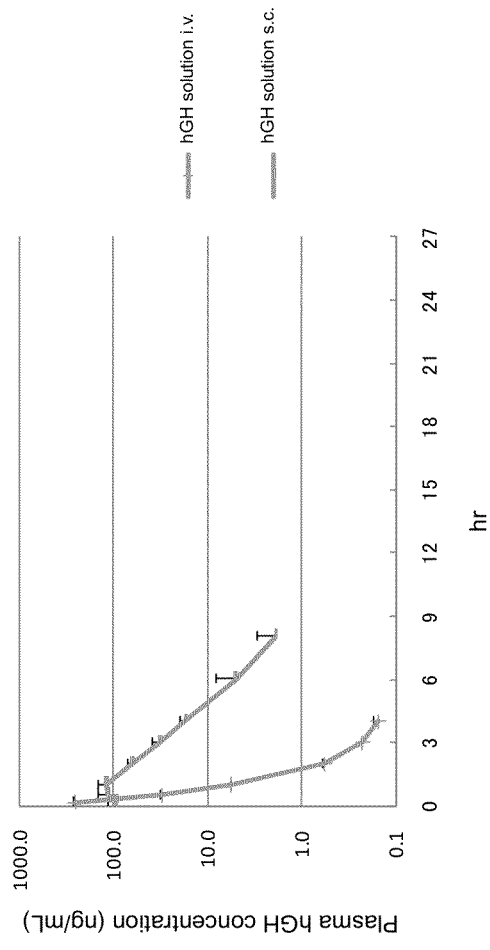
FIG. 24 is one example of a graph showing the results of the time course of plasma concentration of human growth hormone subcutaneously administered to rats and the time course of plasma concentration of human growth hormone administered to tail veins of the rats.

The hGH solution was subcutaneously administered to normal rats (SD, 6 weeks of age, male) and also administered to tail veins of normal rats with a 25G-needle at the dose indicated in Table 21. After administration, blood was collected over time from the jugular vein using a heparin-treated syringe, and aprotinin was added as a protease inhibitor. The resulting blood was treated to separate plasma, and the hGH concentration was measured with an ELISA kit (Roche Applied Science). The time course of plasma hGH concentration at the time of subcutaneous administration and at the time of administration to the tail veins is shown in FIG. 24. Moreover, pharmacokinetic parameters (extrapolated area under the plasma concentration-time curve (AUC∞) and mean residence time (MRT)) were analyzed by WinNonlin Ver.5.0.1 (Pharsight). The values obtained are shown in Table 21.

TABLE 21

Dose of hGH solution and pharmacokinetic parameters

| Sample | hGH dose (mg/kg) | AUC∞ (ng · hr/mL) | MRT (time) |
|---|---|---|---|
| hGH solution i.v. | 0.1 | 123 | 0.2 |
| hGH solution s.c. | 0.5 | 280 | 20 |

Example 20 hGH In Vivo Release

Example 20-1

Preparation of Lyophilized Precipitate Product of Complex of hGH and HA Derivative To the HA derivatives (6 mg/mL, 3.375 mL) obtained in Example 2-3-1 and Example 14, hGH (4.31 mg/mL, 0.940 mL) was added, and each mixture was incubated at 37° C. for 1 hour. Further, concentrated PBS (0.185 mL) was added to give a final concentration of 1×PBS and incubated at room temperature for 1 hour. Precipitation was confirmed. After centrifugation for 30 minutes, the supernatant (2.25 mL) was removed, and an aqueous solution of sucrose (150 mg/mL, 1.125 mL) was added and dispersed well, followed by lyophilization. The amount of free hGH contained in the supernatant was calculated from SEC, and the complexation % was calculated. Further, a predetermined amount of the lyophilization product was collected, and the recovery ratio was calculated from the amount of hGH contained in the lyophilization product. The results are shown in Table 22.

TABLE 22

Amount of complexed hGH of modified HA

| HA derivative | Introduction ratio | Complexation % | Recovery ratio % |
|---|---|---|---|
| 50k HA-$C_6$-Chol-7% | 7 | 99 | 84 |
| 50k HA-$C_6$-Chol-14% | 14 | 99 | 94 |
| 50k HA-$C_{12}$-Chol-7% | 7 | 97 | 80 |
| 99k HA-$C_{12}$-Chol-7% | 7 | 99 | 81 |

From the above results it became clear that the HA derivative of the present invention efficiently encapsulated (was efficiently complexed with) hGH.

Example 20-2

Preparation of hGH/HA Derivative Complex (Precipitate)

To HA-$C_6$-Chol-14% (6 mg/mL, 0.583 mL; the molecular weight of HA-Na used as a raw material was 50 kDa), hGH (4.84 mg/mL, 0.145 mL) was added and incubated at 37° C. for 1 hour. Further, concentrated PBS (0.147 mL) was added to give a final concentration of 1×PBS and incubated at room temperature for 1 hour. Precipitation was confirmed. The resulting substance was stored at 4° C.

Example 20-3

Preparation of hGH/HA Derivative Complex (Solution)

To HA-$C_6$-Chol-14% (6 mg/mL, 0.583 mL; the molecular weight of HA-Na used as a raw material was 50 kDa), hGH (4.84 mg/mL, 0.145 mL) and an aqueous solution of sucrose (0.147 mL) were added to give a final concentration of 82 mg/mL and incubated at 37° C. for 1 hour. No precipitation was confirmed. The resulting substance was stored at 4° C.

This formulation is to be administered in the form of a solution and to be precipitated by elevation of ion intensity in the subcutis after administration.

Example 20-4

Figure 25:
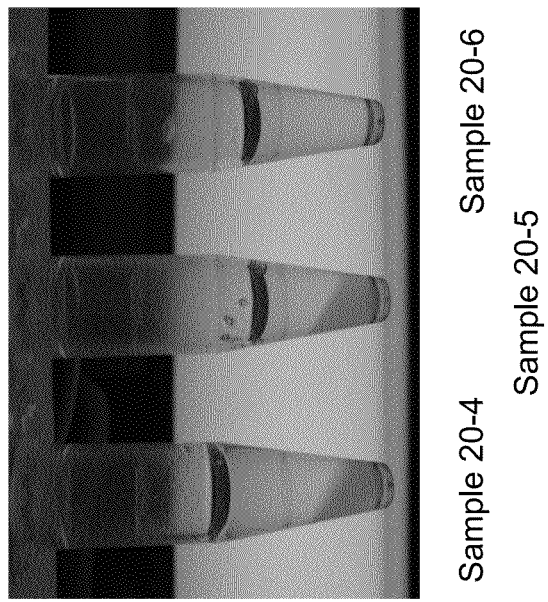
FIG. 25 is a photograph of a formulation sample of a complex of hGH/HA derivative used in Example 20-4.
Figures 1, 26:
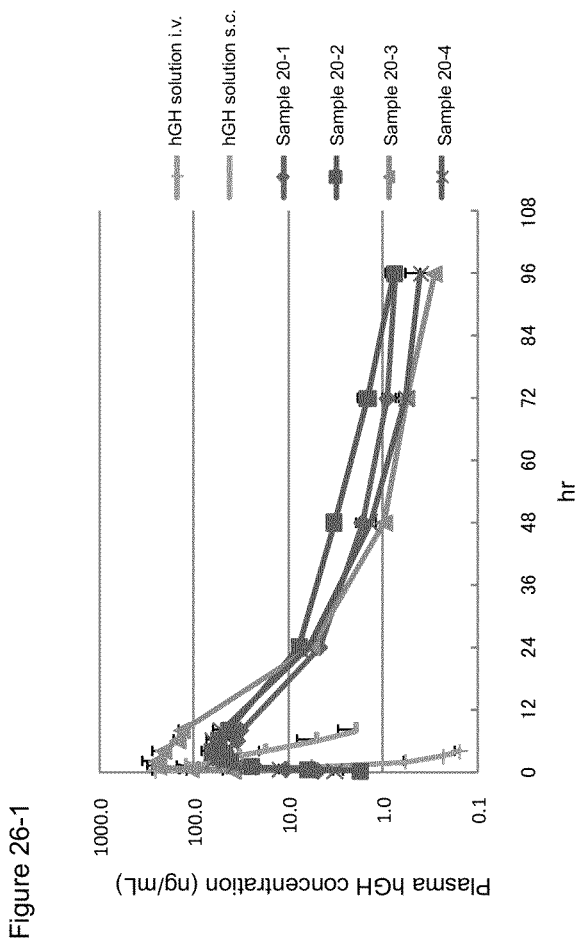
Figures 2, 26:
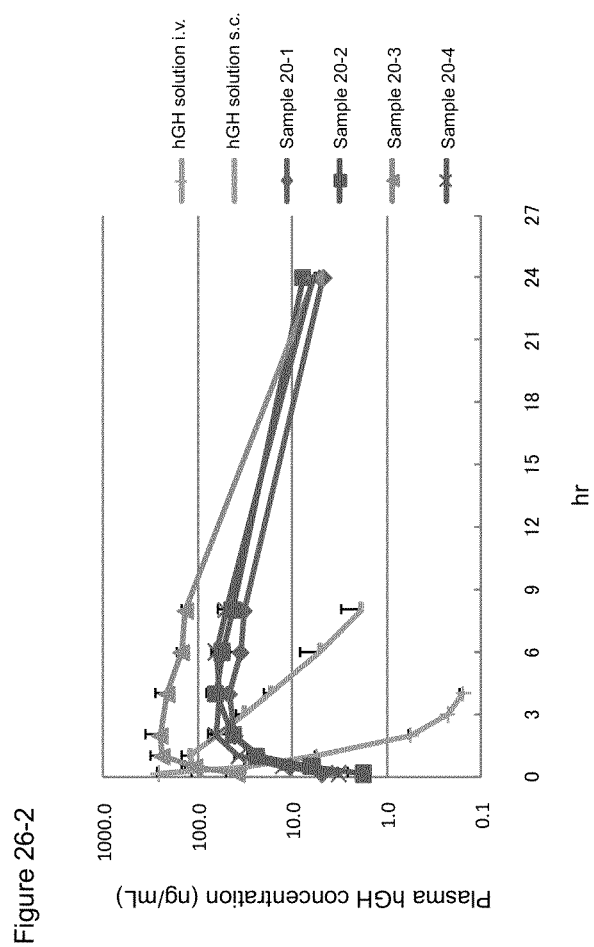
Figures 1, 27:
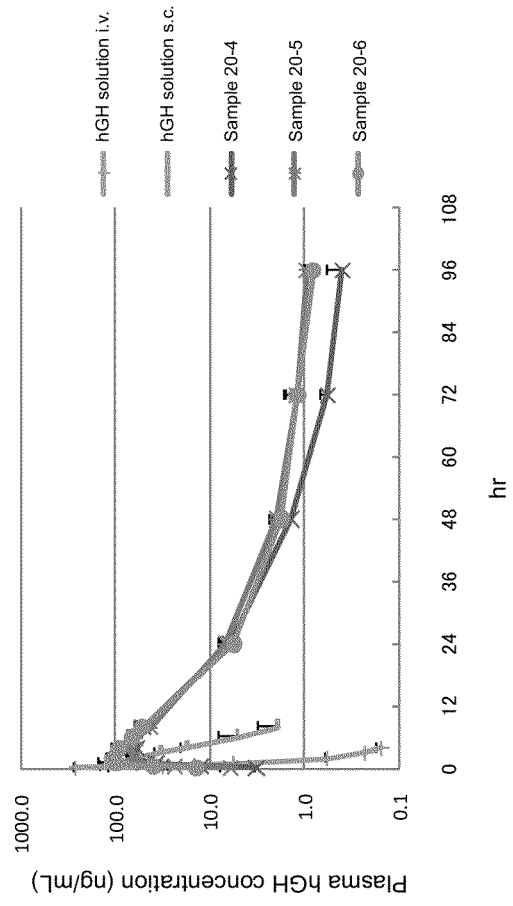
Figures 2, 27:
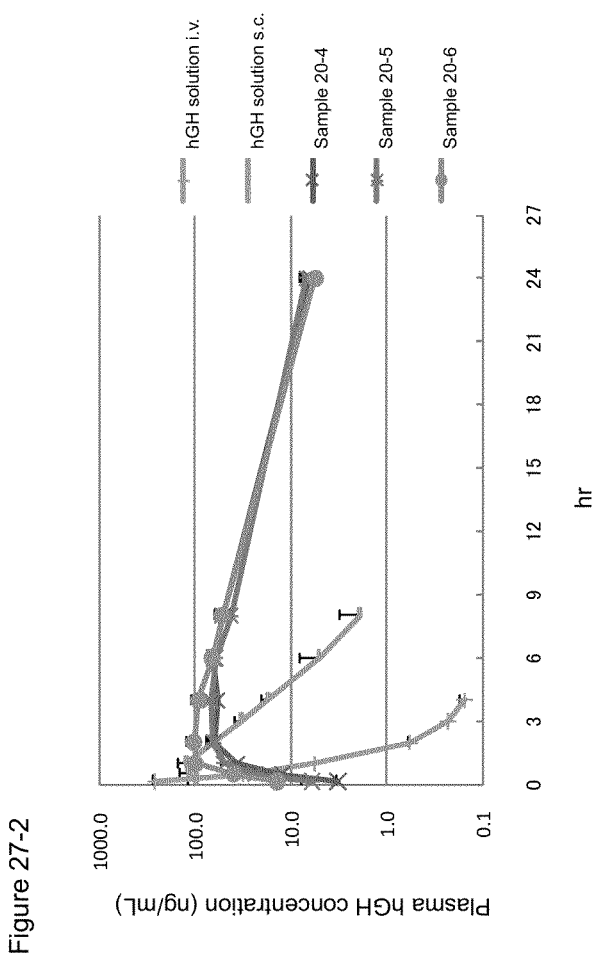
Figure 28:
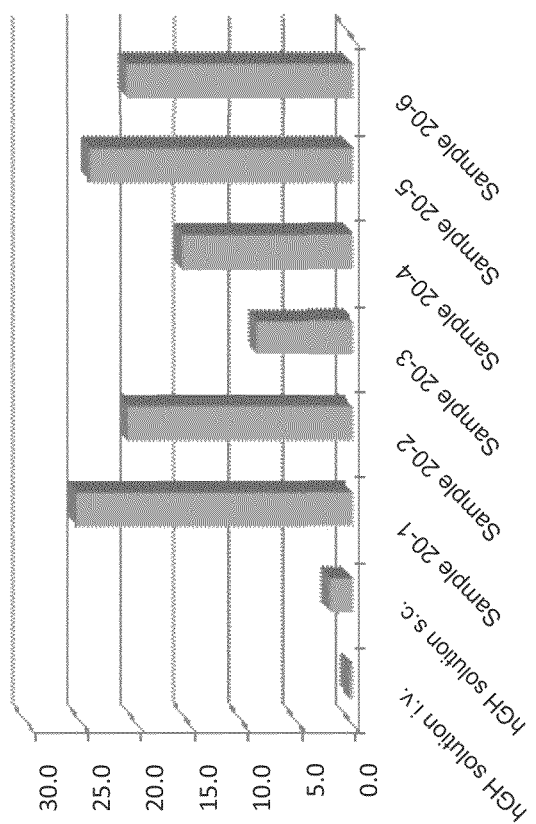
FIG. 28 is a graph showing the mean residence time (MRT) of the hGH/HA derivative complexes of Samples 20-1 to 20-6 of Table 23-1 and the hGH solutions of Comparative Example 1.

Sustained-Release Test in Rats Subcutaneously Administered with hGH/HA Derivative Complex The hGH/HA derivative complexes prepared in Examples 20-1 to 20-3 were subcutaneously administered to normal rats (SD, 6 weeks of age, male) with a 25G-needle at the dose indicated in Table 23-1. The lyophilization product prepared in Example 20-1 was suspended in PBS immediately before administration and then administered. The formulation before administration is shown in FIG. 25. After administration, blood was collected over time from the jugular vein using a heparin-treated syringe, and aprotinin was added as a protease inhibitor. The resulting blood was treated to separate plasma, and the hGH concentration was measured with an ELISA kit (Roche Applied Science). The time course of plasma hGH concentration at the time of administration of various hGH/HA derivative complexes and the time course of plasma concentration of hGH solution of Comparative Example 1 are shown in FIGS. 26-1 to 27-2. Further, pharmacokinetic parameters (extrapolated area under the plasma concentration-time curve (AUC∞) and mean residence time (MRT)) were analyzed by WinNonlin Ver.5.0.1 (Pharsight). The values are shown in Table 23-2. The graph of MRT is shown in FIG. 28.

TABLE 23-1

Dose of hGH/HA derivative complex

| Sample | HA derivative | Formulation | hGH dose (mg/kg) |
|---|---|---|---|
| Sample 20-1 | 50k HA-$C_{12}$-Chol-7% | Lyophilized precipitate formulation | 3.3 |
| Sample 20-2 | 99k HA-$C_{12}$-Chol-7% | Lyophilized precipitate formulation | 3.3 |
| Sample 20-3 | 50k HA-$C_6$-Chol-7% | Lyophilized precipitate formulation | 3.3 |
| Sample 20-4 | 50k HA-$C_6$-Chol-14% | Lyophilized precipitate formulation | 3.3 |
| Sample 20-5 | 50k HA-$C_6$-Chol-14% | Precipitate formulation | 3.3 |
| Sample 20-6 | 50k HA-$C_6$-Chol-14% | Solution formulation | 3.3 |

TABLE 23-2

Pharmacokinetic parameters of hGH/HA derivative complex

| Sample | hGH dose (mg/kg) | AUC∞ (ng · hr/mL) | MRT (time) |
|---|---|---|---|
| Sample 20-1 | 3.3 | 662 | 25.6 |
| Sample 20-2 | 3.3 | 916 | 20.8 |
| Sample 20-3 | 3.3 | 2186 | 8.8 |
| Sample 20-4 | 3.3 | 882 | 15.7 |
| Sample 20-5 | 3.3 | 964 | 24.3 |
| Sample 20-6 | 3.3 | 1127 | 20.9 |

The above results show that the behavior of hGH release from the hGH/HA derivative precipitate formulation had sustained-release properties also in vivo, and that the solution formulation also had sustained-release properties by forming a precipitate in the subcutis. Especially the solution formulation (Sample 20-6) obtained in Example 20-3 is useful as a pharmaceutical formulation, because it can be sterilized with a 0.2-μm filter and is less likely to clog a syringe needle.

Comparative Example 2

Pharmacokinetic Study on HA Derivative (HA-FL) Modified with 5-Aminomethylfluorescein and HA Derivative (HA-$C_2$—OH/FL) Modified with 5-Aminomethylfluorescein and Ethanolamine Comparative Example 2-1

Preparation of HA-FL Using 10 kDa HA-Na and 50 kDa HA-Na

An anhydrous DMSO solution (10 mg/mL) of HA-TBA prepared by the same process as in Example 2-2 using HA-Na having a molecular weight of 10 kDa and HA-Na having a molecular weight of 50 kDa as raw materials was prepared. Then, 5-aminomethylfluorescein (FL) hydrochloride and DMT-MM were added at the ratios (mol %) of 4.4% and 4.0% relative to HA-TBA units, respectively, and stirred overnight at room temperature. Treatments thereafter are the same as those shown in Example 2-3-1, whereby intended products (10 k HA-FL and 50 k HA-FL) were obtained as yellow solids.

Comparative Example 2-2

Preparation of HA-$C_2$—OH/FL using 10 kDa HA-Na (No. 1)

An anhydrous DMSO solution (10 mg/mL) of HA-TBA prepared by the same process as in Example 2-2 using HA-Na having a molecular weight of 10 k as a raw material was prepared. Then, ethanolamine (HO—$C_2$) hydrochloride and DMT-MM were added at the ratios indicated in Table 24 below, and stirred at room temperature for 4 hours. Further, 5-aminomethylfluorescein (FL) hydrochloride and DMT-MM were added at the ratios indicated in Table 24 below, and stirred overnight at room temperature. Treatments thereafter are the same as those shown in Example 2-3-1, whereby an intended product (10 k HA-$C_2$—OH/FL) was obtained as a yellow solid. From the $^1$H-NMR spectrum (JNM-ECA500 JEOL Ltd.) using DMSO-$d_6$ as a measurement solvent, a total introduction ratio of $C_2$—OH and FL was calculated from NHCO derived from an amide group(s) of glucosamine calculated according to the formula shown in Example 13, $C_2$—OH, and NHCO derived from an amide group(s) of FL. This is shown in Table 24.

TABLE 24

Amount of reagent used in HA-$C_2$-OH/FL and results of synthesis

| Abbreviation | Added molar ratio of HO-$C_2$ hydrochloride and DMT-MM (HA-TBA unit/DMT-MM/HO-$C_2$ hydrochloride) Added molar ratio of FL hydrochloride and DMT-MM (HA-TBA unit/DMT-MM/FL hydrochloride) | Total introduction ratio (unit %) |
|---|---|---|
| HA-$C_2$-OH-18%/FL | 100/24/26.4<br>100/4/4.4 | 18 |

Comparative Example 2-3

Preparation of 10 k HA-$C_2$—OH/FL (No. 2)

An anhydrous DMSO solution (10 mg/mL) of HA-TBA prepared by the same process as in Example 2-2 using HA-Na having a molecular weight of 10 k as a raw material was prepared. Then, 5-aminomethylfluorescein (FL) hydrochloride and DMT-MM were added at the ratios indicated in Table 25 below, and stirred overnight at room temperature. Further, ethanolamine ($C_2$—OH) hydrochloride and DMT-MM were added at the ratios indicated in Table 25 below, and stirred at room temperature for 5 hours. Treatments thereafter are the same as those shown in Example 2-3-1, whereby intended 10 k HA-$C_2$—OH/FL was obtained as a yellow solid. A total introduction ratio of $C_2$—OH and FL was calculated by the same procedure as in Comparative Example 2-2. This is shown in Table 25.

TABLE 25

Amount of reagent used in synthesis of HA-$C_2$-OH/FL and results of synthesis

| Abbreviation | Added molar ratio of FL hydrochloride and DMT-MM (HA-TBA unit/DMT-MM/FL hydrochloride) Added molar ratio of HO-$C_2$ hydrochloride and DMT-MM (HA-TBA unit/DMT-MM/HO-$C_2$ hydrochloride) | Total introduction ratio (unit %) |
|---|---|---|
| HA-$C_2$-OH-96%/FL | 100/4/4.4<br>100/150/300 | —<br>96 |

Comparative Example 2-4

Pharmacokinetic Study

Figure 29:
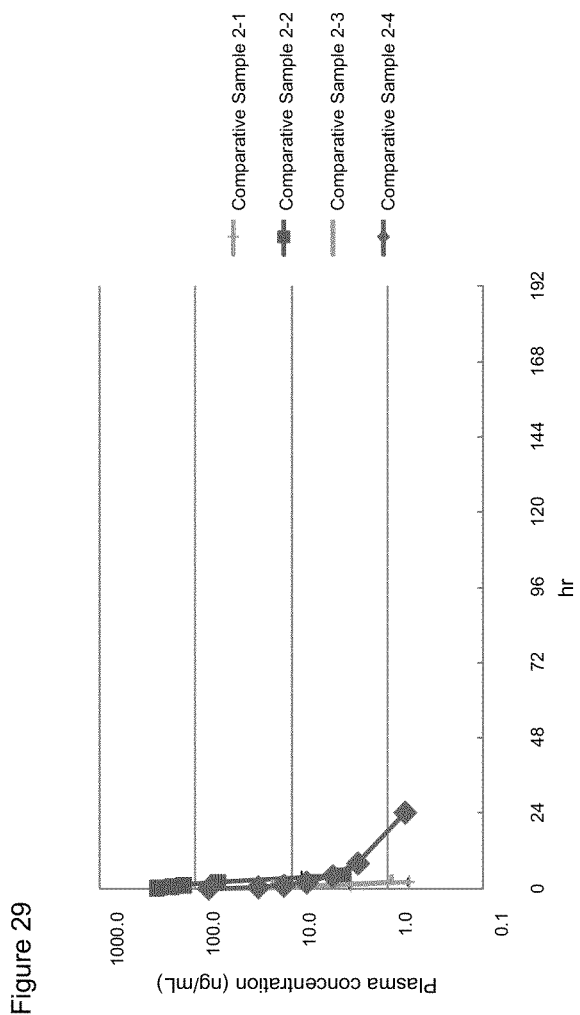
FIG. 29 is a graph showing the time course of plasma concentration of fluorescence-labeled HA derivatives prepared in Comparative Examples 2-1 to 2-3 in rats administered with the fluorescence-labeled HA derivatives.

The fluorescence-labeled HA derivatives prepared in Comparative Examples 2-1 to 2-3 were administered to tail veins of normal rats (SD, 6 weeks of age, male) with a 25G-needle at the dosage indicated in Table 26. After administration, blood was collected over time from the jugular vein using a heparin-treated syringe. The resulting blood was treated to separate plasma, diluted 2-fold with HP-β-CD (100 mM)/tris buffer solution (500 mM, pH 9.0), and incubated at 37° C. for 1 hour. Then, the concentration of each fluorescence-labeled HA derivative was measured by a 96-well plate reader (ARVO). The time course of plasma concentration of each fluorescence-labeled HA derivative is shown in FIG. 29. Further, the pharmacokinetic parameter (extrapolated area under the plasma concentration-time curve (AUC∞)) was analyzed by WinNonlin Ver.5.0.1 (Pharsight). The value is shown in Table 26.

TABLE 26

Dose and pharmacokinetic parameter of fluorescence-labeled HA derivative

| Sample | Fluorescence-labeled HA derivative | Dose (mg/kg) | AUC∞ (μg · hr/mL) |
|---|---|---|---|
| Comparative Sample 2-1 | 10k HA-FL | 10 | 27 |
| Comparative Sample 2-2 | 50k HA-FL | 10 | 314 |
| Comparative Sample 2-3 | 10k HA-$C_2$-OH-18%/FL | 10 | 29 |
| Comparative Sample 2-4 | 10k HA-$C_2$-OH-96%/FL | 10 | 90 |

From the results it became clear that the sample prepared using 10 k of HA-Na as a raw material instantaneously disappeared from blood not only in the case of the HA derivative with a low introduction ratio of $C_2$—OH (Comparative Example 2-3) but also in the case of the highly-modified HA derivative (Comparative Example 2-4).

Example 21

Pharmacokinetic Study of HA-Chol-FL

Example 21-1

Effect of Molecular Weight of HA on Time Course of Plasma Concentration

Figures 1, 30:
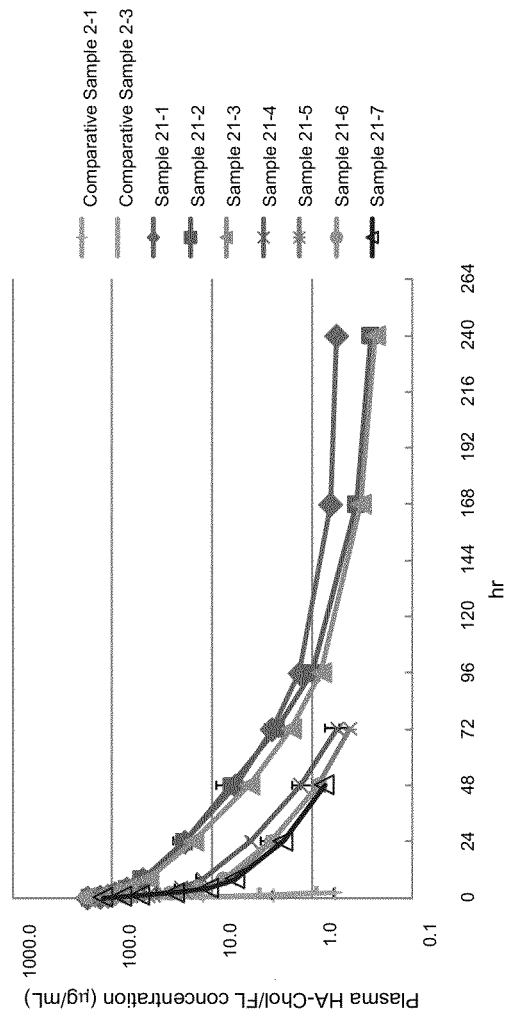
Figures 2, 30:
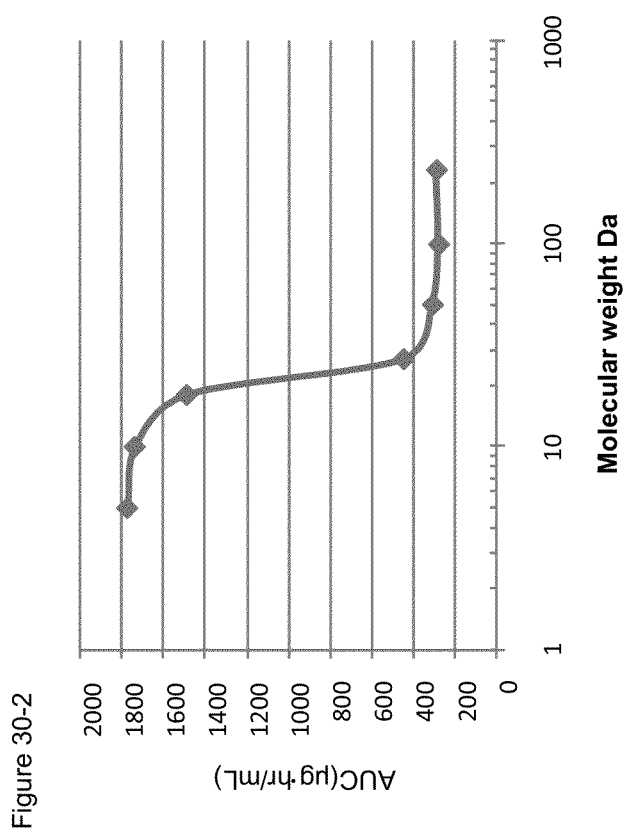

The fluorescence-labeled HA derivatives prepared in Examples 12 and 15 were administered to tail veins of normal rats (SD, 6 weeks of age, male) with a 25G-needle at the dosage indicated in Table 27. After administration, blood was collected over time from the jugular vein using a heparin-treated syringe. The resulting blood was treated to separate plasma, diluted 2-fold with HP-β-CD (100 mM)/tris buffer solution (500 mM, pH 9.0), and incubated at 37° C. for 1 hour. Then, the concentration of each fluorescence-labeled HA derivative was measured by a 96-well plate reader (ARVO). The time course of plasma concentration of each fluorescence-labeled HA derivatives is shown in FIG. 30-1. Further, the pharmacokinetic parameter (extrapolated area under the plasma concentration-time curve (AUC∞)) was analyzed by WinNonlin Ver.5.0.1 (Pharsight). The value is shown in Table 28. The graph of AUC∞ of Table 28 against the molecular weight of raw material HA-Na is shown in FIG. 30-2.

TABLE 27

Dose of fluorescence-labeled HA derivative

| Sample | Fluorescence-labeled HA derivative | Molecular weight of HA | Dose (mg/kg) |
| --- | --- | --- | --- |
| Sample 21-1 | 5k HA-$C_6$-Chol-23%/FL | 5k | 10 |
| Sample 21-2 | 10k HA-$C_6$-Chol-22%/FL | 10k | 10 |
| Sample 21-3 | 18k HA-$C_6$-Chol-15%/FL | 18k | 10 |
| Sample 21-4 | 27k HA-$C_6$-Chol-22%/FL | 27k | 10 |
| Sample 21-5 | 50k HA-$C_6$-Chol-27%/FL | 50k | 10 |
| Sample 21-6 | 99k HA-$C_6$-Chol-25%/FL | 99k | 10 |
| Sample 21-7 | 230k HA-$C_6$-Chol-20%/FL | 230k | 10 |

TABLE 28

Pharmacokinetic parameter of fluorescence-labeled HA derivative

| Sample | AUC∞ (ng · hr/mL) |
| --- | --- |
| Sample 21-1 | 1771 |
| Sample 21-2 | 1735 |
| Sample 21-3 | 1486 |
| Sample 21-4 | 447 |
| Sample 21-5 | 308 |
| Sample 21-6 | 279 |
| Sample 21-7 | 283 |

It is known that an HA derivative having a carboxy group(s) which is not highly modified (e.g. with a modification ratio of 54% or less) instantaneously disappears from blood when intravenously administered, regardless of its molecular weight. Although only 23% at the most (27% or less even when FL is taken into consideration) of substituents were introduced in HA-Chol of the present invention, surprisingly, only HA-Chol prepared using low-molecular-weight (5 k to 18 kDa) hyaluronic acid as a raw material showed excellent residence time in blood.

Example 21-2

Effect of Linker on Time Course of Plasma Concentration

Figure 31:
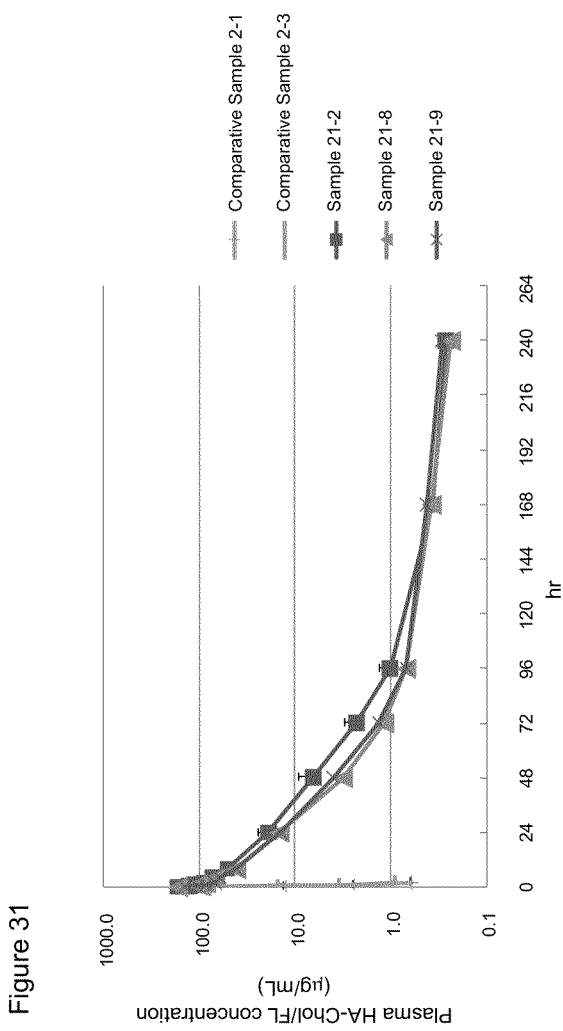
FIG. 31 is a graph showing the time course of plasma concentration of fluorescence-labeled HA derivatives of Samples 21-2, 21-8, and 21-9 of Table 29 in rats administered with the fluorescence-labeled HA derivatives.

Pharmacokinetic studies of the fluorescence-labeled HA derivatives with different linkers prepared in Example 15 and shown in Table 29 were carried out by the same procedure as in Example 21-1. The time course of plasma concentration is shown in FIG. 31. Further, the pharmacokinetic parameter (AUC∞) was calculated by the same procedure as in Example 21-1. The value is shown in Table 30.

TABLE 29

Dose of fluorescence-labeled HA derivative

| Sample | Fluorescence-labeled HA derivative | Linker | Dose (mg/kg) |
| --- | --- | --- | --- |
| Sample 21-2 | 10k HA-$C_6$-Chol-22%/FL | C6 | 10 |
| Sample 21-8 | 10k HA-$C_2$-Chol-22%/FL | C2 | 10 |
| Sample 21-9 | 10k HA-EO2-Chol-20%/FL | EO2 | 10 |

TABLE 30

Pharmacokinetic parameter of fluorescence-labeled HA derivative

| Sample | AUC∞ (ng · hr/mL) |
| --- | --- |
| Sample 21-2 | 1735 |
| Sample 21-8 | 1340 |
| Sample 21-9 | 1320 |

It became clear that HA-Chol prepared using low-molecular-weight hyaluronic acid as a raw material had excellent residence time in blood, regardless of the type of a linker.

Example 21-3

Effect of Introduction Ratio of Chol on Time Course of Plasma Concentration

Figures 1, 32:
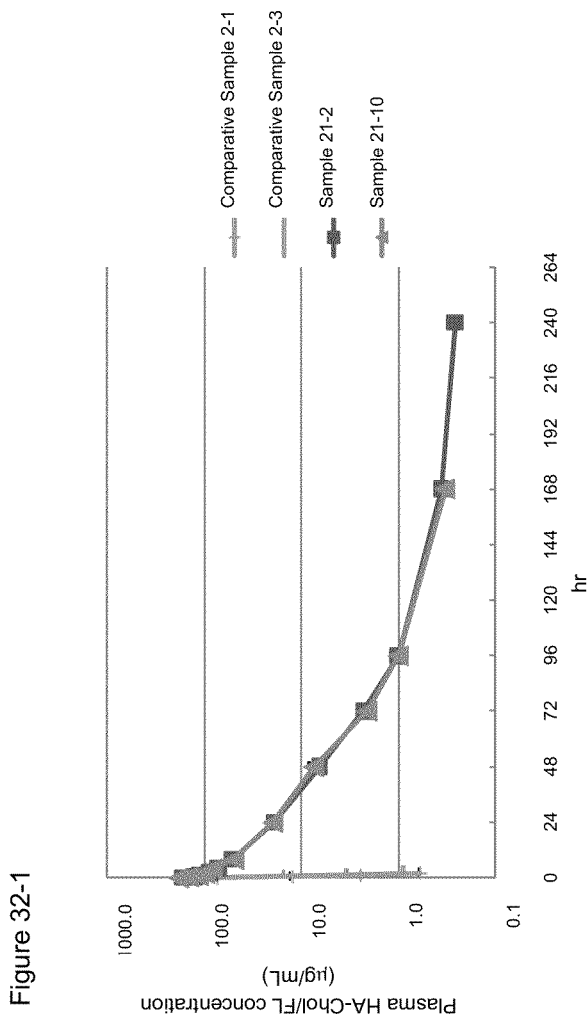
Figures 2, 32:
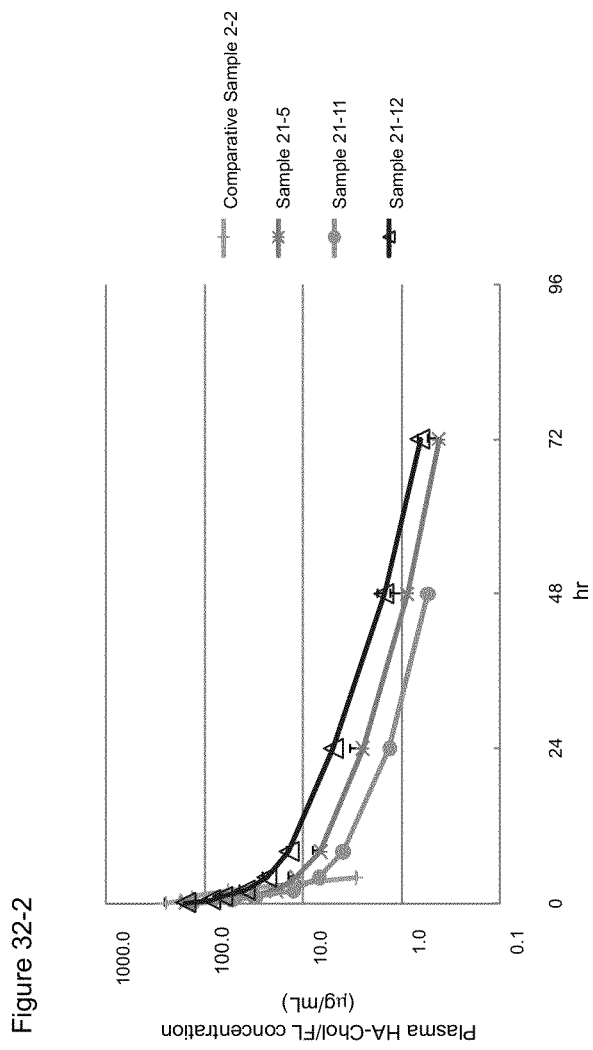

Pharmacokinetic studies of fluorescence-labeled HA derivatives with different introduction ratios of chol prepared in Examples 12 and 15 and shown in Table 31 were carried out by the same procedure as in Example 21-1. The time course of plasma concentration is shown in FIGS. 32-1 and 32-2. Further, the pharmacokinetic parameter (AUC∞) was calculated by the same procedure as in Example 21-1. The value obtained is shown in Table 32.

TABLE 31

Dose of fluorescence-labeled HA derivative

| Sample | Fluorescence-labeled HA derivative | Molecular weight of HA | Introduction ratio | Dose (mg/kg) |
|---|---|---|---|---|
| Sample 21-10 | 10k HA-$C_6$-Chol-15%/FL | 10k | 15 | 10 |
| Sample 21-2 | 10k HA-$C_6$-Chol-22%/FL | 10k | 22 | 10 |
| Sample 21-11 | 50k HA-$C_6$-Chol-20%/FL | 50k | 20 | 10 |
| Sample 21-5 | 50k HA-$C_6$-Chol-27%/FL | 50k | 27 | 10 |
| Sample 21-12 | 50k HA-$C_6$-Chol-34%/FL | 50k | 34 | 10 |

TABLE 32

Pharmacokinetic parameter of fluorescence-labeled HA derivative

| Sample | AUC∞ (ng·hr/mL) |
|---|---|
| Sample 21-10 | 1734 |
| Sample 21-2 | 1735 |
| Sample 21-11 | 201 |
| Sample 21-5 | 308 |
| Sample 21-12 | 536 |

It became clear that the introduction ratio of cholesteryl groups did not have any significant effect on the residence time in blood of HA-Chol.

Example 21-4

Time Course of Plasma Concentration
(HA-Chol/$C_2$—OH/FL)

Figure 33:
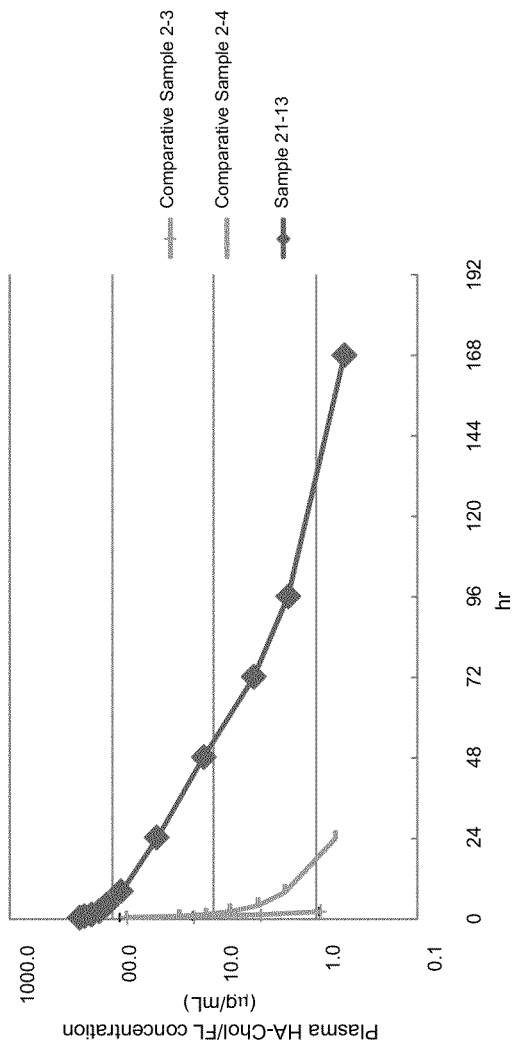
FIG. 33 is a graph showing the time course of plasma concentration of a fluorescence-labeled HA derivative of Sample 21-13 of Table 33 in rats administered with the fluorescence-labeled HA derivative.

Pharmacokinetic studies of the fluorescence-labeled HA derivative prepared in Example 13 and shown in Table 33 which was highly modified with $C_2$—OH and Chol were carried out by the same procedure as in Example 21-1. The time course of plasma concentration is shown in FIG. 33. Further, the pharmacokinetic parameter (AUC∞) was calculated by the same procedure as in Example 21-1. The value is shown in Table 34.

TABLE 33

Dose of fluorescence-labeled HA derivative

| Sample | Fluorescence-labeled HA derivative | Molecular weight of HA | Introduction ratio | Dose (mg/kg) |
|---|---|---|---|---|
| Comparative Sample 2-3 | HA-$C_2$-OH-18%/FL | 10 | | 10 |
| Comparative Sample 2-4 | HA-$C_2$-OH-96%/FL | 10 | 96 | 10 |
| Sample 21-13 | 10k HA-$C_6$-Chol-19%/$C_2$-OH/FL-95% | 10 | 95 | 10 |

TABLE 34

Pharmacokinetic parameter of fluorescence-labeled HA derivative

| Sample | AUC∞ (ng·hr/mL) |
|---|---|
| Comparative Sample 2-3 | 29 |
| Comparative Sample 2-4 | 90 |
| Sample 21-13 | 2754 |

While 10 k HA-$C_2$—OH which was highly modified only with $C_2$—OH (e.g. with a modification ratio of 96% or more) disappeared from blood relatively fast, 10 k HA-Chol/$C_2$—OH of the present invention of almost the same modification ratio in which a cholesteryl group(s) was partially introduced showed, surprisingly, excellent residence time in blood.

It is known that the residence time in blood of hyaluronic acid is prolonged by highly modifying a carboxy group(s) of the hyaluronic acid (Patent Document 8). However, in a case of using hyaluronic acid and a derivative (salt) thereof having a low molecular weight of about 10 kDa as a raw material, it is difficult to prolong the residence time in blood (AUC) (Example 21-4; Comparative Sample 2-4), which is considered to be due to renal excretion. It becomes clear that even in a case where hyaluronic acid or a derivative (salt) thereof having the same molecular weight is used as a raw material and a carboxy group(s) of the hyaluronic acid is highly modified at the same modification ratio, if the above hydrophobic group(s) is included in the modification, the residence time in blood is prolonged significantly, making it possible to provide a hyaluronic acid derivative which is highly practical as a drug carrier even if the derivative has a low molecular weight (Example 21-4; Sample 21-13).

Example 21-5

Figures 1, 34:
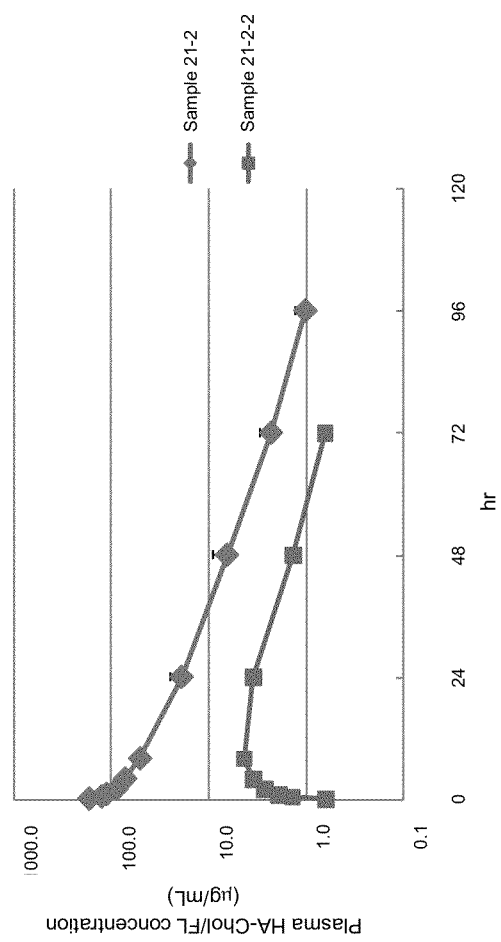
Figures 2, 34:
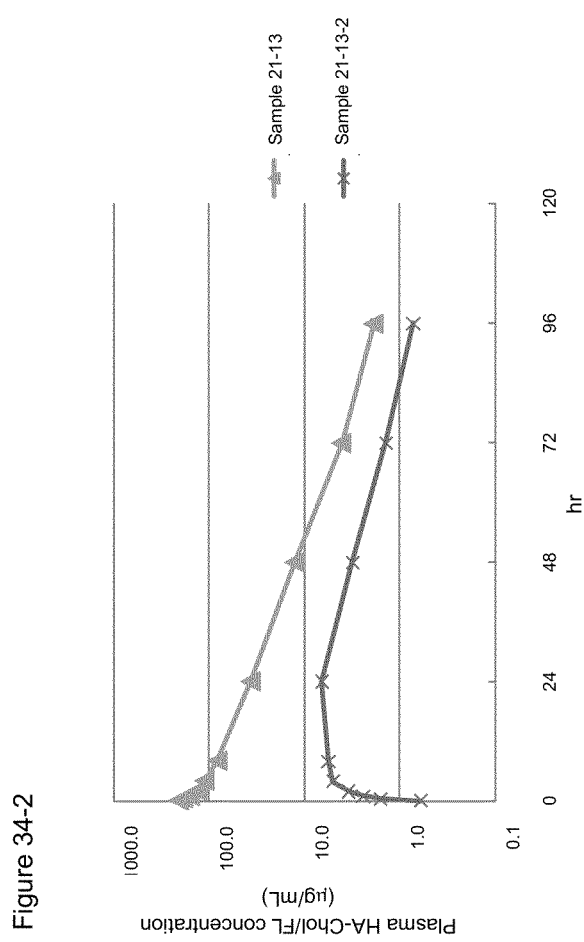

Time Course of Plasma Concentration of HA Derivative After Subcutaneous Administration Except that fluorescence-labeled HA derivatives shown in Table 35 were subcutaneously administered, the procedure of Example 21-1 was repeated to carry out the pharmacokinetic study. The time course of plasma concentration is shown in FIGS. 34-1 and 34-2. Further, the pharmacokinetic parameter (AUC∞) was calculated by the same procedure as in Example 21-1. The value is shown in Table 36.

TABLE 35

Dose of fluorescence-labeled HA derivative

| Sample | Fluorescence-labeled HA derivative | Administration | Dose (mg/kg) |
|---|---|---|---|
| Sample 21-2 | 10k HA-$C_6$-Chol-22%/FL | i.v. | 10 |
| Sample 21-2-2 | 10k HA-$C_6$-Chol-22%/FL | s.c. | 10 |
| Sample 21-13 | 10k HA-$C_6$-Chol-19%/$C_2$-OH/FL-95% | i.v. | 10 |
| Sample 21-13-2 | 10k HA-$C_6$-Chol-19%/$C_2$-OH/FL-95% | s.c. | 10 |

TABLE 36

Pharmacokinetic parameter of fluorescence-labeled HA derivative

| Sample | Administration | AUC∞ (ng · hr/mL) |
|---|---|---|
| Sample 21-2 | i.v. | 1735 |
| Sample 21-2-2 | s.c. | 183 |
| Sample 21-13 | i.v. | 2751 |
| Sample 21-13-2 | s.c. | 346 |

It was suggested that subcutaneous administration of the HA derivative was possible.

Example 21-6

Figures 1, 35:
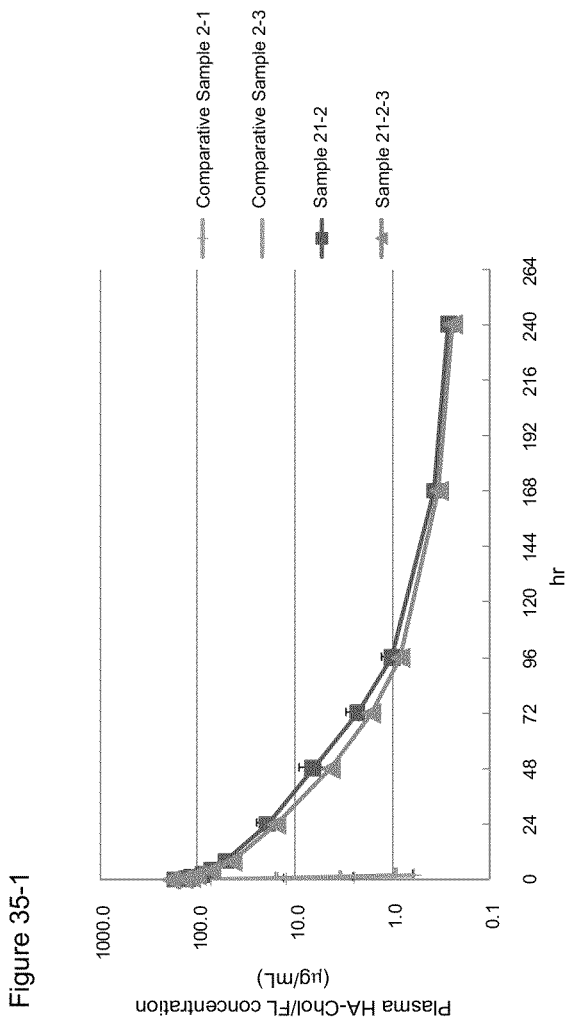
Figures 2, 35:
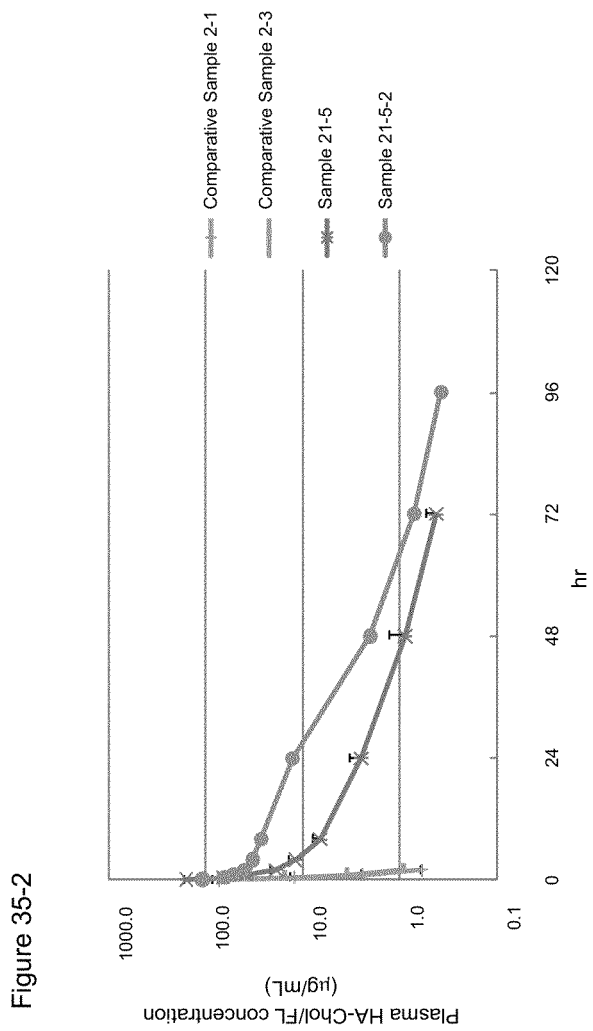

Effect of Preadministration of Hyaluronic Acid on Time Course of Plasma Concentration Except that 30 mg of sodium hyaluronate (mixture containing 1000 k, 300 k, 100 k, 50 k, and 10 k, 6 mg each) was administered to tail veins 20 minutes before administration and thereafter the fluorescence-labeled HA derivative shown in the Table 34 was administered to the tail veins, the procedure of Example 21-1 was repeated to carry out pharmacokinetic studies. The time course of plasma concentration is shown in FIGS. 35-1 and 35-2. Further, the pharmacokinetic parameter (AUC∞, MRT) was calculated by the same procedure as in Example 21-1. The value obtained is shown in Table 38.

TABLE 37

Dose of fluorescence-labeled HA derivative

| Sample | Fluorescence-labeled HA derivative | Administration of HA | Dose (mg/kg) |
|---|---|---|---|
| Sample 21-2 | 10k HA-$C_6$-Chol-22%/FL | Not administered | 10 |
| Sample 21-2-3 | 10k HA-$C_6$-Chol-22%/FL | Administered | 10 |
| Sample 21-5 | 50k HA-$C_6$-Chol-27%/FL | Not administered | 10 |
| Sample 21-5-2 | 50K HA-$C_6$-Chol-27%/FL | Administered | 10 |

TABLE 38

Pharmacokinetic parameter of fluorescence-labeled HA derivative

| Sample | Administration of HA | AUC∞ (ng · hr/mL) |
|---|---|---|
| Sample 21-2 | Not administered | 1735 |
| Sample 21-2-3 | Administered | 1889 |
| Sample 21-5 | Not administered | 308 |
| Sample 21-5-2 | Administered | 805 |

In the case of Sample 21-2-3, HA caused almost no change to pharmacokinetics of Sample 21-2-3, showing that intrinsic metabolism of HA in the liver was avoided. On the other hand, in the case of Sample 21-5-2, the pharmacokinetics were improved by preadministration of HA, showing that the metabolic system of HA was involved in the disappearance of a hyaluronic acid derivative.

Example 21-7

SEC Analysis of Plasma Sample

Figures 1, 36:
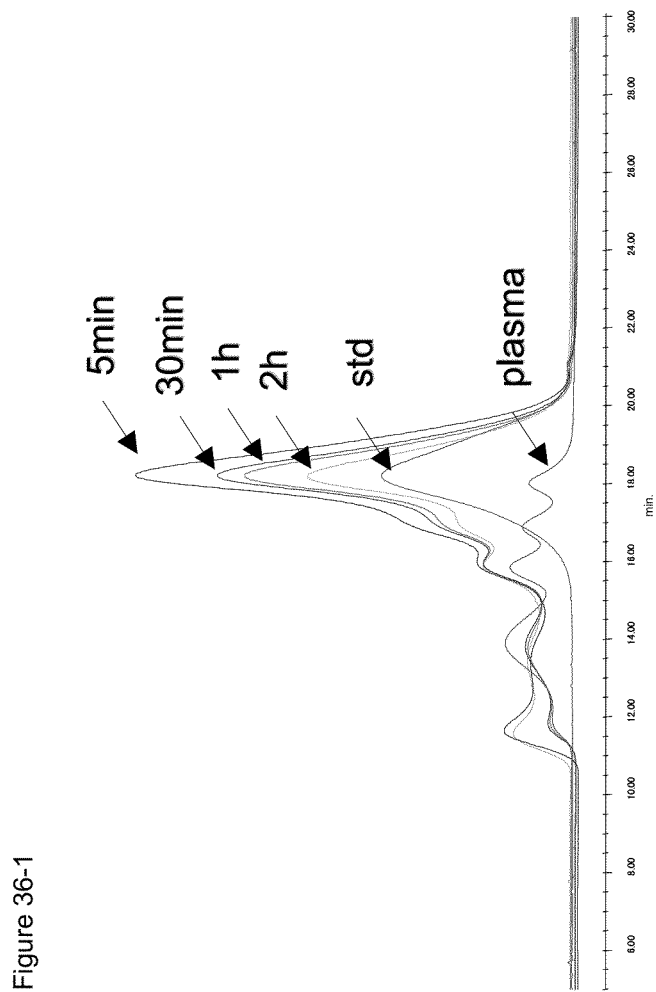
Figures 2, 36:
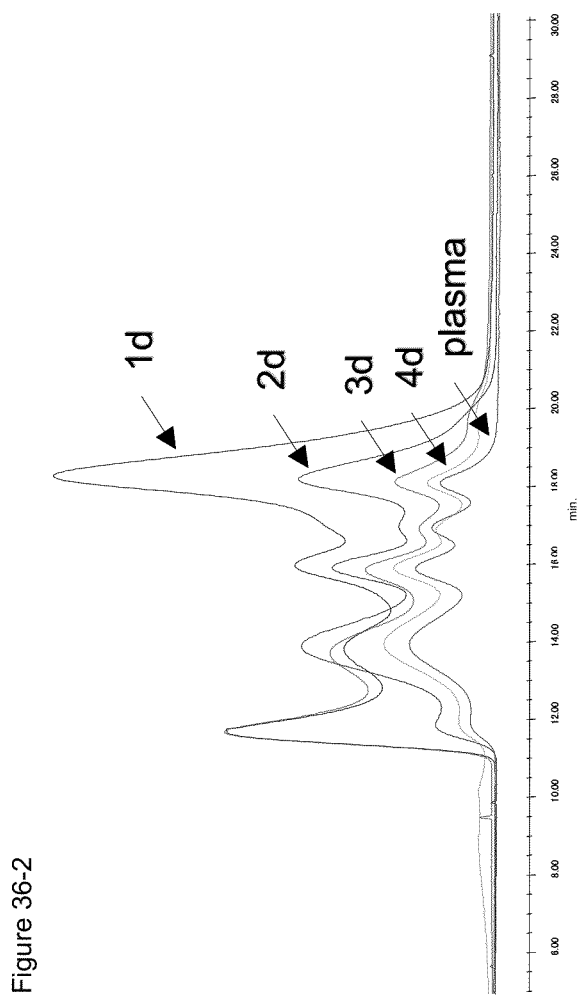

To 20 μL of Sample 21-2 which was subjected to plate reader measurement in Example 21-1, 80 μL of ultrapure water was added, and SEC analysis was carried out. The chromatogram is shown in FIGS. 36-1 and 36-2.

SEC Measurement Conditions

Column: G5000PWXL (Tosoh Corporation, Japan)

Eluent: HP-β-CD (10 mM)/tris buffer solution (500 mM, pH 9.0)

Flow rate: 0.5 mL/min

Amount of injection: 50 μL

Detection: Fluorescence 494/515

The peak of the plasma sample was the same as the peak position of the sample before administration. This suggests that the fluorescence detected by the plate reader was not derived from a decomposition product of HA-Chol-FL.

Example 21-8

SEC Analysis of Urine Sample

Figures 1, 37:
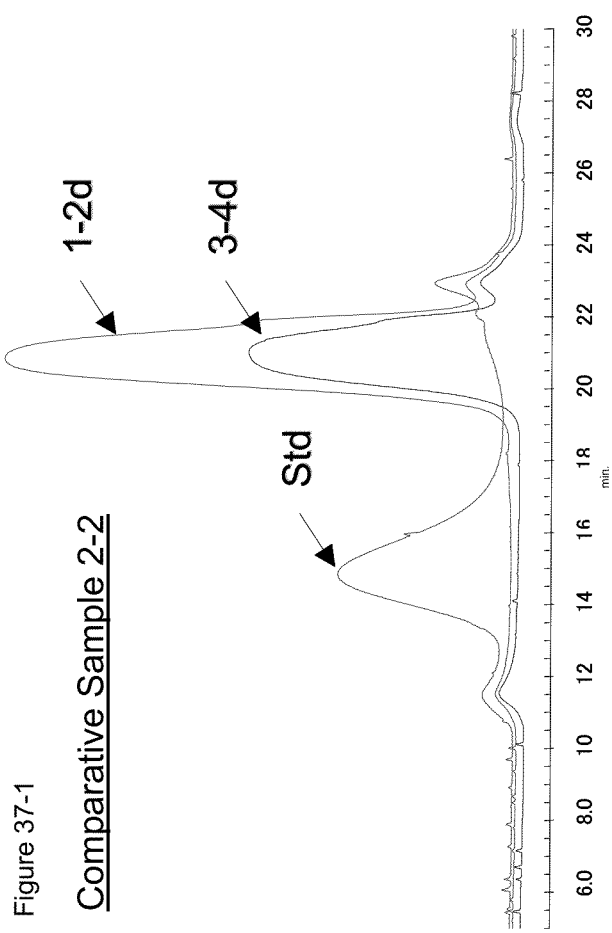
Figures 2, 37:
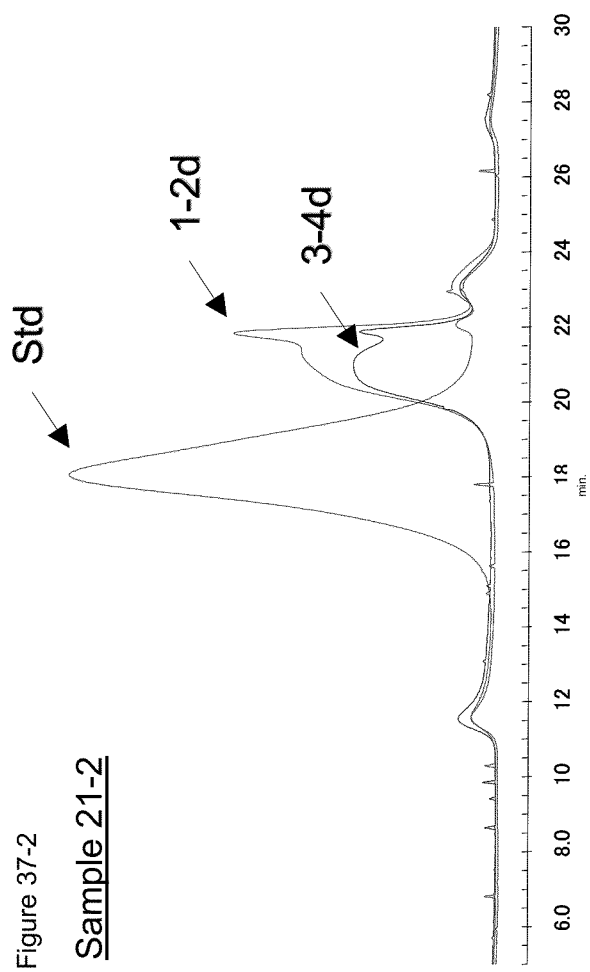
Figures 3, 37:
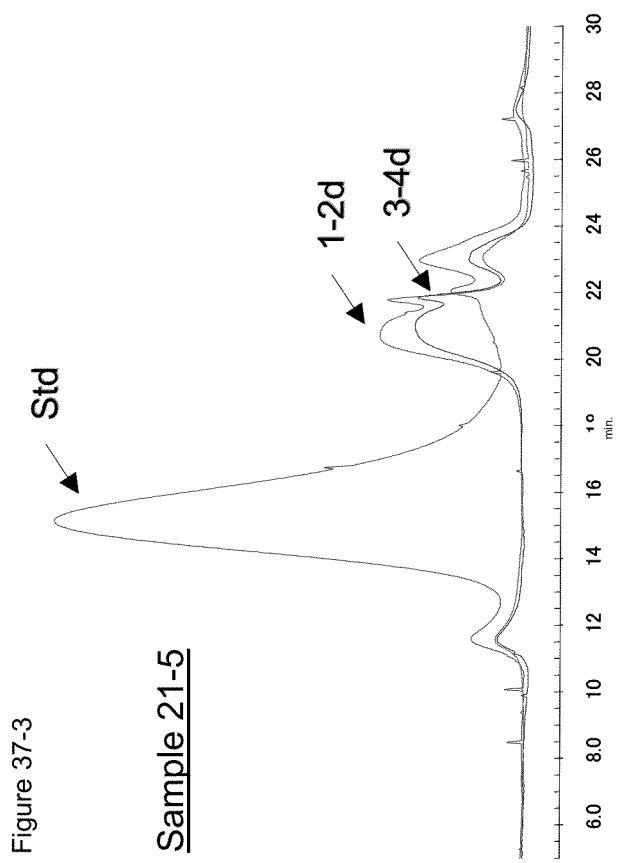
Figures 4, 37:
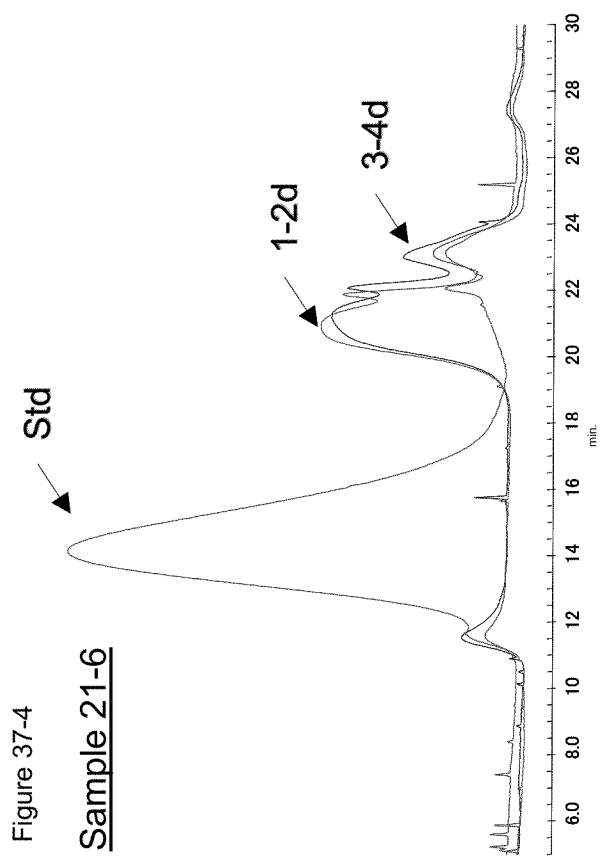
Figures 5, 37:
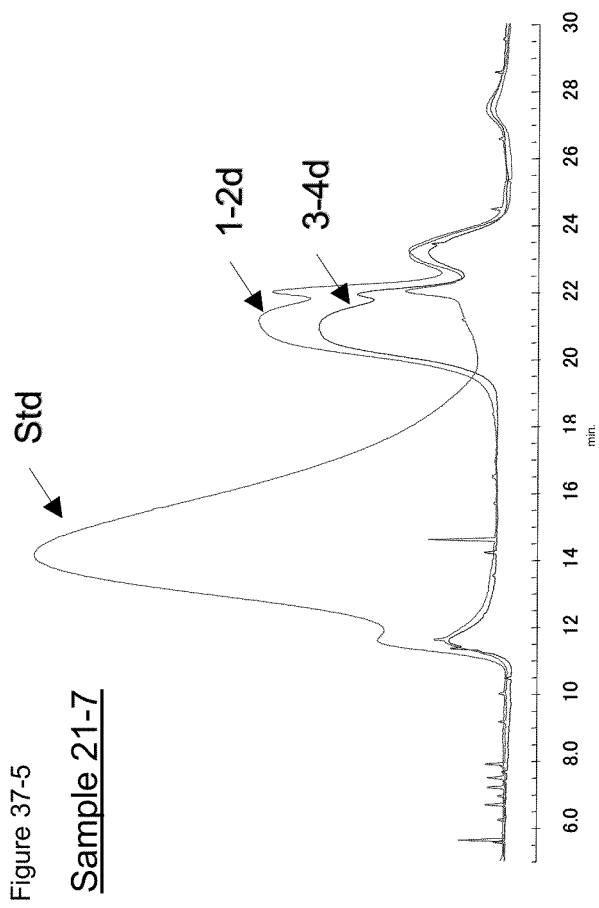

Urine samples were collected simultaneously with the pharmacokinetic studies in rats in Example 21-1 and Comparative Example 2-4. To 50 μL of urine sample, a solution (50 μL) of HP-β-CD (100 mM) and tris buffer solution (500 mM, pH 9.0) was added, and the mixture was incubated at 37° C. for 1 hour and then subjected to SEC analysis. The chromatogram is shown in FIGS. 37-1 to 37-5.

SEC Measurement Conditions

Column: G5000PWXL (Tosoh Corporation, Japan)

Eluent: Solution of HP-β-CD (10 mM) and tris buffer solution (500 mM, pH 9.0)

Flow rate: 0.5 mL/min

Amount of injection: 50 μL

Detection: Fluorescence 494/515

The peak of the urine sample is eluted after the peak position of the sample before administration, suggesting that HA-Chol-FL was decomposed via a route. It is, therefore, shown that HA-Chol-FL forms particles with excellent biodegradability and residence time in blood. In terms of safety, it is significantly advantageous to have biodegradability.

Example 22

Precipitability and Dispersibility of Cholesteryl Group-Introduced HA Derivative (No. 2)

Figure 38:
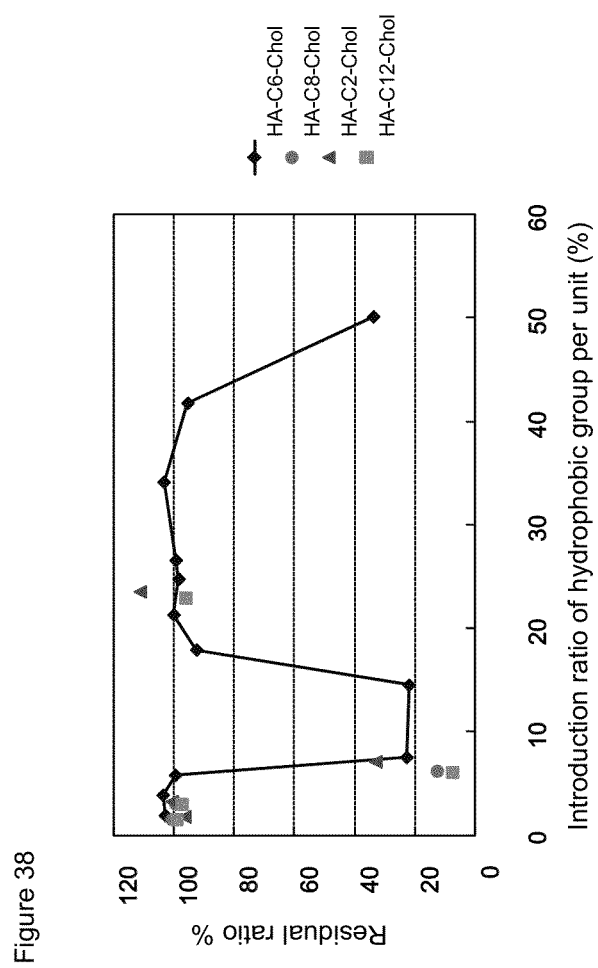
FIG. 38 is a graph of the residual ratio of the HA derivative in the solution calculated in Example 22 against the introduction ratio of hydrophobic groups of the HA derivative.

Except that the HA derivatives obtained in Examples 2-3-2 to 2-3-4 were used, the residual ratio was calculated by the same procedure as in Example 7. The graph of the residual ratio against the introduction ratio of hydrophobic groups of each HA derivative is shown in FIG. 38.

It became clear that in the cases of linkers $C_2$, $C_8$, and $C_{12}$, there were also a range in which the derivative was precipitated and a range in which the derivative was stably dispersed, as in the case of linker $C_6$.

Example 23

Figure 39:
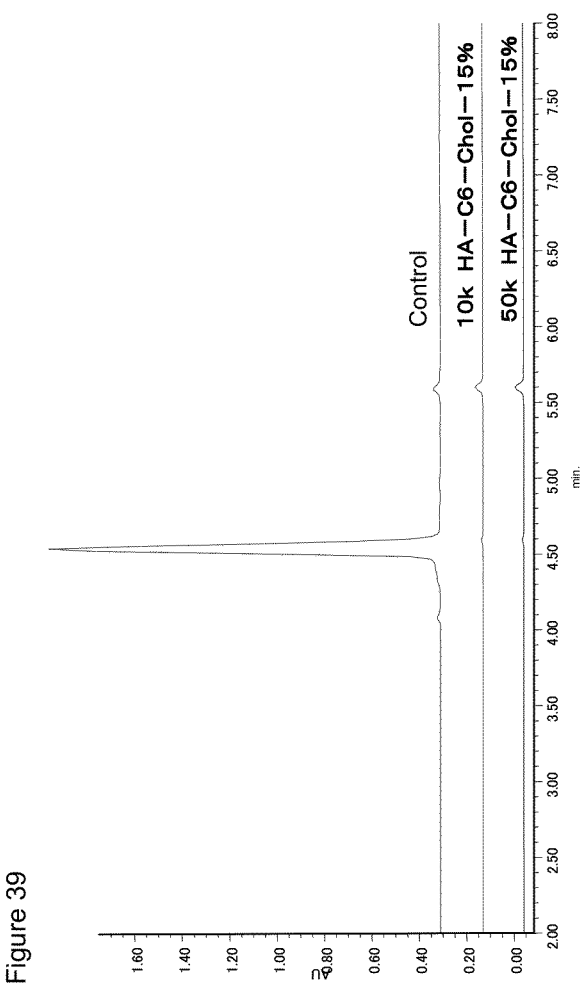
FIG. 39 is a chart showing the results of reversed-phase chromatography of filtrates obtained by ultrafiltration of mixtures of HA derivatives prepared in Example 2-3 or Example 14 and doxorubicin to observe the amount of free doxorubicin (Example 23).

Preparation of Complex of Cholesteryl Group-Introduced HA Derivative and Low-Molecular-Weight Drug An aqueous solution (10 mg/mL, 4 μL, Wako Pure Chemical Industries, Ltd.) of doxorubicin (DOX) was added to an aqueous solution (6 mg/mL, 100 μL) of 10 k HA-$C_6$-Chol-15% prepared in Example 14 or 50 k HA-$C_6$-Chol-15% prepared in Example 2-3-1, and 96 μL of concentrated PBS solution was added to give a final concentration of 1×PBS. In place of the aqueous solution of DOX, ultrapure water was added to prepare a control. After incubation at room temperature for 1 hour, the mixture was subjected to centrifugal filtration in an ultrafiltration device (Microcon, molecular weight cutoff 10,000), and the filtrate was subjected to HPLC (reversed-phase, RP). Free DOX that was not complexed with the HA derivative was detected. The chromatogram is shown in FIG. 39.

RP Measurement Conditions
Column: Cadenza CD-$C_{18}$ (Imtakt)
Eluent A: Ultrapure water, 0.1% TFA
Eluent B: Acetonitrile, 0.1% TFA
Gradient: B5%→B95% (8 min)
Flow rate: 0.75 mL/min.
Amount of injection: 10 μL
Detection: UV 480

It became clear that by mixing the HA derivative of the present invention with doxorubicin, a complex was formed.

Example 24

HA-Chol In Vivo Imaging

Figure 40:
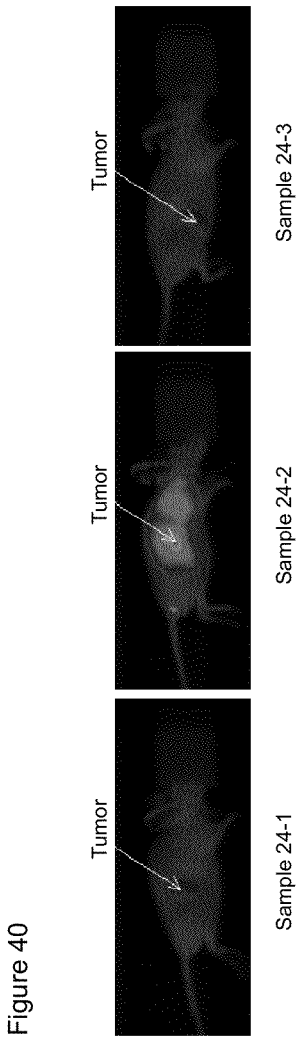
FIG. 40 shows photographs taken by an in vivo imaging system to evaluate accumulation of Hilyte-labeled HA derivative and 50 k HA-Hilyte prepared in Examples 16 and 24, respectively, in tumors in xenograft mice administered with the Hilyte-labeled HA derivative and 50 k HA-Hilyte.
Figure 41:
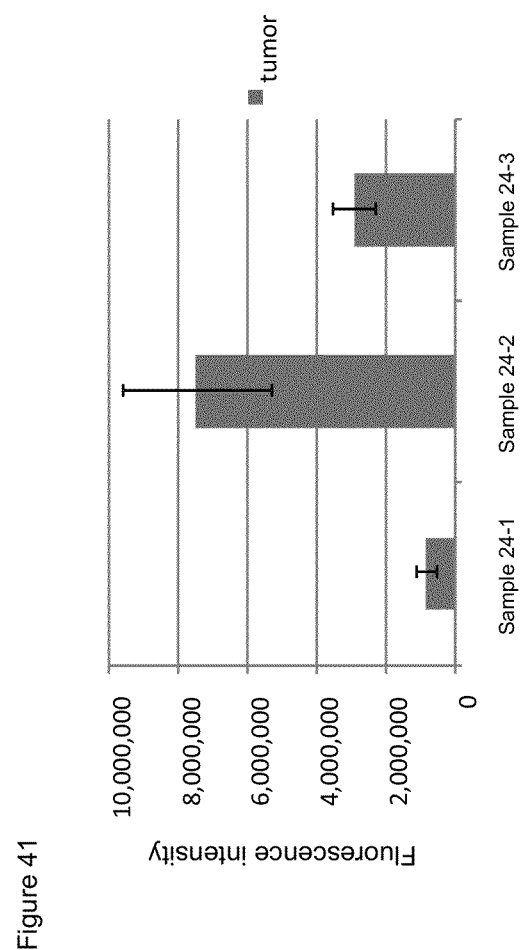
FIG. 41 is a graph of the fluorescence intensity of tumors in xenograft mice administered with the Hilyte-labeled HA derivative and 50 k HA-Hilyte.

A human breast cancer-derived MDA-MB-213 cell fragment (2 mm×2 mm×2 mm) was subcutaneously implanted into nude mice (BALB-nu/nu, female, 7 weeks of age) to thereby prepare xenograft mice. After 17 days, the mice were grouped according to tumor size and weight (analysis software: ANTES, weight 18.8 to 24.3 g, tumor size 215 mm$^3$ to 360 mm$^3$), and the Hilyte-labeled HA derivative prepared in Example 16 and 50 k HA-Hilyte (prepared by the same procedure as in Comparative Example 2-1, except that Hilyte TFA salt was used in place of FL hydrochloride) were administered to tail veins of the mice at the dose indicated in Table 39. After 6 hours, the xenograft mice were photographed with an in vivo imaging system (Night OWL 983, Berthold (700/780 nm, 0.5 msec)). After 24 hours, the tumor was resected and photographed with the in vivo imaging system. All data thus obtained was analyzed by analysis software (Indigo). The in vivo image after 6 hours is shown in FIG. 40. The graph of the light intensity obtained from the tumor is shown in FIG. 41.

TABLE 39

Dose of Hilyte-labeled HA derivative

| Sample | Fluorescence-labeled HA derivative | Dose (mg/kg) |
|---|---|---|
| Sample 24-1 | 50k HA-Hilyte | 40 |
| Sample 24-2 | 10k HA-$C_6$-Chol-22%/Hilyte | 40 |
| Sample 24-3 | 50k HA-$C_6$-Chol-27%/Hilyte | 40 |

From the results it became clear that 10 k HA-$C_6$-Chol (Sample 24-2) had a characteristic that it was more likely to be accumulated in tumors, compared with the unmodified HA (Sample 24-1) or 50 k HA-$C_6$-Chol (Sample 24-3). This shows that by encapsulating an anticancer drug into (or complexing an anticancer drug with) the HA derivative of the present invention or by conjugating an anticancer drug to the HA derivative of the present invention, tumor-specific targeting may be accomplished.

Example 25

Gelation of HA Derivative in which Cholesteryl Group and Methacryloyl Group are Introduced (HA-Chol/AEMA)

Figure 42:
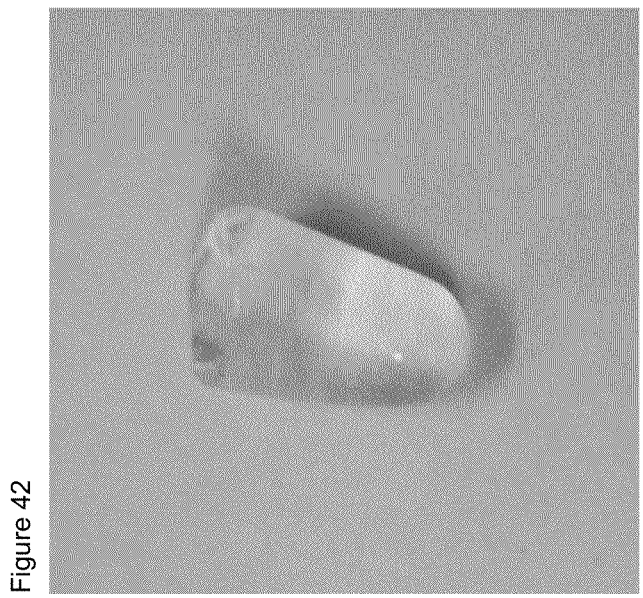
FIG. 42 is a photograph showing a gel formed by crosslinking the HA-Chol/AEMA prepared in Example 11 with DTT.

The (50 k) HA-$C_2$-Chol-8%/AEMA-27% prepared in Example 11 was dissolved in ultrapure water (40 mg/mL, 100 μL), and triethanolamine (TEA, 1.3 μL) was added and mixed. Then, dithiothreitol (DTT, 100 mg/mL, 2.0 μL) was added, and the mixture was incubated in a 500-4, tube at 37° C. After 24 hours, the mixture was removed from the tube. Gelation was confirmed. This is shown in FIG. 42.

From the above results it became clear that HA-Chol/AEMA could be gelled with DTT, and that a dual gel having both physical and chemical crosslinkages by hydrophobic interaction between cholesteryl groups could be prepared. It is expected that this dual gel has a function to stably hold an encapsulated drug, compared with HA-Chol having only physical crosslinkages.

The resulting HA-$C_2$-Chol-8%/AEMA-27% gel was added to 2 mL of 0.93 mg/ml Cy™ 3-labeled hGH solution (red) and incubated at room temperature for 4 days (the Cy™ 3-labeled hGH solution was prepared in accordance with a manual using Cy3 Mono-Reactive Dye Pack (GE Healthcare) and hGH solution); it was confirmed that the Cy™ 3-labeled hGH solution and the gel were stained red which was darker than that of the surrounding solution (data not shown). The results show that after gelation, the HA-Chol/AEMA gel spontaneously encapsulated hGH. In terms of stable encapsulation of a protein, the HA-Chol/AEMA gel is useful as a pharmaceutical matrix.

Example 26

Synthesis of Hyaluronic Acid Derivative in which Cholesteryl Group was Introduced in Hydroxy Group in Position 6 of N-Acetylglucosamine Moiety of Hyaluronic Acid In anhydrous DMSO, 68.26 mg of HA-TBA prepared in Example 2-2 using HA-Na (50 kDa) as a starting material was dissolved. To the resulting mixture, drops of cholesteryl N-(6-isocyanatehexyl)carbamate (CHI, 4.15 mg) dissolved in dehydrated pyridine were added and stirred under nitrogen at 80° C. for 9.5 hours. The reaction solution was precipitated again with ethyl acetate and thereafter recovered by centrifugal separation. The resulting white solid was dissolved again in DMSO and dialyzed against 0.3M NaCl solution, distilled water, 10 mM HCl solution, and distilled water (Slide-A-Lyzer, molecular weight cutoff 3500 Da, PIERCE). The resulting dialysate was lyophilized, whereby 50 k HA-O—$C_6$-Chol was obtained. The introduction ratio of cholesteryl groups relative to HA units calculated from the $^1$H-NMR spectrum (500 MHz, Bruker) using DMSO-$d_6$ as a measurement solvent in accordance with the formula specified in Example 2-3-1 is shown in Table 40.

Further, except that 99 kDa of HA-TBA (102.68 mg) and 4.99 mg of CHI were used, the procedure was repeated to synthesize and obtain 99 k HA-O—C$_6$-Chol. The introduction ratio of cholesteryl groups is shown in Table 40.

TABLE 40

| Abbreviation | Added molar ratio of CHI (HA-TBA unit/CHI) | Chol introduction ratio (unit %) |
|---|---|---|
| 50k HA-O-C$_6$-Chol-1% | 100/7 | 1 |
| 99k HA-O-C$_6$-Chol-2% | 100/6 | 2 |

Amount of reagent used in synthesis of HA-O-C$_6$-Chol and results of synthesis

Example 27

DLS Measurement of Hyaluronic Acid Derivative in which Cholesteryl Group was Introduced in Hydroxy Group in Position 6 of N-acetylglucosamine Moiety of Hyaluronic Acid DLS measurement was carried out by the same procedure as in Example 17, except that 50 k HA-O—C$_6$-Chol-1% and 99 k HA-O—C$_6$-Chol-2% prepared in Example 26 were used and dissolved in ultrapure water as a solvent. The z-average particle size is shown in Table 41.

TABLE 41

Particle size of HA derivative

| Abbreviation | Diameter nm |
|---|---|
| 50k HA-O-C$_6$-Chol-1% | 232 |
| 99k HA-O-C$_6$-Chol-2% | 325 |

The invention claimed is:

1. A hyaluronic acid derivative containing a hydrophobic group, comprising at least one repeating unit represented by the formula (I):

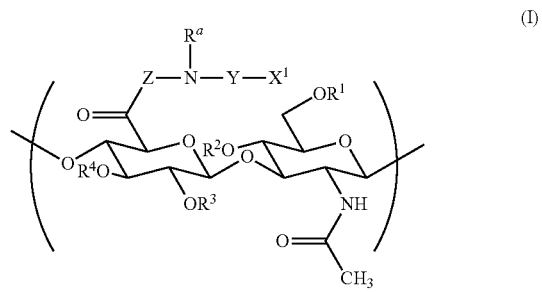

(I)

wherein
$R^1$, $R^2$, $R^3$, and $R^4$ are each independently selected from a hydrogen atom, $C_{1-6}$ alkyl, formyl, and $C_{1-6}$ alkylcarbonyl;
Z represents a direct bond;
$X^1$ is a hydrophobic group selected from the groups represented by the following formulas:
—NR$^b$—COO—R,
R$^a$, and R$^b$ are each independently selected from a hydrogen atom, and $C_{1-6}$ alkyl;
R is a steryl group;
Y is $C_{2-30}$ alkylene or —(CH$_2$CH$_2$O)$_m$—CH$_2$CH$_2$; and
m is an integer selected from 1 to 100.

2. The hyaluronic acid derivative of claim 1, substantially consisting of a repeating unity represented by the formula (I) and a repeating unit represented by the formula (II):

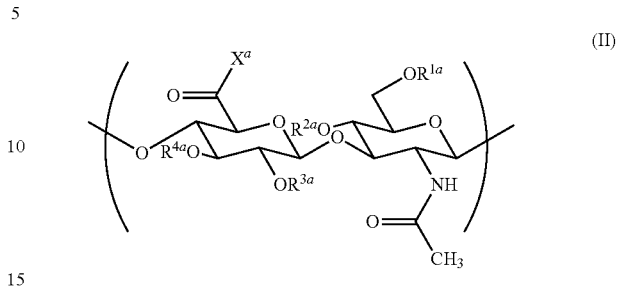

(II)

wherein
$R^{1a}$, $R^{2a}$, $R^{3a}$, and $R^{4a}$ are each independently selected from a hydrogen atom, $C_{1-6}$ alkyl, formyl, and $C_{1-6}$ alkylcarbonyl; and
$X^a$ is selected from hydroxy and —O$^-$Q$^+$, wherein Q$^+$ is a counter cation.

3. The hyaluronic acid derivative of claim 1, wherein an introduction ratio of the hydrophobic group(s) relative to a disaccharide repeating unit(s) present is 7 to 42%; and the introduction ratio is defined according to the following formula:

(Introduction ratio of hydrophobic groups(s))=(Number of repeating units of hydrophobic group-introduced disaccharide×100 divided by (Number of disaccharide repeating units present).

4. The hyaluronic acid derivative of claim 3, wherein the introduction ratio of the hydrophobic group(s) relative to the disaccharide repeating unit(s) present is 7 to 15%, or 18 to 42%.

5. The hyaluronic acid derivative of claim 1, wherein Y is selected from —(CH$_2$)$_2$—, —(CH$_2$)$_6$—, —(CH$_2$)$_8$—, and —(CH$_2$)$_{12}$—.

6. The hyaluronic acid derivative of claim 1, further comprising a repeating unit represented by the formula (III):

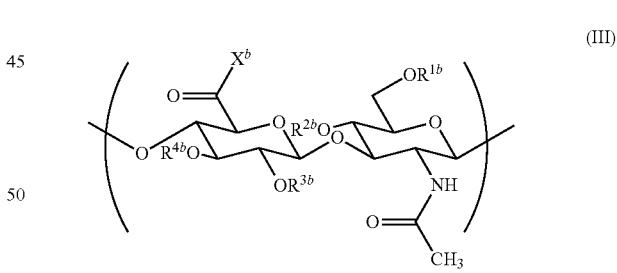

(III)

wherein
$R^{1b}$, $R^{2b}$, $R^{3b}$, and $R^{4b}$ are each independently selected from a hydrogen atom, $C_{1-6}$ alkyl, formyl, and $C_{1-6}$ alkylcarbonyl;
$X^b$ represents —NR$^e$—Y$^b$—R$^d$;
R$^e$ is a hydrogen atom or $C_{1-6}$ alkyl;
R$^d$ is a hydrogen atom, $C_{1-6}$ alkyl, or group —CO—C(R$^7$)=CH$_2$;
Y$^b$ is —CH$_2$—(CHR$^5$)$_{l-2}$—CH$_2$—NH—, —CH$_2$—(CHR$^6$)$_{p-2}$—CH$_2$—O—, —(CH$_2$)$_j$—S—, —CH$_2$—CH$_2$—(Y$^3$—CH$_2$—CH$_2$)$_z$—S—, —CH$_2$—CH$_2$—(Y$^4$—CH$_2$—CH$_2$)$_t$—NH—, or —CH$_2$—CH$_2$—(Y$^5$—CH$_2$—CH$_2$)$_y$—O—, wherein each of l, p, and j is independently an integer selected from 2 to 10, each of z, t, and y is independently an integer selected from 1 to 200, $R^5$ and $R^6$ are each independently a hydrogen atom, $R^7$ is a hydrogen atom or methyl, and $Y^3$, $Y^4$, and $Y^5$ are each independently —O— or —NH—.

7. The hyaluronic acid derivative of claim 6, wherein $X^b$ is —$NR^i$—$(CH_2)_{n2}$—OH wherein $R^i$ is a hydrogen atom and n2 is an integer selected from 2 to 10.

8. The hyaluronic acid derivative of claim 6, wherein a percentage of the repeating unit(s) represented by the formula (II) relative to the disaccharide repeating unit(s) present is 50% or less.

9. The hyaluronic acid derivative of claim 1, further comprising a repeating unit represented by the formula (IV):

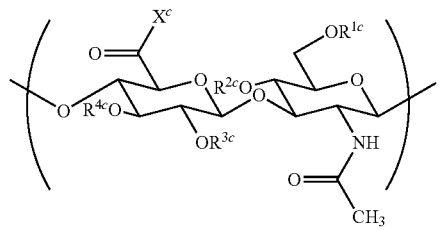

(IV)

wherein
$R^{2c}$, $R^{3c}$, and $R^{4c}$ are each independently selected from a hydrogen atom, $C_{1-6}$ alkyl, formyl, and $C_{1-6}$ alkylcarbonyl;
$X^c$ is selected from hydroxy and —$O^-Q^+$, wherein $Q^+$ is a counter cation;
$R^{1c}$ is selected from
 —CO—C($R^{21}$)=$CH_2$,
 —$CH_2CH(OH)$—$R^{22}$—$Y^1$,
 —$CH(CH_2OH)$—$R^{22}$—$Y^1$,
 —CONH—$R^{23}$—$Y^1$,
 —CO—$R^{23}$—$Y^1$,
 —CONH—$CH_2CH_2$—$(X^{21}$—$CH_2CH_2)_{n3}$—$Y^1$, and
 —CO—$CH_2CH_2$—$(X^{21}$—$CH_2CH_2)_{n4}$—$Y^1$, wherein
$X^{21}$ is selected from O and S;
each of n3 and n4 represents an integer of 1 to 50;
$Y^1$ is selected from amino, mercapto, formyl, and —$X^{14}$—CO—C($R^{18}$)=$CH_2$;
$R^{21}$ is selected from a hydrogen atom and $C_{1-6}$ alkyl;
each of $R^{22}$ and $R^{23}$ are a divalent $C_{2-50}$ hydrocarbon group or a divalent $C_{2-50}$ polyalkyleneoxy group, wherein the divalent $C_{2-50}$ hydrocarbon group may partially contain a polyalkyleneoxy moiety formed by insertion of 1 to 10 —O— atoms;
$X^{14}$ is selected from O and N($R^{19}$);
$R^{18}$ is a hydrogen atom or $C_{1-6}$ alkyl; and
$R^{19}$ is a hydrogen atom or $C_{1-6}$ alkyl.

10. The hyaluronic acid derivative of claim 1, which forms a particle by association in water.

11. A pharmaceutical composition comprising as a carrier the hyaluronic acid derivative of claim 1.

12. The pharmaceutical composition of claim 11, wherein the drug is a pharmacologically active protein or peptide.

13. A hyaluronic acid derivative containing a hydrophobic group, comprising at least one repeating unit represented by the formula (I):

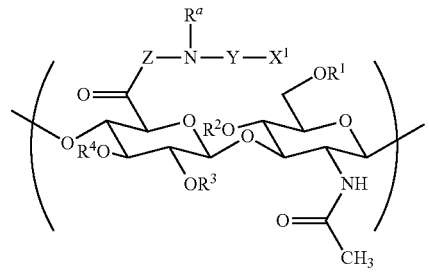

(I)

wherein
$R^1$, $R^2$, $R^3$, and $R^4$ are each independently selected from a hydrogen atom, $C_{1-6}$ alkyl, formyl, and $C_{1-6}$ alkylcarbonyl;
Z represents a direct bond;
$X^1$ is a hydrophobic group selected from the groups represented by the following formulas:
 —$NR^b$—R,
 —$NR^b$—CO—R,
 —$NR^b$—CO—$NR^c$—R,
 —COO—R,
 —O—COO—R,
 —S—R, and
 —S—S—R;
$R^a$, $R^b$, and $R^c$ are each independently selected from a hydrogen atom, $C_{1-20}$ alkyl, amino $C_{2-20}$ alkyl, and hydroxy $C_{2-20}$ alkyl, wherein 1 to 3 groups selected from —O— and —$NR^f$— are optionally inserted in an alkyl moiety of these groups;
$R^f$ is selected from a hydrogen atom, $C_{1-12}$ alkyl, amino $C_{2-12}$ alkyl, and hydroxy $C_{2-12}$ alkyl, wherein 1 or 2 groups selected from —O— and —NH— are optionally inserted in an alkyl moiety of these groups;
R is a steryl group;
Y is $C_{2-30}$ alkylene or —$(CH_2CH_2O)_m$—$CH_2CH_2$—, wherein 1 to 5 groups selected from —O—, —$NR^g$—, and —S—S— are optionally inserted in the alkylene;
$R^g$ is selected from a hydrogen atom, amino $C_{2-20}$ alkyl, and hydroxy $C_{2-20}$ alkyl, wherein 1 to 3 groups selected from —O— and —NH— are optionally inserted in an alkyl moiety of these groups;
m is an integer selected from 1 to 100; and
wherein the hyaluronic acid derivative is produced by using hyaluronic acid or a derivative thereof as a raw material, which has a weight-average molecular weight of 27 kDa or less and substantially consists of the repeating unit represented by the formula (II):

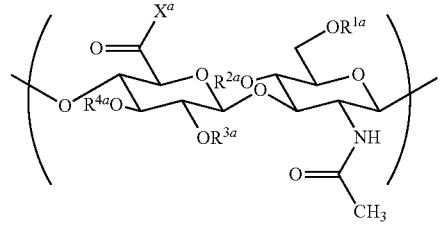

(II)

wherein
$R^{1a}$, $R^{2a}$, $R^{3a}$, and $R^{4a}$ are each independently selected from a hydrogen atom, $C_{1-6}$ alkyl, formyl, and $C_{1-6}$ alkylcarbonyl; and $X^a$ is selected from hydroxy and —O⁻Q⁺, wherein Q⁺ is a counter cation.

14. The hyaluronic acid derivative of claim 13, substantially consisting of a repeating unit represented by the formula (I) and a repeating unit represented by the formula (II):

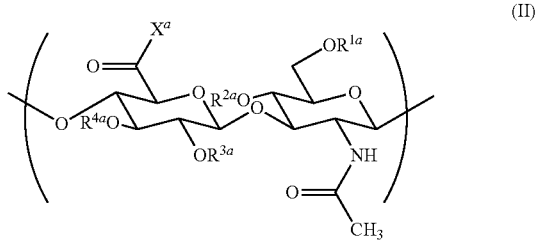

(II)

wherein $R^{1a}$, $R^{2a}$, $R^{3a}$, and $R^{4a}$ are each independently selected from a hydrogen atom, $C_{1-6}$ alkyl, formyl, and $C_{1-6}$ alkylcarbonyl; and $X^a$ is selected from hydroxy and —O⁻Q⁺, wherein Q⁺ is a counter cation.

15. The hyaluronic acid derivative of claim 13, wherein an introduction ratio of the hydrophobic group(s) relative to a disaccharide repeating unit(s) present is 7 to 42%; and the introduction ratio is defined according to the following formula:

(Introduction ratio of hydrophobic group(s)) =

$$\frac{\text{(Number of repeating units of hydrophobic group} - \text{introduced disaccharide)}}{\text{(Number of disaccharide repeating units present)}} \times 100.$$

16. The hyaluronic acid derivative of claim 13, wherein the introduction ratio of the hydrophobic group(s) relative to the disaccharide repeating unit(s) present is 7 to 15%, or 18 to 42%.

17. The hyaluronic acid derivative of claim 13, wherein Y is selected from —(CH₂)₂—, —(CH₂)₆—, —(CH₂)₈—, and —(CH₂)₁₂—.

18. The hyaluronic acid derivative of claim 17, wherein the introduction ratio of the hydrophobic group(s) relative to the disaccharide repeating unit(s) present is 2 to 50%.

19. The hyaluronic acid derivative of claim 17, wherein Y is —(CH₂)ₙ₁— or —(CH₂CH₂O)ₘ₁—CH₂CH₂— wherein n1 is an integer of 2 to 15 and m1 is an integer of 1 to 4.

20. The hyaluronic acid derivative of claim 13, further comprising a repeating unit represented by the formula (III):

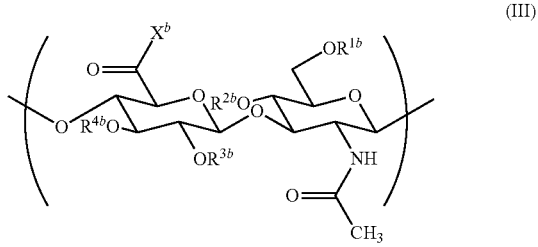

(III)

wherein $R^{1b}$, $R^{2b}$, $R^{3b}$, and $R^{4b}$ are each independently selected from a hydrogen atom, $C_{1-6}$ alkyl, formyl, and $C_{1-6}$ alkylcarbonyl;

$X^b$ represents —NR$^e$—Y$^b$—R$^d$;

$R^e$ is a hydrogen atom or $C_{1-6}$ alkyl;

$R^d$ is a hydrogen atom, $C_{1-6}$ alkyl, or group —CO—C(R⁷)=CH₂;

$Y^b$ is —CH₂—(CHR⁵)ₗ₋₂—CH₂—NH—, —CH₂—(CHR⁶)ₚ₋₂—CH₂—O—, —(CH₂)ⱼ—S—, —CH₂—CH₂—(Y³—CH₂—CH₂)_z—S—, —CH₂—CH₂—(Y⁴—CH₂—CH₂)_t—NH—, or —CH₂—CH₂—(Y⁵—CH₂—CH₂)_y—O—, wherein each of l, p, and j is independently an integer selected from 2 to 10, each of z, t, and y is independently an integer selected from 1 to 200, R⁵ and R⁶ are each independently a hydrogen atom or hydroxy, R⁷ is a hydrogen atom or methyl, and Y³, Y⁴, and Y⁵ are each independently —O— or —NH—.

21. The hyaluronic acid derivative of claim 20, wherein $X^b$ is —NR$^i$—(CH₂)ₙ₂—OH wherein R$^i$ is a hydrogen atom and n2 is an integer selected from 2 to 10.

22. The hyaluronic acid derivative of claim 20, wherein a percentage of the repeating unit(s) represented by the formula (II) relative to the disaccharide repeating unit(s) present is 50% or less.

23. The hyaluronic acid derivative of claim 13, further comprising a repeating unit represented by the formula (IV):

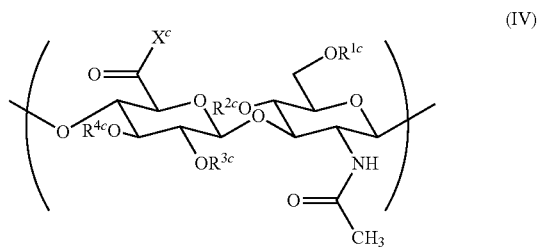

(IV)

wherein $R^{2c}$, $R^{3c}$, and $R^{4c}$ are each independently selected from a hydrogen atom, $C_{1-6}$ alkyl, formyl, and $C_{1-6}$ alkylcarbonyl;

$X^c$ is selected from hydroxy and —O⁻Q⁺, wherein Q⁺ is a counter cation;

$R^{1c}$ is selected from
—CO—C(R²¹)=CH₂,
—CH₂CH(OH)—R²²—Y¹,
—CH(CH₂OH)—R²²—Y¹,
—CONH—R²³—Y¹,
—CO—R²³—Y¹,
—CONH—CH₂CH₂—(X²¹—CH₂CH₂)ₙ₃—Y¹, and
—CO—CH₂CH₂—(X²¹—CH₂CH₂)ₙ₄—Y¹, wherein $X^{21}$ is selected from O and S;

each of n3 and n4 represents an integer of 1 to 50;

$Y^1$ is selected from amino, mercapto, formyl, and —X¹⁴—CO—C(R¹⁸)=CH₂;

$R^{21}$ is selected from a hydrogen atom and $C_{1-6}$ alkyl;

each of $R^{22}$ and $R^{23}$ are a divalent $C_{2-50}$ hydrocarbon group or a divalent $C_{2-50}$ polyalkyleneoxy group, wherein the divalent $C_{2-50}$ hydrocarbon group may partially contain a polyalkyleneoxy moiety formed by insertion of 1 to 10 —O— atoms;

$X^{14}$ is selected from O and N(R¹⁹);

$R^{18}$ is a hydrogen atom or $C_{1-6}$ alkyl; and $R^{19}$ is a hydrogen atom or $C_{1-6}$ alkyl.

24. The hyaluronic acid derivative of claim 13, substantially comprising at least one repeating unit represented by the formula (I); and at least one repeating unit represented by the formula (II), (III), or (IV).

25. The hyaluronic acid derivative of claim 13, which forms a particle by association in water.

26. A pharmaceutical composition comprising as a carrier the hyaluronic acid derivative of claim 13.

27. The pharmaceutical composition of claim 26, wherein a drug forms a complex with the hyaluronic acid derivative.

28. A hyaluronic acid derivative-drug conjugate, wherein at least one drug is conjugated to the hyaluronic acid derivative of claim 13.

29. The pharmaceutical composition of claim 27, wherein the drug is a pharmacologically active protein or peptide.

30. A hyaluronic acid derivative containing a hydrophobic group, comprising at least one repeating unit represented by the formula (I):

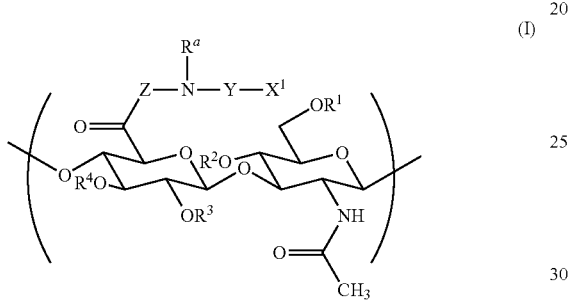

(I)

wherein
$R^1$, $R^2$, $R^3$, and $R^4$ are each independently selected from a hydrogen atom, $C_{1-6}$ alkyl, formyl, and $C_{1-6}$ alkylcarbonyl;

Z represents a direct bond;

$X^1$ is a hydrophobic group selected from the groups represented by the following formulas:

—$NR^b$—R,
—$NR^b$—CO—R,
—$NR^b$—CO—$NR^c$—R,
—COO—R,
—O—COO—R,
—S—R, and
—S—S—R;

$R^a$, $R^b$, and $R^c$ are each independently selected from a hydrogen atom, $C_{1-20}$ alkyl, amino $C_{2-20}$ alkyl, and hydroxy $C_{2-20}$ alkyl, wherein 1 to 3 groups selected from —O— and —$NR^f$— are optionally inserted in an alkyl moiety of these groups;

$R^f$ is selected from a hydrogen atom, $C_{1-12}$ alkyl, amino $C_{2-12}$ alkyl, and hydroxy $C_{2-12}$ alkyl, wherein 1 or 2 groups selected from —O— and —NH— are optionally inserted in an alkyl moiety of these groups;

R is a steryl group;

Y is $C_{2-30}$ alkylene or —$(CH_2CH_2O)_m$—$CH_2CH_2$—, wherein 1 to 5 groups selected from —O—, —$NR^g$—, and —S—S— are optionally inserted in the alkylene;

$R^g$ is selected from a hydrogen atom, amino $C_{2-20}$ alkyl, and hydroxy $C_{2-20}$ alkyl, wherein 1 to 3 groups selected from —O— and —NH— are optionally inserted in an alkyl moiety of these groups;

m is an integer selected from 1 to 100; and wherein the introduction ratio of the hydrophobic group(s) relative to the disaccharide repeating unit(s) present is 18 to 42%; and the introduction ratio is defined according to the following formula:

(Introduction ratio of hydrophobic group(s)) =

$$\frac{\text{(Number of repeating units of hydrophobic group − introduced disaccharide)}}{\text{(Number of disaccharide repeating units present)}} \times 100.$$

* * * * *